(12) United States Patent
Lin et al.

(10) Patent No.: US 7,264,973 B2
(45) Date of Patent: *Sep. 4, 2007

(54) LABEL-FREE METHODS FOR PERFORMING ASSAYS USING A COLORIMETRIC RESONANT OPTICAL BIOSENSOR

(75) Inventors: Bo Lin, Lexington, MA (US); Brian Cunningham, Lexington, MA (US); Peter Li, Andover, MA (US)

(73) Assignee: SRU Biosystems, Inc., Woburn, MA (US)

( * ) Notice: Subject to any disclaimer, the term of this patent is extended or adjusted under 35 U.S.C. 154(b) by 556 days.

This patent is subject to a terminal disclaimer.

(21) Appl. No.: 10/667,696

(22) Filed: Sep. 22, 2003

(65) Prior Publication Data

US 2004/0132214 A1    Jul. 8, 2004

Related U.S. Application Data

(63) Continuation-in-part of application No. 10/237,641, filed on Sep. 9, 2002, which is a continuation-in-part of application No. 10/227,908, filed on Aug. 26, 2002, now abandoned, and a continuation-in-part of application No. 10/180,374, filed on Jun. 26, 2002, now Pat. No. 7,023,544, and a continuation-in-part of application No. 10/180,647, filed on Jun. 26, 2002, which is a continuation-in-part of application No. 10/059,060, filed on Jan. 28, 2002, now Pat. No. 7,070,987, and a continuation-in-part of application No. 10/058,626, filed on Jan. 28, 2002, now Pat. No. 6,951,715, which is a continuation-in-part of application No. 09/930,352, filed on Aug. 15, 2001, now Pat. No. 7,094,595.

(60) Provisional application No. 60/303,028, filed on Jul. 3, 2001, provisional application No. 60/283,314, filed on Apr. 12, 2001, provisional application No. 60/244,312, filed on Oct. 30, 2000.

(51) Int. Cl.
*G01N 33/543* (2006.01)

(52) U.S. Cl. ............... 436/518; 422/82.05; 422/82.11; 435/5; 435/6; 435/7.21; 435/7.32; 435/287.2; 435/288.7; 435/808; 436/164; 436/512; 436/514; 436/524; 436/525; 436/527; 436/805; 436/809

(58) Field of Classification Search ................. None
See application file for complete search history.

(56) References Cited

U.S. PATENT DOCUMENTS 3,689,346 A    9/1972    Rowland .................. 156/245

(Continued)

FOREIGN PATENT DOCUMENTS

CA    2394966    2/2001

(Continued)

OTHER PUBLICATIONS

*Corning Inc. v. SRU Biosystems, Inc.*, Memorandum Opinion dated Nov. 15, 2005 in the United States District Court for the district of Delaware.

(Continued)

*Primary Examiner*—Christopher L. Chin
(74) *Attorney, Agent, or Firm*—McDonnell Boehnen Hulbert & Berghoff LLP

(57) ABSTRACT

The instant invention provides compositions and methods for determining cell interactions that are faster than conventional methods and that require the use of fewer reagents than conventional methods.

8 Claims, 41 Drawing Sheets

U.S. PATENT DOCUMENTS

| | | | |
|---|---|---|---|
| 3,810,688 A | 5/1974 | Ballman et al. ............... 350/96 |
| 3,856,604 A | 12/1974 | Hershler et al. ............. 156/361 |
| 4,009,933 A | 3/1977 | Firester |
| 4,050,895 A | 9/1977 | Hardy et al. ................ 436/527 |
| 4,240,751 A | 12/1980 | Linnecke et al. ........... 356/409 |
| 4,289,371 A | 9/1981 | Kramer ...................... 350/3.71 |
| 4,344,438 A | 8/1982 | Schultz ....................... 128/633 |
| 4,420,502 A | 12/1983 | Conley ...................... 427/54.1 |
| 4,536,608 A | 8/1985 | Sheng et al. |
| 4,560,248 A | 12/1985 | Cramp et al. ................. 385/12 |
| 4,576,850 A | 3/1986 | Martens |
| 4,608,344 A | 8/1986 | Carter et al. .................. 436/34 |
| 4,650,329 A | 3/1987 | Barrett et al. ................ 356/481 |
| 4,652,290 A | 3/1987 | Cho et al. ....................... 65/31 |
| 4,668,558 A | 5/1987 | Barber |
| 4,701,008 A | 10/1987 | Richard et al. ............. 385/132 |
| 4,810,658 A | 3/1989 | Shanks et al. .............. 436/172 |
| 4,815,843 A | 3/1989 | Tiefenthaler et al. ........ 356/128 |
| 4,818,710 A | 4/1989 | Sutherland et al. ......... 436/527 |
| 4,857,273 A | 8/1989 | Stewart ....................... 436/82 |
| RE33,064 E | 9/1989 | Carter ......................... 436/34 |
| 4,876,208 A | 10/1989 | Gustafson et al. |
| 4,882,288 A | 11/1989 | North et al. ................ 436/525 |
| 4,931,384 A | 6/1990 | Layton et al. |
| 4,952,056 A | 8/1990 | Tiefenthaler ............... 356/73.1 |
| 4,958,895 A | 9/1990 | Wells et al. ............. 350/96.12 |
| 4,992,385 A | 2/1991 | Godfrey |
| 4,999,234 A | 3/1991 | Cowan |
| 5,071,248 A | 12/1991 | Tiefenthaler et al. ........ 356/128 |
| 5,118,608 A | 6/1992 | Layton et al. |
| 5,155,785 A | 10/1992 | Holland et al. ................ 385/89 |
| 5,156,785 A | 10/1992 | Zdrahala ...................... 264/108 |
| 5,170,448 A | 12/1992 | Ackley et al. ................ 385/31 |
| 5,175,030 A | 12/1992 | Lu et al. |
| 5,210,404 A | 5/1993 | Cush et al. .................. 250/216 |
| 5,229,614 A | 7/1993 | Andersson et al. |
| 5,242,828 A | 9/1993 | Bergström et al. .......... 435/291 |
| 5,268,782 A | 12/1993 | Wenz et al. |
| 5,310,686 A | 5/1994 | Sawyers et al. |
| 5,337,183 A | 8/1994 | Rosenblatt ................... 359/248 |
| 5,413,884 A | 5/1995 | Koch et al. |
| 5,442,169 A | 8/1995 | Kunz |
| 5,455,178 A | 10/1995 | Fattinger |
| 5,475,780 A | 12/1995 | Mizrahi ........................ 385/37 |
| 5,478,527 A | 12/1995 | Gustafson et al. |
| 5,478,756 A | 12/1995 | Gizeli et al. |
| 5,492,840 A | 2/1996 | Malmqvist et al. |
| 5,496,701 A | 3/1996 | Pollard-Knight |
| 5,559,338 A | 9/1996 | Elliott et al. |
| 5,598,267 A | 1/1997 | Sambles et al. |
| 5,598,300 A | 1/1997 | Magnusson et al. |
| 5,606,170 A | 2/1997 | Saaski et al. ............. 250/458.1 |
| 5,615,052 A | 3/1997 | Doggett |
| 5,629,214 A | 5/1997 | Crosby ....................... 436/518 |
| 5,631,171 A | 5/1997 | Sandstrom et al. .......... 436/518 |
| 5,690,894 A | 11/1997 | Pinkel et al. |
| 5,691,846 A | 11/1997 | Benson, Jr. et al. |
| 5,732,173 A | 3/1998 | Bylander et al. |
| 5,738,825 A | 4/1998 | Rudigier et al. |
| 5,768,461 A | 6/1998 | Svetkoff et al. ............. 385/116 |
| 5,771,328 A | 6/1998 | Wortman et al. |
| 5,792,411 A | 8/1998 | Morris et al. |
| 5,801,390 A | 9/1998 | Shiraishi ................... 250/559.3 |
| 5,804,453 A | 9/1998 | Chen |
| 5,814,524 A | 9/1998 | Walt et al. ................... 436/514 |
| 5,821,343 A | 10/1998 | Keogh |
| 5,846,843 A | 12/1998 | Simon |
| 5,864,641 A | 1/1999 | Murphy et al. ............... 385/12 |
| 5,922,550 A | 7/1999 | Everhart et al. ............ 435/7.21 |
| 5,925,878 A | 7/1999 | Challener |
| 5,955,335 A | 9/1999 | Thust et al. |
| 5,955,378 A | 9/1999 | Challener |
| 5,986,762 A | 11/1999 | Challener |
| 5,991,480 A | 11/1999 | Kunz et al. |
| 5,994,150 A | 11/1999 | Challener et al. |
| 6,035,089 A | 3/2000 | Grann et al. |
| 6,052,213 A | 4/2000 | Burt et al. .................... 359/237 |
| 6,076,248 A | 6/2000 | Hoopman et al. |
| 6,088,505 A | 7/2000 | Hobbs |
| 6,100,991 A | 8/2000 | Challener |
| 6,128,431 A | 10/2000 | Siminovitch ................ 385/147 |
| 6,146,593 A | 11/2000 | Pinkel et al. ............... 422/68.1 |
| 6,185,019 B1 | 2/2001 | Hobbs et al. .................. 359/30 |
| 6,200,737 B1 | 3/2001 | Walt et al. ................... 430/320 |
| 6,215,928 B1 | 4/2001 | Friesem et al. ............... 385/37 |
| 6,218,194 B1 | 4/2001 | Lyndin et al. ............... 436/518 |
| 6,235,488 B1 | 5/2001 | Tom-Moy et al. |
| 6,303,179 B1 | 10/2001 | Koulik et al. |
| 6,316,153 B1 | 11/2001 | Goodman et al. ............. 430/8 |
| 6,320,991 B1 | 11/2001 | Challener et al. |
| RE37,473 E | 12/2001 | Challener |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. ..................... 385/12 |
| 6,404,554 B1 | 6/2002 | Lee et al. .................... 359/576 |
| 6,449,097 B1 | 9/2002 | Zhu et al. .................... 359/576 |
| 6,579,673 B2 | 6/2003 | McGrath et al. ................ 435/5 |
| 6,587,276 B2 | 7/2003 | Daniell ....................... 359/622 |
| 6,661,952 B2 | 12/2003 | Simpson et al. .............. 385/37 |
| 6,707,561 B1 | 3/2004 | Budach et al. ............... 356/521 |
| 6,748,138 B2 | 6/2004 | Wang et al. ................... 385/37 |
| 6,902,703 B2 | 6/2005 | Marquiss et al. |
| 2002/0018610 A1 | 2/2002 | Challener et al. |
| 2002/0171045 A1 | 11/2002 | Perraut |
| 2003/0003599 A1 | 1/2003 | Wagner et al. |
| 2003/0027327 A1 | 2/2003 | Cunningham et al. |
| 2003/0027328 A1 | 2/2003 | Cunningham et al. |
| 2003/0148542 A1 | 8/2003 | Pawlak |
| 2003/0210396 A1 | 11/2003 | Hobbs et al. ............... 356/416 |

FOREIGN PATENT DOCUMENTS

| | | |
|---|---|---|
| CA | 2395318 | 2/2001 |
| CA | 2394966 | 8/2001 |
| CA | 2395318 | 8/2001 |
| CH | 669050 A5 | 2/1989 |
| CH | 670521 A5 | 6/1989 |
| EP | 0 112 721 | 7/1984 |
| EP | 0326219 | 1/1989 |
| EP | 0326291 | 8/1989 |
| EP | 0 517 777 | 5/1996 |
| EP | 0 660 924 | 9/1999 |
| FR | 2801977 | 2/1999 |
| FR | 2801977 | 12/1999 |
| GB | 2156970 A | 10/1985 |
| GB | 2 227 089 | 7/1990 |
| WO | 8100912 | 4/1981 |
| WO | 0075353 | 3/1983 |
| WO | WO84/02578 | 7/1984 |
| WO | 8607149 | 12/1986 |
| WO | WO90/08318 | 7/1990 |
| WO | WO91/13339 | 9/1991 |
| WO | WO92/21768 | 12/1992 |
| WO | WO93/14392 | 7/1993 |
| WO | WO95/03538 | 2/1995 |
| WO | WO98/57200 | 12/1998 |
| WO | WO99/09392 | 2/1999 |
| WO | WO99/09396 | 2/1999 |
| WO | 9954714 | 10/1999 |
| WO | WO99/66330 | 12/1999 |
| WO | WO 00/23793 | 4/2000 |
| WO | 0029830 | 5/2000 |

| WO | WO 01/04697 | 1/2001 |

OTHER PUBLICATIONS

Liu, et al., "Development of an optical fiber lactate sensor", Mikrochimica Acta, 1999, 131(1-2). pp. 129-135.
Nellen, et al., "*Integrated Optical Input Grating Couplers as Biochemical Sensors*", Sensors and Actuators, 15 (1988) 285-295.
W. Lukosz and K. Tiefenthaler, "Embossing technique for fabricating integrated optical components in hard inorganic waveguiding materials," Optics Letters, vol. 8, pp. 537-539 (1983).
K. Tiefenthaler and W. Lukosz, "Integrated optical switches and gas sensors," Optics Letters, vol. 10, pp. 137-139 (1984).
Chabay, "Optical Waveguides," Analytical Chemistry, vol. 54, pp. 1071A-1080A (1982).
Sutherland et al., "Optical Detection of Antibody-Antigen Reactions at a Glass-Liquid Interface," Clin. Chem., vol. 30, pp. 1533-1538 (1984).
Ronald T. Holm and Edward D. Palik, "Internal-reflection spectroscopy," Laser Focus, vol. 15, pp. 60-65 (Aug. 1979).
N.J. Harrick and George I. Loeb, "Multiple Internal Reflection Fluorescence Spectrometry," Analytical Chemistry, vol. 45, pp. 687-691 (1973).
P.K. Tien, "Light Waves in Thin Films and Integrated Optics," Applied Optics, vol. 10, pp. 2395-2413 (1971).
Dakss, et. al., "Grating Coupler for Efficient Excitation of Optical Guided Waves in Thin Films," Applied Physics Letters, vol. 16, pp. 523-525 (1970).
Sutherland et al., "Immunoassays at a Quartz-Liquid Interface: Theory, Instrumentation and Preliminary Application to the Fluorescent Immunoassay of Human Immunoglobulin G," Journal of Immunological Methods, vol. 74, pp. 253-265 (1984).
English translation of CH 670 521 A5.
English translation of CH 669 050 A5.
Anderson, et al., "Proteomics: applications in basic and applied biology", Current Opinion in Biotechnology, 2000, 11:408-412.
MacBeath, et al., "Printing Proteins as Microarrays for High-Throughput Function Determination", Science, vol. 289, pp. 1760-1763, 2000.
deWildt, et a.., "Antibody arrays for high-throughput screening of antibody-antigen interactions", Nature Biotechnology, vol. 18, pp. 989-994, 2000.
Cunningham, et al., "A plastic colorimetric resonant optical biosenor for multiparallel detection of label-free biochemical interactions", Sensors and Actuators B, 85 (2002) 219-226.
Caruso, et al., "Quartz Crystal Microbalance Study of DNA Immobilization and Hybridization for Nucleic Acid Sensor Development", Analytical Chemistry, vol. 69, No. 11, pp. 2043-2049, 1997.
Hefti, et al, "Sensitive detection method of dielectric dispersions in aqueous-based, surface-bound macromolecular structures using microwave spectroscopy", Applied Physics Letters, vol. 75, No. 12, pp. 1802-1804, 1999.
Wu, et al., "Bioassay of prostate-specific antigen (PSA) using microcantilevers", Nature Biotechnology, vol. 19, pp. 856-860, 2001.
Wasserman, et al., "Structure and Reactivity of Alkylsiloxane Monolayers Formed by Reaction of Alkyltrichlorosilanes on Silicon Substrates", Langmuir, 5, 1074-1087, 1989.
Kallury, et al., "X-ray Photoelectron Spectroscopy of Silica Surfaces Treated with Polyfunctional Silanes", Anal. Chem., 60, 169-172, 1988.
Cunningham, et al., "Colorimetric resonant reflection as a direct biochemical assay technique", Sensors and Actuators B, 81 (2002) 316-328.
Mullaney, et al., "Epitope Mapping of Neutralizing Botulinum Neurotoxin A Antibodies by Phage Display", Infection and Immunity, vol. 69, No. 10, pp. 6511-6514, 2001.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
U.S. Appl. No. 09/929,957, filed Aug. 15, 2001.
U.S. Appl. No. 09/930,352, filed Aug. 15, 2001.
U.S. Appl. No. 10/415,037, filed Oct. 23, 2001.
U.S. Appl. No. 10/399,940, filed Oct. 23, 2001.
U.S. Appl. No. 10/059,060, filed Jan. 28, 2002.
U.S. Appl. No. 10/201,818, filed Jul. 23, 2002.
U.S. Appl. No. 10/237,641, filed Sep. 9, 2002.
U.S. Appl. No. 10/277,908, filed Aug. 26, 2002.
U.S. Appl. No. 10/233,730, filed Sep. 3, 2002.
U.S. Appl. No. 10/180,374, filed Jun. 26, 2002.
U.S. Appl. No. 10/180,647, filed Jun. 26, 2002.
U.S. Appl. No. 10/253,846, filed Sep. 25, 2002.
U.S. Appl. No. 10/196,058, filed Jul. 15, 2002.
U.S. Appl. No. 10/667,696, filed Sep. 22, 2003.
U.S. Appl. No. 10/058,626, filed Jan. 28, 2002.
Bertoni, et al., "Frequency-Selective Reflection and Transmission by a Periodic Dielectric Layer", IEEE Transactions on Antennas and Propagation, vol. 37, No. 1, pp. 78-83 (1989).
Brundrett, et al., "Normal-incidence guided-mode resonant grating filters: design and experimental demonstration", Optics Letters, vol. 23, No. 9, pp. 700-702 (1998).
Peng, "*Polarization-control Components and Narrow-band Filters Based on Subwavelength Grating Structures*" 1996.
Statement of Applicants dated Jun. 10, 2004.
Lenau, Torben; Material, Silicon Nitride, 1996, 97, 98.
Cerac, Technical publications: Tantalum Oxide, $Ta_2O_5$ for Optical Coating, 2000, Cerac, Inc.
U.S. Appl. No. 60/244,312, filed Oct. 30, 2000, Cunningham et al.
U.S. Appl. No. 60/283,314, filed Apr. 12, 2001, Cunningham et al.
U.S. Appl. No. 60/303,028, filed Jul. 3, 2001, Cunningham et al.
Brecht, et al., Biosensors & Bioelectronics vol. 10, pp. 923-936 (1995).
Challener, et al., Elsevier Science B. V., pp. 42-46 (2000).
Cowan, J. Opt. Soc. Am., vol. 7, No. 8, pp. 1529-1544 (1990).
Cowan, Optical Engineering, vol. 24, No. 5, pp. 796-802 (1985).
Cowan, SPIE vol. 503, Application, Theory, and Fabrication of Periodic Structures, pp. 120-129 (1984).
Cowan, et al., J. Imaging Sci., vol. 31, No. 3, pp. 100-107 (1987).
Cunningham, B. et al., Sensors and Actuators B 85; pp. 219-226 (2002).
Cunningham, B. et al., Sensors and Actuators B 81; pp. 316-328 (2002).
Cunningham, et al., Techniques in Analytical Chemistry, pp. 260-291.
Hobbs, et al., SPIE, vol. 3879, pp. 124-135, (1999).
Huber, et al., Sensors and Actuators B, 6, pp. 122-126 (1992).
Jenison, et al., Nature Biotechnology, vol. 19, pp. 62-64 (2001).
Jin, et al., Analytical Biochemistry, vol. 232, pp. 69-72 (1995).
Jordan, et al., Analytical Chemistry, vol. 69, No. 7, pp. 1449-1456 (1997).
Lin, et al., Science, vol. 278, pp. 840-843 (1997).
Magnusson, et al., Appl. Phys. Lett., vol. 61, No. 9, pp. 1022-1024 (1992).
Magnusson, et al., Applied Optics, vol. 34, No. 35, pp. 8106-8109 (1995).
Morhard, et al., Sensors and Actuators B 70; pp. 232-242 (2000).
Pandey, A. and Mann, M. Nature 15;405(6788):837-46 (2000).
Patel, et al., American Institute of Physcis, vol. 58, No. 22, pp. 2491-2493 (1991).
Patel, et al., IEEE Photonics Technology Letters, vol. 3, No. 7, pp. 643-644 (1991).
Patterson, S.D. Current Opinions in Biotechnology. 11(4):413-8 (2000).
Peng, et al., Optics Letters vol. 21, No. 8, pp. 549-551 (1996).
Peng, et al., J. Opt. Soc. Am. A., vol. 13, No. 5, pp. 993-1005 (1996).
Raguin, et al., Laser Focus World, pp. 113-117 (1997).
Sigal, et al., Analytical Chemistry, vol. 68, No. 3, pp. 490-497 (1996).

Wang, et al., *Optical Society of America*, vol. 19, No. 12, 919-921 (1994).

Wang, et al., *J. Opt. Soc. Am.*, vol. 7, No. 8, pp. 1470-1474 (1990).

Wang, et al., *Applied Optics*, vol. 32, No. 14, pp. 2606-2613 (1993).

International Search Report for foreign counterpart application PCT/US01/50723.

International Search Report for foreign counterpart application PCT/US03/01175.

Invitation to Pay Additional Fees in foreign counterpart application PCT/US01/50723.

Concentric Circle Design

Amine
- Sulfo-succinimidyl-6-(biotinamido)hexanoate (Sulfo-NHS-LC-Biotin)
  - Streptavidin / avidin then biotinylated molecule
- N,N'-disuccinimidyl carbonate (DSC); •-$NH_2$, non-cleavable
- Dimethyl pimelimidate (DMP); •-$NH_2$, non-cleavable
- Dimethyl 3,3'-dithiobispropionimidate (DTBP); •-$NH_2$, cleavable
- 1-Ethyl-3-(3-Dimethylaminopropyl)carbodiimide Hydrochloride (EDC) and N-Hydroxysulfosuccinimide (Sulfo-NHS); •-COOH
- Sulfo-succinimidyl 6-[a-methyl-a-(2-pyridyl-dithio)toluamido] hexanoate (Sulfo-LC-SMPT); •-SH, cleavable
- N-(B-Maleimidopropyloxy)succinimide ester (BMPS)
  - -$SH_2$, non-cleavable
- Sulfo-succinimidyl 4-[N-maleimidomethyl)cyclohexane-1-carboxylate (Sulfo-SMCC); •-SH, non-cleavable Aldehyde
- Directly with aldehyde or first amino then aldehyde
  - -$NH_2$ Ni(II)
- Using Nitrilotriacetic acid (NTA) group, which forms a chelate with Ni(II)
  - His-tagged molecules

Figure 8

LABEL-FREE METHODS FOR PERFORMING ASSAYS USING A COLORIMETRIC RESONANT OPTICAL BIOSENSOR

PRIORITY

This application is a continuation-in-part of U.S. application Ser. No. 10/237,641, filed Sep. 9, 2002, which is a continuation-in-part of U.S. application Ser. No. 10/227,908, entitled "Amine Chemical Surface Activation Process And Test Method For A Plastic Colorimetric Resonant Biosensor," filed Aug. 26, 2002 now abandoned and U.S. application Ser. No. 10/180,374, entitled "Colorimetric Resonant Biosensor Microarray Readout Instrument," filed Jun. 26, 2002, and U.S. application Ser. No. 10/180,647, entitled "Colorimetric Resonant Biosensor Microtiter Plate Readout Instrument" filed Jun. 26, 2002, which are continuations-in-part of U.S. application Ser. No. 10/059,060, filed Jan. 28, 2002 and U.S. application Ser. No. 10/058,626, filed Jan. 28, 2002, which are continuations-in-part of U.S. application Ser. No. 09/930,352, filed Aug. 15, 2001, which claims the benefit of U.S. provisional application 60/244,312 filed Oct. 30, 2000; U.S. provisional application 60/283,314 filed Apr. 12, 2001; and U.S. provisional application 60/303,028 filed Jul. 3, 2001, all of which are incorporated herein by reference in their entirety.

TECHNICAL AREA OF THE INVENTION

The invention relates to methods for detecting biomolecular interactions. The detection can occur without the use of labels and can be done in a high-throughput manner. The invention also relates to optical devices.

BACKGROUND OF THE INVENTION

With the completion of the sequencing of the human genome, one of the next grand challenges of molecular biology will be to understand how the many protein targets encoded by DNA interact with other proteins, small molecule pharmaceutical candidates, and a large host of enzymes and inhibitors. See e.g., Pandey & Mann, "Proteomics to study genes and genomes," *Nature*, 405, p. 837-846, 2000; Leigh Anderson et al., "Proteomics: applications in basic and applied biology," *Current Opinion in Biotechnology*, 11, p. 408-412, 2000; Patterson, "Proteomics: the industrialization of protein chemistry," *Current Opinion in Biotechnology*, 11, p. 413-418, 2000; MacBeath & Schreiber, "Printing Proteins as Microarrays for High-Throughput Function Determination," *Science*, 289, p. 1760-1763, 2000; De Wildt et al., "Antibody arrays for high-throughput screening of antibody-antigen interactions," *Nature Biotechnology*, 18, p. 989-994, 2000. To this end, tools that have the ability to simultaneously quantify many different biomolecular interactions with high sensitivity will find application in pharmaceutical discovery, proteomics, and diagnostics. Further, for these tools to find widespread use, they must be simple to use, inexpensive to own and operate, and applicable to a wide range of analytes that can include, for example, polynucleotides, peptides, small proteins, antibodies, and even entire cells.

Biosensors have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Signal transduction has been accomplished by many methods, including fluorescence, interferometry (Jenison et al., "Interference-based detection of nucleic acid targets on optically coated silicon," *Nature Biotechnology*, 19, p. 62-65; Lin et al., "A porous silicon-based optical interferometric biosensor," *Science*, 278, p. 840-843, 1997), and gravimetry (A. Cunningham, Bioanalytical Sensors, John Wiley & Sons (1998)).

Of the optically-based transduction methods, direct methods that do not require labeling of analytes with fluorescent compounds are of interest due to the relative assay simplicity and ability to study the interaction of small molecules and proteins that are not readily labeled. Direct optical methods include surface plasmon resonance (SPR) (Jordan & Corn, "Surface Plasmon Resonance Imaging Measurements of Electrostatic Biopolymer Adsorption onto Chemically Modified Gold Surfaces," *Anal. Chem.*, 69:1449-1456 (1997)), grating couplers (Morhard et al., "Immobilization of antibodies in micropatterns for cell detection by optical diffraction," *Sensors and Actuators B*, 70, p. 232-242, 2000), ellipsometry (Jin et al., "A biosensor concept based on imaging ellipsometry for visualization of biomolecular interactions," *Analytical Biochemistry*, 232, p. 69-72, 1995), evanescent wave devices (Huber et al., "Direct optical immunosensing (sensitivity and selectivity)," *Sensors and Actuators B*, 6, p. 122-126, 1992), and reflectometry (Brecht & Gauglitz, "Optical probes and transducers," *Biosensors and Bioelectronics*, 10, p. 923-936, 1995). Theoretically predicted detection limits of these detection methods have been determined and experimentally confirmed to be feasible down to diagnostically relevant concentration ranges. However, to date, these methods have yet to yield commercially available high-throughput instruments that can perform high sensitivity assays without any type of label in a format that is readily compatible with the microtiter plate-based or microarray-based infrastructure that is most often used for high-throughput biomolecular interaction analysis. Therefore, there is a need in the art for methods that can achieve these goals.

SUMMARY OF THE INVENTION

In one embodiment the invention provides a vessel comprising a colorimetric resonant reflectance optical biosensor. The colorimetric resonant reflectance optical biosensor comprises an internal surface of the vessel. One or more specific binding substances are immobilized at two or more distinct locations on the internal surface of the vessel that comprises a calorimetric resonant reflectance optical biosensor. The vessel can comprise a microtiter well, test tube, petri dish or microfluidic channel.

Another embodiment of the invention provides a microtiter plate comprising one or more microtiter wells, wherein a bottom surface of the one or more microtiter wells comprises a colorimetric resonant reflectance optical biosensor. One or more specific binding substances are immobilized at two or more distinct locations on the bottom surface of each microtiter well.

Yet another embodiment of the invention provides a method of detecting binding of one or more types of cells to one or more specific binding substances. The method comprises applying the one or more types of cells to an internal surface of a vessel, wherein the internal surface of the vessel comprises a colorimetric resonant reflectance optical biosensor, wherein one or more specific binding substances are immobilized at two or more distinct locations on the internal surface of the vessel that comprises a colorimetric resonant reflectance optical biosensor. The vessel is illuminated with light and one or more peak wavelength values (PWVs) are determined for each distinct location. If the one or more cells have bound to one or more specific binding substances, then the PWV is shifted at the distinct location to which the one or more cells are bound. The vessel can be a microtiter well, microtiter plate, test tube, petri dish or microfluidic channel. The one or more specific binding substances can be arranged in an array of distinct locations on the internal surface of the vessel that comprises a colorimetric resonant reflectance optical biosensor. The distinct locations can define an array of spots of about 50-500 microns in diameter. The one or more specific binding substances can be immobilized on the internal surface of the vessel that comprises a colorimetric resonant reflectance optical biosensor by a method selected from the group consisting of physical adsorption, chemical binding, electrochemical binding, electrostatic binding, hydrophobic binding and hydrophilic binding. The one or more specific binding substances are selected from the group consisting of nucleic acids, peptides, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, $F(ab')_2$ fragment, Fv fragment, small organic molecule, cell, virus, bacteria, polymer and biological sample.

Still another embodiment of the invention provides a method of detecting binding of one or more cells to one or more specific binding substances. The method comprises immobilizing one or more specific binding substances to two or more distinct locations on an internal surface of a vessel, wherein the internal surface of the vessel comprises a calorimetric resonant reflectance optical biosensor. The vessel is illuminated with light. One or more peak wavelength values (PWVs) are detected for each distinct location. One or more cells are applied to the internal surface of the vessel. The vessel is illuminated with light. One or more peak wavelength values (PWVs) are determined for each distinct location. The PWVs taken before the cells are added are compared to the PWVs that are taken after the cells are added. If the one or more cells have bound to a specific binding substance, then the PWV is shifted at the distinct location to which the cells are bound.

BRIEF DESCRIPTION OF THE DRAWINGS

FIG. 8 shows three types of surface activation chemistry (Amine, Aldehyde, and Nickel) with corresponding chemical linker molecules that can be used to covalently attach various types of biomolecule receptors to a biosensor.

FIG. 16A shows results of streptavidin detection at various concentrations for a biosensor that has been activated with $NH_2$ surface chemistry linked to a biotin receptor molecule. FIG. 16B shows a schematic demonstration of molecules bound to a biosensor.

FIG. 17A shows an assay for detection of anti-goat IgG using a goat antibody receptor molecule. BSA blocking of a detection surface yields a clearly measurable background signal due to the mass of BSA incorporated on the biosensor. A 66 nM concentration of anti-goat IgG is easily measured above the background signal. FIG. 17B shows a schematic demonstration of molecules bound to a biosensor.

FIG. 18A shows a nonlabeled ELISA assay for interferon-gamma (INF-gamma) using an anti-human IgG INF-gamma receptor molecule, and a neural growth factor (NGF) negative control. FIG. 18B shows a schematic demonstration of molecules bound to a biosensor.

FIG. 19A shows detection of a 5-amino acid peptide (MW=860) and subsequent cleavage of a pNA label (MW=130) using enzyme caspase-3. FIG. 19B shows a schematic demonstration of molecules bound to a biosensor.

FIG. 20A shows resonant peak in liquid during continuous monitoring of the binding of three separate protein layers. FIG. 20B shows a schematic demonstration of molecules bound to a biosensor.

FIG. 21A shows endpoint resonant frequencies mathematically determined from the data shown in FIG. 21. FIG. 21B shows a schematic demonstration of molecules bound to a biosensor.

FIG. 22A shows kinetic binding measurement of IgG binding. FIG. 22B shows a schematic demonstration of molecules bound to a biosensor.

FIG. 23A shows kinetic measurement of a protease that cleaves bound protein from a biosensor surface. FIG. 23B shows a schematic demonstration of molecules bound to a biosensor.

FIG. 32A shows a biosensor that is incorporated into a microtiter plate. FIG. 32B shows a biosensor in a microarray slide format.

FIG. 34A shows a measure resonant wavelength shift caused by attachment of a strepavidin receptor layer and subsequent detection of a biotinylated IgG. FIG. 34B shows a schematic demonstration of molecules bound to biosensor.

FIG. 35A shows the spotting of rabbit, chicken, goat, and human IgG on a colorimetric resonant reflectance biosensor microarray. FIG. 35B shows the result of flowing anti-human-IgG over the sensor surface, indicating greater binding between the human-IgG and the anti-human-IgG.

FIG. 36A shows the different degrees of hybridization affinities between the immobilized oligonucleotides with Poly-T, Poly-A, and T7-promoter. FIG. 36-B shows the endpoint data with error bars.

DETAILED DESCRIPTION OF THE INVENTION

Figure 1A:
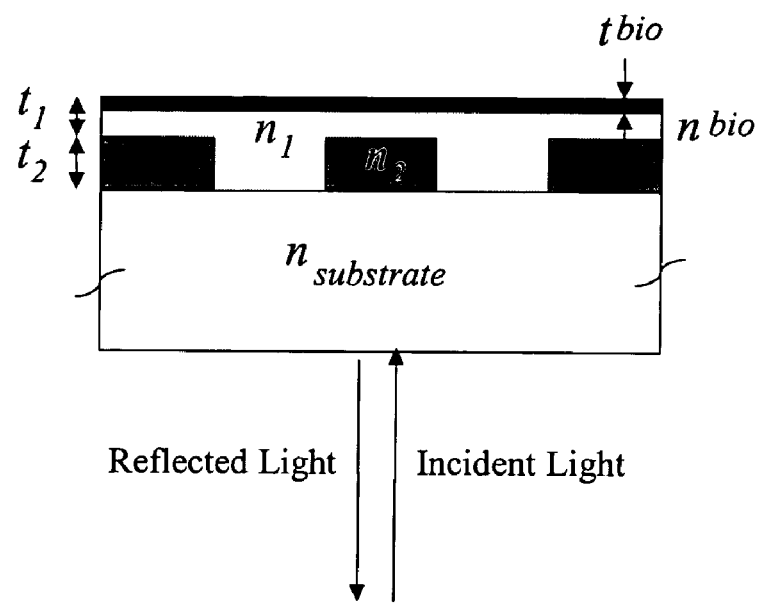
FIG. 1A shows a cross-sectional view of a biosensor wherein light is shown as illuminating the bottom of the biosensor; however, light can illuminate the biosensor from either the top or the bottom.

A colorimetric resonant reflectance optical biosensor allows biochemical interactions to be measured on the biosensor's surface without the use of fluorescent tags, calorimetric labels or any other type of tag or label. A biosensor surface contains an optical structure that, when illuminated with collimated white light, is designed to reflect only a narrow band of wavelengths. The narrow wavelength band is described as a wavelength "peak." The "peak wavelength value" (PWV) changes when materials, such as biological materials, are deposited or removed from the biosensor surface. A readout instrument is used to illuminate distinct locations on a biosensor surface with collimated white light, and to collect collimated reflected light. The collected light is gathered into a wavelength spectrometer for determination of PWV.

A biosensor structure can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment.

The functional advantages of each of the assay methods defined in this disclosure arise from the properties of a colorimetric resonant reflectance biosensor. First, biochemical interactions are measured without the use of labels. Second, many interactions can be monitored simultaneously. Third, the biosensor is incorporated into a standard microtiter plate for isolation and liquid containment of parallel assays.

For the majority of assays currently performed for genomics, proteomics, pharmaceutical compound screening, and clinical diagnostic applications, fluorescent or calorimetric chemical labels are commonly attached to the molecules under study so they may be readily visualized. Because attachment of a label substantially increases assay complexity and possibly alters the functionality of molecules through conformational modification or epitope blocking, various label-free biosensor technologies have emerged. Label-free detection phenomenologies include measuring changes in mass, microwave transmission line characteristics, microcantilever deflection, or optical density upon a surface that is activated with a receptor molecule with high affinity for a detected molecule. The widespread commercial acceptance of label-free biosensor technologies has been limited by their ability to provide high detection sensitivity and high detection parallelism in a format that is inexpensive to manufacture and package. For example, biosensors fabricated upon semiconductor or glass wafers in batch photolithography, etch and deposition processes are costly to produce and package if the biosensor area is to be large enough to contain large numbers of parallel assays. Similarly, the requirement of making electrical connections to individual biosensors in an array poses difficult challenges in terms of package cost and compatibility with exposure of the biosensor to fluids.

DEFINITIONS

Colorimetric Resonant Reflectance Optical Biosensor:

"Colorimetric resonant reflectance optical biosensors," alternatively referred to herein as biosensors, are defined herein as subwavelength structured surface (SWS) biosensors and surface-relief volume diffractive (SRVD) biosensors. See, e.g., U.S. application Ser. No. 10/059,060 entitled "Resonant Reflection Microarray" and U.S. Ser. No. 10/180,374, and U.S. Ser. No. 10/180,647.

Entire Specific Binding Substance:

"Entire specific binding substance," as used herein, refers to substantially the entirety of a molecule of interest, such that, for example, the cleavage of substantially an entire specific binding substance from the surface of a colorimetric resonant reflectance optical biosensor yields the substantially complete, native specific binding substance.

Microtiter Plate:

"Microtiter plate," as used herein, is defined as a microtiter or multiwell plate of 2, 6, 8, 24, 48, 96, 384, 1536 or 3456 well formats, or any other number of wells.

Test Reagent:

"Test reagent," as used herein, is defined as any enzyme or chemical compound and solutions thereof. Non-limiting examples of enzymes are proteases, lipases, nucleases, lyases, peptidases, hydrolases, ligases, kinases and phosphatases. In addition to the enzymes, chemical compounds and solutions thereof, "test reagent" also refers to buffer blanks thereof. A buffer blank refers to reagents or solutions identical in composition to those added to the other recited test reagents, with the enzyme component omitted.

Semi-Permeable Internal Sleeve:

A "semi-permeable internal sleeve," alternatively referred to as "insert" or "sleeve" herein, is defined as a porous material that is capable of supporting cell growth. A semi-permeable internal sleeve is permeable to proteins or other molecules secreted, shed or otherwise ejected from the cell grown on the sleeve surface but impermeable to a whole cell. A semi-permeable internal sleeve is generally held a short distance from the surface of a biosensor to which specific binding substances are bound or the growth media or buffer on the surface of a biosensor such that free diffusion of the secreted, shed or otherwise ejected moieties can occur through the sleeve. A semi-permeable internal sleeve can reside on any kind of colorimetric resonant reflectance optical biosensor, as defined above, within or without a well of a microtiter plate.

A semi-permeable internal sleeve that is "held in contact" with a surface of a biosensor or the surface of growth media or buffer on the surface of a biosensor is defined herein as (1) being positioned such that the sleeve is in close proximity to, but not in direct physical contact with the surface of the biosensor; (2) being positioned such that the sleeve is in physical contact with the surface of the buffer or growth media that is positioned on the biosensor surface; or (3) being positioned or connected in any manner such that diffusion of molecules secreted, shed or otherwise ejected from the cells through the semi-permeable internal sleeve is facilitated and, preferably, unhindered. "Held in contact" is also referred to as sitting or fitting "adjacent to the biosensor surface."

The types of material used as semi-permeable internal sleeve can be, for example, polyethylene terephthalate (PET) or polytetrafluoroethylene (PTFE) such as the material used within commercially available cell culture inserts (BD Falcon, Millipore).

Inhibition Activity:

"Inhibition activity" is defined herein as the ability of a molecule or compound to slow or stop another molecule from carrying out catalytic activity. For example, a compound that has inhibition activity of a protease inhibits the protease from cleaving a protein. Such inhibition activity is carried out "against" the catalytic molecule. "Inhibition activity" also means the ability of a molecule or compound to substantially inhibit or partially inhibit the binding of a binding partner to a specific binding substance.

Nucleic Acid:

"Nucleic acid" is defined herein as single or double stranded polymers of natural or non-natural nucleotides or derivatives thereof, linked by 3',5' phosphodiester linkages.

Oligonucleotide:

"Oligonucleotide" is defined herein as a single or double stranded polymer sequence of natural or non-natural nucleotides or derivatives thereof joined by phosphodiester bonds. "Oligonucleotide" generally refers to short polynucleotides of a length approximately 20 bases or less, beyond which they are preferentially referred to a polynucleotides.

Protein:

"Protein" is defined herein as a linear polymer of natural or non-natural amino acids or derivatives thereof joined by peptide bonds in a specific sequence.

Peptide:

"Peptide" is defined herein as any of a class of molecules that hydrolyze into amino acids and form the basic building blocks of proteins. Generally refers to a short polypeptide or protein fragment.

Combinatorial Chemical Library:

"Combinatorial chemical library" is defined herein as a diverse set of molecules resulting from the combination of their constituent building block materials in myriad ways.

Cell Membrane:
"Cell membrane" is defined herein as the external, limiting lipid bilayer membrane of cells.

Tissue:
"Tissue" is defined herein as a group of cells, often of mixed types and usually held together by extracellular matrix, that perform a particular function. Also, in a more general sense, "tissue" can refer to the biological grouping of a cell type result from a common factor; for example, connective tissue, where the common feature is the function or epithelial tissue, where the common factor is the pattern of organization.

Receptor:
"Receptor" is defined herein as a membrane-bound or membrane-enclosed molecule that binds to, or responds to something more mobile (the ligand), with high specificity.

Ligand:
"Ligand" is defined herein as a molecule that binds to another; in normal usage a soluble molecule, such as a hormone or neurotransmitter, that binds to a receptor. Also analogous to "binding substance" herein.

Cytokine:
"Cytokine" is defined herein as proteins released by cells and that affect the behavior of other cells. Similar to "hormone", but the term tends to be used as a generic word for interleukins, lymphokines and several related signaling molecules such as TNF and interferons.

Chemokine:
"Chemokine" is defined herein as small secreted proteins that stimulate chemotaxis of leucocytes.

Extracellular Matrix Material:
"Extracellular Matrix Material" is defined herein as any material produced by cells and secreted into the surrounding medium, but usually applied to the non-cellular portion of animal tissues.

Antigen:
"Antigen" is defined herein as a substance inducing an immune response. The antigenic determinant group is termed an epitope, and the epitope in the context of a carrier molecule (that can optionally be part of the same molecule, for example, botulism neurotoxin A, a single molecule, has three different epitopes. See Mullaney et al., Infect Immun 2001 October; 69(10): 6511-4) makes the carrier molecule active as an antigen. Usually antigens are foreign to the animal in which they produce immune reactions.

Polyclonal Antibody:
"Polyclonal antibody" is defined herein as an antibody produced by several clones of B-lymphocytes as would be the case in a whole animal. Usually refers to antibodies raised in immunized animals.

Monoclonal Antibody:
"Monoclonal antibody" is defined herein as a cell line, whether within the body or in culture, that has a single clonal origin. Monoclonal antibodies are produced by a single clone of hybridoma cells, and are therefore a single species of antibody molecule.

Single Chain Antibody (Scfv):
"Single chain antibody (Scfv)" is defined herein as a recombinant fusion protein wherein the two antigen binding regions of the light and heavy chains (Vh and Vl) are connected by a linking peptide, which enables the equal expression of both the light and heavy chains in a heterologous organism and stabilizes the protein.

F(Ab) Fragment:
"F(Ab) fragment" is defined herein as fragments of immunoglobulin prepared by papain treatment. Fab fragments consist of one light chain linked through a disulphide bond to a portion of the heavy chain, and contain one antigen binding site. They can be considered as univalent antibodies.

F(Ab')2 Fragments:
"F(Ab')2 Fragments" is defined herein as the approximately 90 kDa protein fragment obtained upon pepsin hydrolysis of an immunoglobulin molecule N-terminal to the site of the pepsin attack. Contains both Fab fragments held together by disulfide bonds in a short section of the Fc fragment.

Fv Fragments:
"Fv Fragments" is defined herein as the N-terminal portion of a Fab fragment of an immunoglobulin molecule, consisting of the variable portions of one light chain and one heavy chain.

Small Organic Molecules:
"Small Organic Molecules" is defined herein as any small carbon-containing molecule that is not otherwise classified as one of the above-defined organic molecules, such as, for example, a polypeptide.

Subwavelength Structured Surface (SWS) Biosensor

In one embodiment of the invention, a subwavelength structured surface (SWS) is used to create a sharp optical resonant reflection at a particular wavelength that can be used to track with high sensitivity the interaction of biological materials, such as specific binding substances or binding partners or both. A calorimetric resonant reflectance diffractive grating surface acts as a surface binding platform for specific binding substances.

Subwavelength structured surfaces are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.,* 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. A SWS surface narrowband filter can comprise a grating sandwiched between a substrate layer and a cover layer that fills the grating grooves. Optionally, a cover layer is not used. When the effective index of refraction of the grating region is greater than the substrate or the cover layer, a waveguide is created. When a filter is designed properly, incident light passes into the waveguide region and propagates as a leaky mode. A grating structure selectively couples light at a narrow band of wavelengths into the waveguide. The light propagates only a very short distance (on the order of 10-100 micrometers), undergoes scattering, and couples with the forward- and backward-propagating zeroth-order light. This highly sensitive coupling condition can produce a resonant grating effect on the reflected radiation spectrum, resulting in a narrow band of reflected or transmitted wavelengths. The depth and period of the grating are less than the wavelength of the resonant grating effect.

The reflected or transmitted color of this structure can be modulated by the addition of molecules such as specific binding substances or binding partners or both to the upper surface of the cover layer or the grating surface. The added molecules increase the optical path length of incident radiation through the structure, and thus modify the wavelength at which maximum reflectance or transmittance will occur.

In one embodiment, a biosensor, when illuminated with white light, is designed to reflect only a single wavelength or a narrow band of wavelengths. When specific binding substances are attached to the surface of the biosensor, the reflected wavelength is shifted due to the change of the optical path of light that is coupled into the grating. By linking specific binding substances to a biosensor surface, complementary binding partner molecules can be detected without the use of any kind of fluorescent probe, particle label or any other type of label. The detection technique is capable of resolving changes of, for example, ~0.1 nm thickness of protein binding, and can be performed with the biosensor surface either immersed in fluid or dried.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates and microarray slides. A single spectrometer reading can be performed in several milliseconds, thus it is possible to quickly measure a large number of molecular interactions taking place in parallel upon a biosensor surface, and to monitor reaction kinetics in real time.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

Figure 1B:
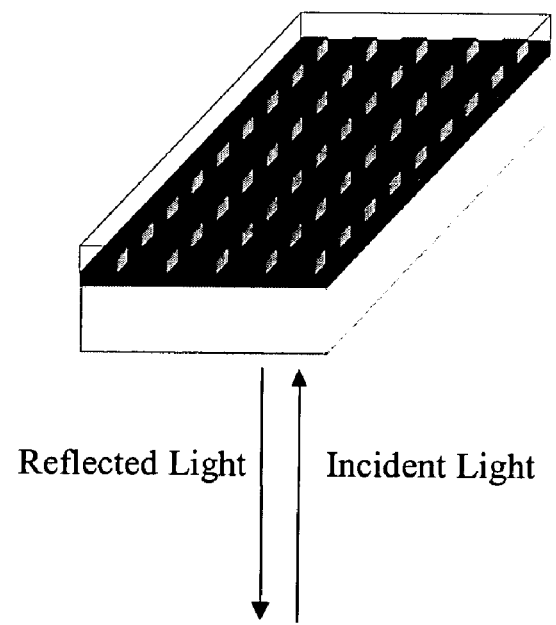
FIG. 1B shows a diagram of a biosensor wherein light is shown as illuminating the bottom of the biosensor; however, light can illuminate the biosensor from either the top or the bottom.

FIGS. 1A and 1B are diagrams of an example of a colorimetric resonant reflection diffractive grating biosensor. In FIG. 1, $n_{substrate}$ represents a substrate material. $n_2$ represents the refractive index of an optical grating. $n_1$ represents an optional cover layer. $n_{bio}$ represents the refractive index of one or more specific binding substances. $t_1$ represents the thickness of the optional cover layer above the one-, two- or three-dimensional grating structure. $t_2$ represents the thickness of the grating. $t_{bio}$ represents the thickness of the layer of one or more specific binding substances. In one embodiment, are n2<n1 (see FIG. 1A). Layer thicknesses (i.e. cover layer, one or more specific binding substances, or an optical grating) are selected to achieve resonant wavelength sensitivity to additional molecules on the top surface. The grating period is selected to achieve resonance at a desired wavelength.

A SWS biosensor comprises an optical grating comprised of a high refractive index material, a substrate layer that supports the grating, and one or more specific binding substances immobilized on the surface of the grating opposite of the substrate layer. Optionally, a cover layer covers the grating surface. An optical grating made according to the invention is coated with a high refractive index dielectric film which can be comprised of a material that includes, for example, zinc sulfide, titanium dioxide, tantalum oxide, and silicon nitride. A cross-sectional profile of a grating with optical features can comprise any periodically repeating function, for example, a "square-wave." An optical grating can also comprise a repeating pattern of shapes selected from the group consisting of lines, squares, circles, ellipses, triangles, trapezoids, sinusoidal waves, ovals, rectangles, and hexagons. A biosensor of the invention can also comprise an optical grating comprised of, for example, plastic or epoxy, which is coated with a high refractive index material.

Sensor Characteristics

Figure 2:
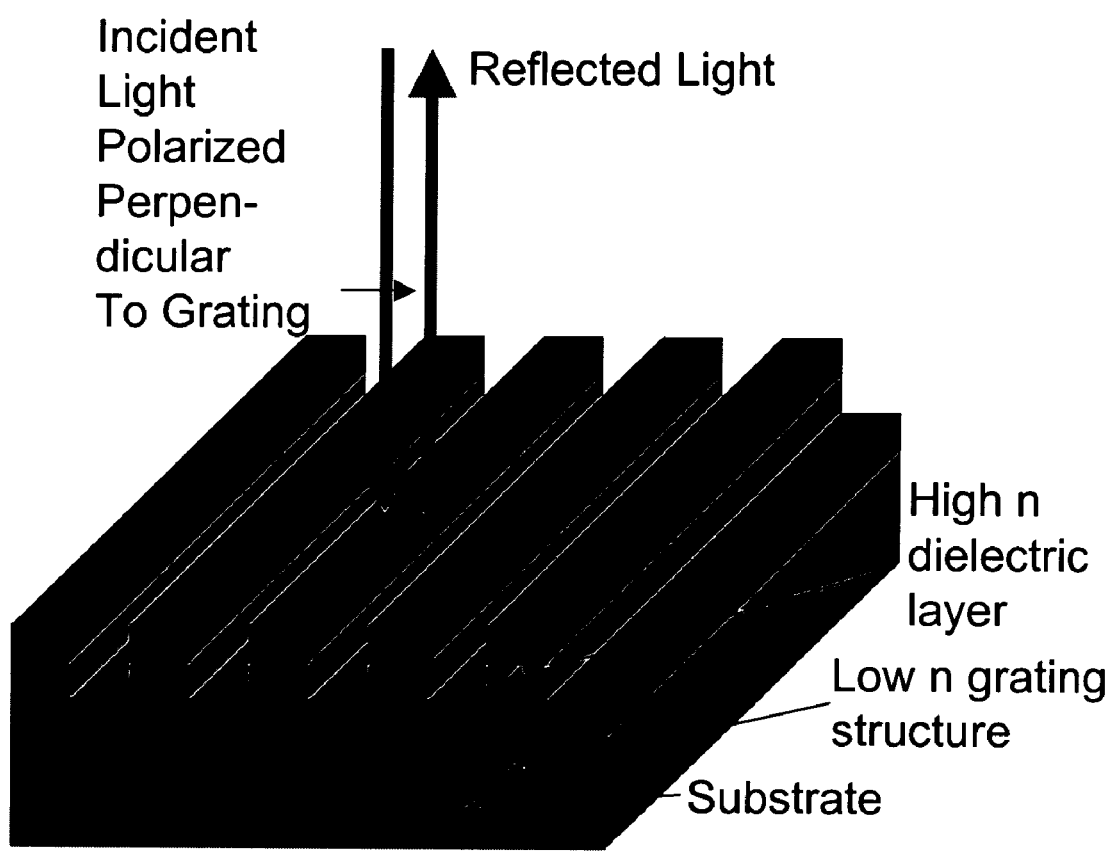
FIG. 2 shows an embodiment of a colorimetric resonant reflection biosensor comprising a one-dimensional grating made according to the methods and compositions of the invention.
Figure 3A:
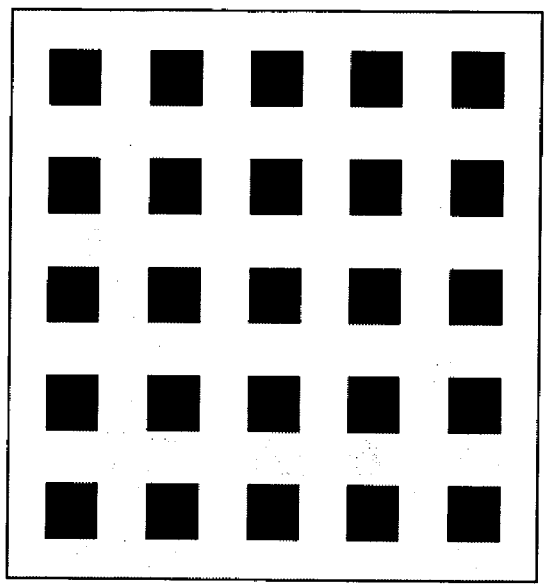
FIG. 3A-B shows a grating comprising a rectangular grid of squares (FIG. 3A) or holes (FIG. 3B).
Figure 3B:
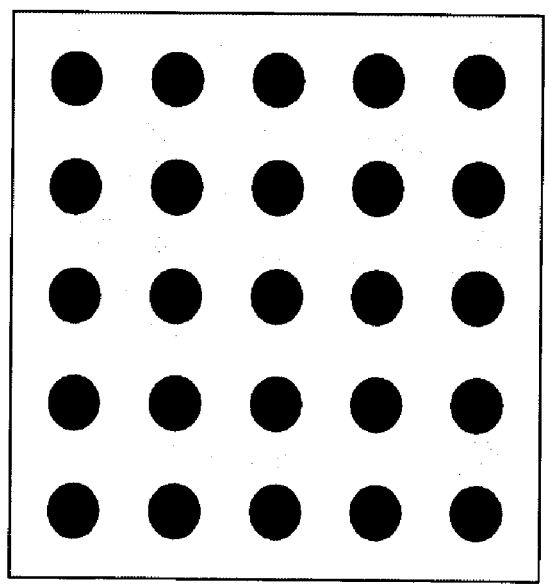

Linear gratings (i.e., one dimensional gratings) have resonant characteristics where the illuminating light polarization is oriented perpendicular to the grating period. A schematic diagram of one embodiment a linear grating structure with an optional cover layer is shown in FIG. 2. A colorimetric resonant reflection biosensor can also comprise, for example, a two-dimensional grating, e.g., a hexagonal array of holes (see FIG. 3B) or squares (see FIG. 3A). Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

Figure 4:
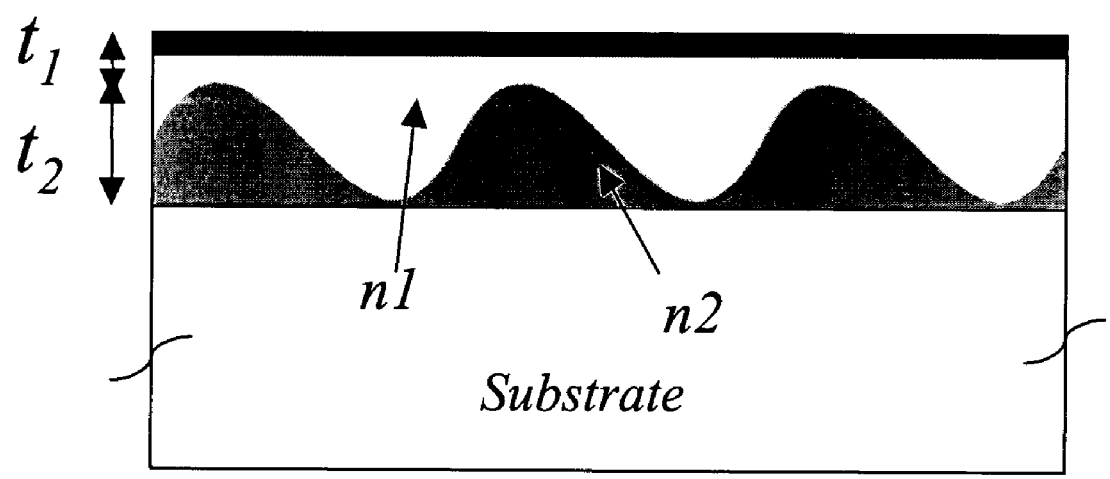
FIG. 4 shows a biosensor cross-section profile utilizing a sinusoidally varying grating profile.

It is also possible to make a resonant biosensor in which the high refractive index material is not stepped, but which varies with lateral position. FIG. 4 shows a profile in which the high refractive index material of the two-dimensional grating, $n_2$, is sinusoidally varying in height. To produce a resonant reflection at a particular wavelength, the period of the sinusoid is identical to the period of an equivalent stepped structure. The resonant operation of the sinusoidally varying structure and its functionality as a biosensor has been verified using GSOLVER (Grating Solver Development Company, Allen, Tex., USA) computer models.

A biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a biosensor of the invention will be illuminated with white light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

Figure 5:
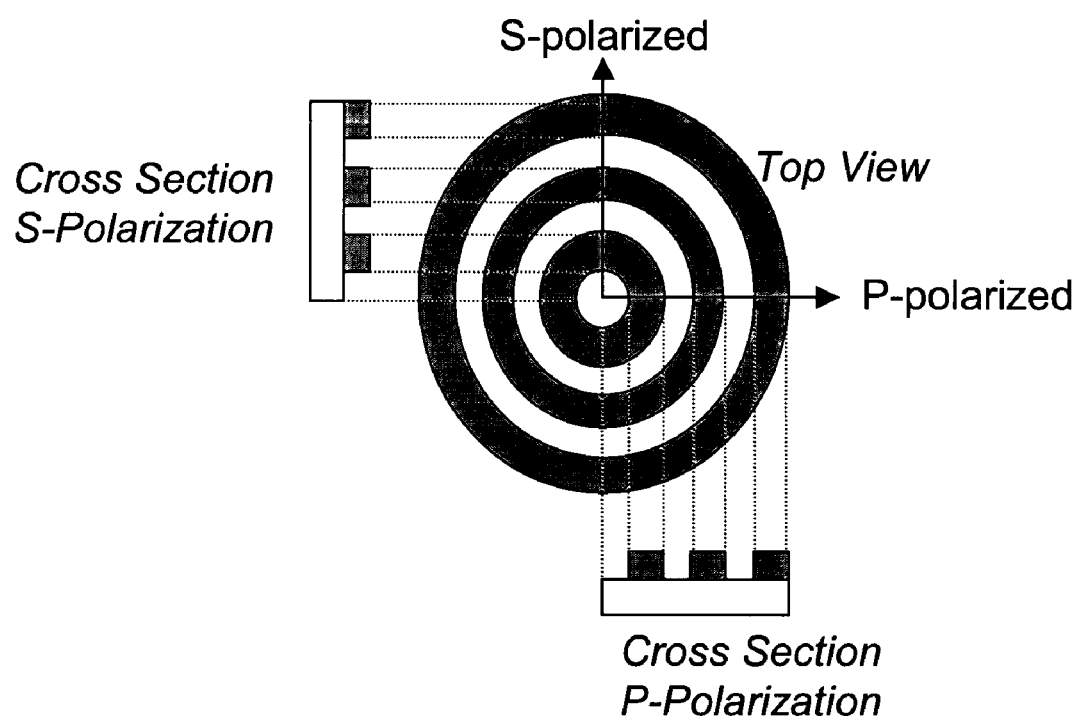
FIG. 5 shows a resonant reflection or transmission filter structure consisting of a set of concentric rings.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as an array spot or a microtiter plate well. Each separate microarray spot or microtiter plate well has a separate concentric ring pattern centered within it. See, e.g., FIG. 5. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

Figure 6:
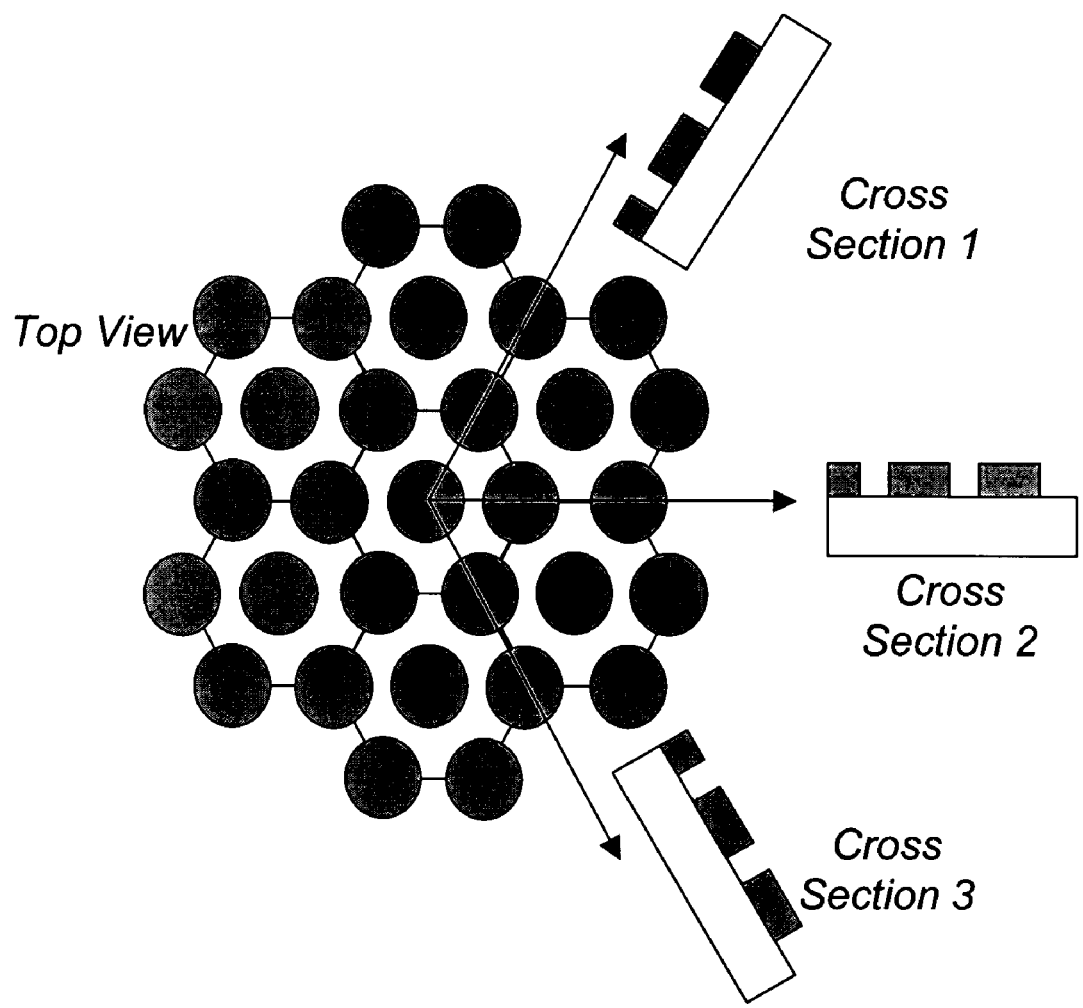
FIG. 6 shows a resonant reflective or transmission filter structure comprising a hexagonal grid of holes (or a hexagonal grid of posts) that closely approximates the concentric circle structure of FIG. 5 without requiring the illumination beam to be centered upon any particular location of the grid.

In another embodiment, an array of holes or posts are arranged to closely approximate the concentric circle structure described above without requiring the illumination beam to be centered upon any particular location of the grid. See e.g. FIG. 6. Such an array pattern is automatically generated by the optical interference of three laser beams incident on a surface from three directions at equal angles. In this pattern, the holes (or posts) are centered upon the corners of an array of closely packed hexagons as shown in FIG. 6. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

Another grating that can be produced using the methods of the invention is a volume surface-relief volume diffractive grating (a SRVD grating), also referred to as a three-dimensional grating. SRVD gratings have a surface that reflects predominantly at a particular narrow band of optical wavelengths when illuminated with a broad band of optical wavelengths. Where specific binding substances and/or binding partners are immobilized on a SRVD grating, producing a SRVD biosensor, the reflected narrow band of wavelengths of light is shifted. One-dimensional surfaces, such as thin film interference filters and Bragg reflectors, can select a narrow range of reflected or transmitted wavelengths from a broadband excitation source, however, the deposition of additional material, such as specific binding substances and/or binding partners onto their upper surface results only in a change in the resonance linewidth, rather than the resonance wavelength. In contrast, SRVD biosensors have the ability to alter the reflected wavelength with the addition of material, such as specific binding substances and/or binding partners to the surface. The depth and period of relief volume diffraction structures are less than the resonance wavelength of light reflected from a biosensor.

A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps.

Figure 7:
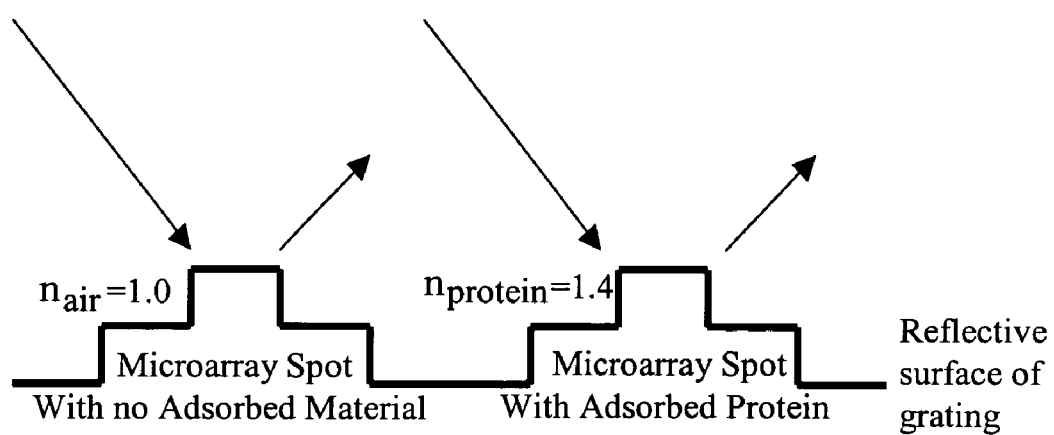
FIG. 7 shows a graphic representation of how adsorbed material, such as a protein monolayer, will increase the reflected wavelength of a biosensor that comprises a three-dimensional grating.

An example of a three-dimensional phase-quantized terraced surface relief pattern is a pattern that resembles a stepped pyramid. Each inverted pyramid is approximately 1 micron in diameter, preferably, each inverted pyramid can be about 0.5 to about 5 microns diameter, including for example, about 1 micron. The pyramid structures can be close-packed so that a typical microarray spot with a diameter of about 150-200 microns can incorporate several hundred stepped pyramid structures. The relief volume diffraction structures have a period of about 0.1 to about 1 micron and a depth of about 0.1 to about 1 micron. FIG. 7 demonstrates how individual microarray locations (with an entire microarray spot incorporating hundreds of pyramids now represented by a single pyramid for one microarray spot) can be optically queried to determine if specific binding substances or binding partners are adsorbed onto the surface. When the biosensor is illuminated with white light, pyramid structures without significant bound material will reflect wavelengths determined by the step height of the pyramid structure. When higher refractive index material, such as binding partners or specific binding substances, are incorporated over the reflective metal surface, the reflected wavelength is modified to shift toward longer wavelengths. The color that is reflected from the terraced step structure is theoretically given as twice the step height times the index of refraction of a reflective material that is coated onto the first surface of a sheet material of a SRVD biosensor. A reflective material can be, for example silver, aluminum, or gold.

One or more specific binding substances, as described above, are immobilized on the reflective material of a SRVD biosensor. One or more specific binding substances can be arranged in an array of one or more distinct locations, as described above, on the reflective material.

Because the reflected wavelength of light from a SRVD biosensor is confined to a narrow bandwidth, very small changes in the optical characteristics of the surface manifest themselves in easily observed changes in reflected wavelength spectra. The narrow reflection bandwidth provides a surface adsorption sensitivity advantage compared to reflectance spectrometry on a flat surface.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific binding substances are bound to their respective binding partners, due to optical interference.

Readout of the reflected color can be performed serially by focusing a microscope objective onto individual microarray spots and reading the reflected spectrum, or in parallel by, for example, projecting the reflected image of the microarray onto a high resolution color CCD camera.

In one embodiment of the invention, an optical device is provided. An optical device comprises a structure similar to a biosensor of the invention; however, an optical device does not comprise one of more binding substances immobilized on the grating. An optical device can be used as, for example, a narrow band optical filter.

Specific Binding Substances and Binding Partners

One or more specific binding substances are immobilized on the one- or two- or three-dimensional grating or cover layer, if present, by for example, physical adsorption or by chemical binding. A specific binding substance can be, for example, a nucleic acid, peptide, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, cell, virus, bacteria, polymer or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid. The polymer is selected from the group of long chain molecules with multiple active sites per molecule consisting of hydrogel, dextran, poly-amino acids and derivatives thereof, including poly-lysine (comprising poly-l-lysine and poly-d-lysine), poly-phe-lysine and poly-glu-lysine.

Preferably, one or more specific binding substances are arranged in an array of one or more distinct locations on a biosensor. An array of specific binding substances comprises one or more specific binding substances on a surface of a biosensor of the invention such that a surface contains many distinct locations, each with a different specific binding substance or with a different amount of a specific binding substance. For example, an array can comprise 1, 10, 100, 1,000, 10,000 or 100,000 distinct locations. Such a biosensor surface is called an array because one or more specific binding substances are typically laid out in a regular grid pattern in x-y coordinates. However, an array of the invention can comprise one or more specific binding substance laid out in any type of regular or irregular pattern. For example, distinct locations can define an array of spots of one or more specific binding substances. An array spot can be about 50 to about 500 microns in diameter. An array spot can also be about 150 to about 200 microns in diameter. One or more specific binding substances can be bound to their specific binding partners.

An array on a biosensor of the invention can be created by placing microdroplets of one or more specific binding substances onto, for example, an x-y grid of locations on a grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, peptide, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, cell, virus, bacteria, polymer or biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatic fluid.

One example of an array of the invention is a nucleic acid array, in which each distinct location within the array contains a different nucleic acid molecule. In this embodiment, the spots within the nucleic acid microarray detect complementary chemical binding with an opposing strand of a nucleic acid in a test sample.

While microtiter plates are the most common format used for biochemical assays, microarrays are increasingly seen as a means for maximizing the number of biochemical interactions that can be measured at one time while minimizing the volume of precious reagents. By application of specific binding substances with a microarray spotter onto a biosensor of the invention, specific binding substance densities of 10,000 specific binding substances/in$^2$ can be obtained. By focusing an illumination beam to interrogate a single microarray location, a biosensor can be used as a label-free microarray readout system.

Further, both the microarray and microtiter plate embodiments can be combined such that one or more specific binding substances are arranged in an array of one or more distinct locations on the sensor surface, said surface residing within one or more wells of the microtiter plate and comprising one or more surfaces of the microtiter plate, preferably the bottom surface. The array of specific binding substances comprises one or more specific binding substances on the sensor surface within a microtiter plate well such that a surface contains one or more distinct locations, each with a different specific binding substance or with a different amount of a specific binding substance. For example, an array can comprise 1, 10, 100, 1,000, 10,000 or 100,000 distinct locations. Thus, each well of the microtiter plate embodiment can have within it an array of one or more distinct locations separate from the other wells of the microtiter plate embodiment, which allows multiple different samples to be processed on one microtiter plate of the invention, one or more samples for each separate well. The array or arrays within any one well can be the same or different than the array or arrays found in any other microtiter wells of the same microtiter plate.

Immobilization or One or More Specific Binding Substances

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific binding substances can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of specific binding substances on a biosensor surface and provide defined orientation and conformation of the surface-bound molecules.

Several examples of chemical binding of specific binding substances to a biosensor of the invention appear in Example 2, below. Other types of chemical binding include, for example, binding via the following functional groups: an amine group, aldehyde group, nickel group, acid group, alkane group, alkene group, alkyne group, aromatic group, alcohol group, ether group, ketone group, ester group, amide group, amino acid group, nitro group, nitrile group, carbohydrate group, thiol group, organic phosphate group, lipid group, phospholipid group or steroid group. These surfaces can be used to attach several different types of chemical linkers to a biosensor surface, as shown in FIG. 8. For example, an amine surface can be used to attach several types of linker molecules while an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Immobilization of specific binding substances to plastic, epoxy, or high refractive index material can be performed essentially as described for immobilization to glass. However, the acid wash step can be eliminated where such a treatment would damage the material to which the specific binding substances are immobilized.

For the detection of binding partners at concentrations less than about ~0.1 ng/ml, it is preferable to amplify and transduce binding partners bound to a biosensor into an additional layer on the biosensor surface. The increased mass deposited on the biosensor can be easily detected as a consequence of increased optical path length. By incorporating greater mass onto a biosensor surface, the optical density of binding partners on the surface is also increased, thus rendering a greater resonant wavelength shift than would occur without the added mass. The addition of mass can be accomplished, for example, enzymatically, through a "sandwich" assay, or by direct application of mass to the biosensor surface in the form of appropriately conjugated beads or polymers of various size and composition. This principle has been exploited for other types of optical biosensors to demonstrate sensitivity increases over 1500 x beyond sensitivity limits achieved without mass amplification. See, e.g., Jenison et al., "Interference-based detection of nucleic acid targets on optically coated silicon," Nature Biotechnology, 19: 62-65, 2001.

Figure 9A:
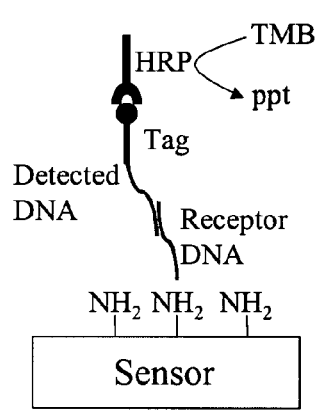
FIG. 9A-C shows methods that can be used to amplify the mass of a binding partner such as detected DNA or detected protein on the surface of a biosensor.

As an example, FIG. 9A shows that an $NH_2$-activated biosensor surface can have a specific binding substance comprising a single-strand DNA capture probe immobilized on the surface. The capture probe interacts selectively with its complementary target binding partner. The binding partner, in turn, can be designed to include a sequence or tag that will bind a "detector" molecule. As shown in FIG. 9A, a detector molecule can contain, for example, a linker to horseradish peroxidase (HRP) that, when exposed to the correct enzyme, will selectively deposit additional material on the biosensor only where the detector molecule is present. Such a procedure can add, for example, 300 angstroms of detectable biomaterial to the biosensor within a few minutes.

Figure 9B:
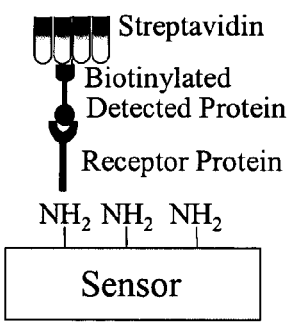

A "sandwich" approach can also be used to enhance detection sensitivity. In this approach, a large molecular weight molecule can be used to amplify the presence of a low molecular weight molecule. For example, a binding partner with a molecular weight of, for example, about 0.1 kDa to about 20 kDa, can be tagged with, for example, succinimidyl-6-[a-methyl-a-(2-pyridyl-dithio) toluamido] hexanoate (SMPT), or dimethylpimelimidate (DMP), histidine, or a biotin molecule, as shown in FIG. 9B. Where the tag is biotin, the biotin molecule will binds strongly with streptavidin, which has a molecular weight of 60 kDa. Because the biotin/streptavidin interaction is highly specific, the streptavidin amplifies the signal that would be produced only by the small binding partner by a factor of 60.

Figure 9C:
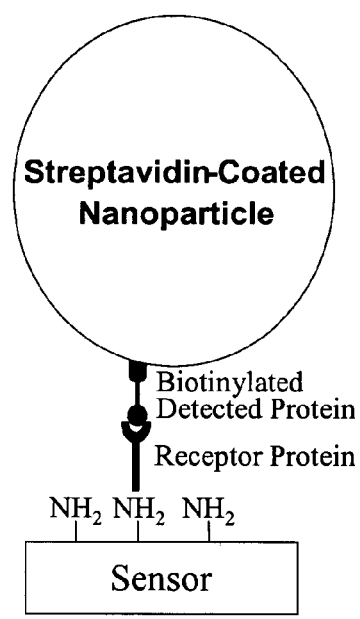

Detection sensitivity can be further enhanced through the use of chemically derivatized small particles. "Nanoparticles" made of colloidal gold, various plastics, or glass with diameters of about 3-300 nm can be coated with molecular species that will enable them to covalently bind selectively to a binding partner. For example, as shown in FIG. 9C, nanoparticles that are covalently coated with streptavidin can be used to enhance the visibility of biotin-tagged binding partners on the biosensor surface. While a streptavidin molecule itself has a molecular weight of 60 kDa, the derivatized bead can have a molecular weight of any size, including, for example, 60 KDa. Binding of a large bead will result in a large change in the optical density upon the biosensor surface, and an easily measurable signal. This method can result in an approximately 1000 x enhancement in sensitivity resolution.

Liquid-Containing Vessels

Figures 32A, 32B:
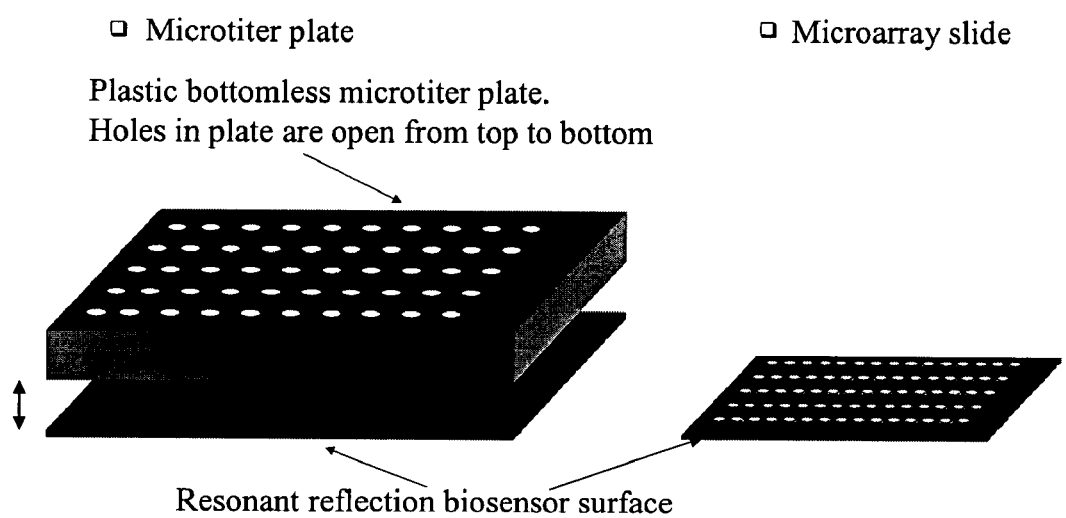
FIG. 32A-B shows two biosensor formats that can incorporate a colorimetric resonant reflectance biosensor.

A grating of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a biosensor that is incorporated into any type of microtiter plate. For example, a biosensor can be incorporated into the bottom surface of a microtiter plate by assembling the walls of the reaction vessels over the resonant reflection surface, as shown in FIG. 32A and 32B, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor or grating of the invention to the bottom surface of bottomless microtiter plates can be used, including, for example, adhesive attachment, ultrasonic welding, and laser welding.

The most common assay formats for pharmaceutical high-throughput screening laboratories, molecular biology research laboratories, and diagnostic assay laboratories are microtiter plates. The plates are standard-sized plastic cartridges that can contain about 2, 6, 8, 24, 48, 96, 384, 1536 or 3456 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. See, e g., FIG. 32A. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Methods of Using Biosensors

Biosensors of the invention can be used to study one or a number of specific binding substance/binding partner interactions in parallel. Binding of one or more specific binding substances to their respective binding partners can be detected, without the use of labels, by applying one or more binding partners to a biosensor that have one or more specific binding substances immobilized on their surfaces. A biosensor is illuminated with light and a maxima in reflected wavelength, or a minima in transmitted wavelength of light is detected from the biosensor. If one or more specific binding substances have bound to their respective binding partners, then the reflected wavelength of light is shifted as compared to a situation where one or more specific binding substances have not bound to their respective binding partners. Where a biosensor is coated with an array of one or more distinct locations containing the one or more specific binding substances, then a maxima in reflected wavelength or minima in transmitted wavelength of light is detected from each distinct location of the biosensor.

Figure 14:
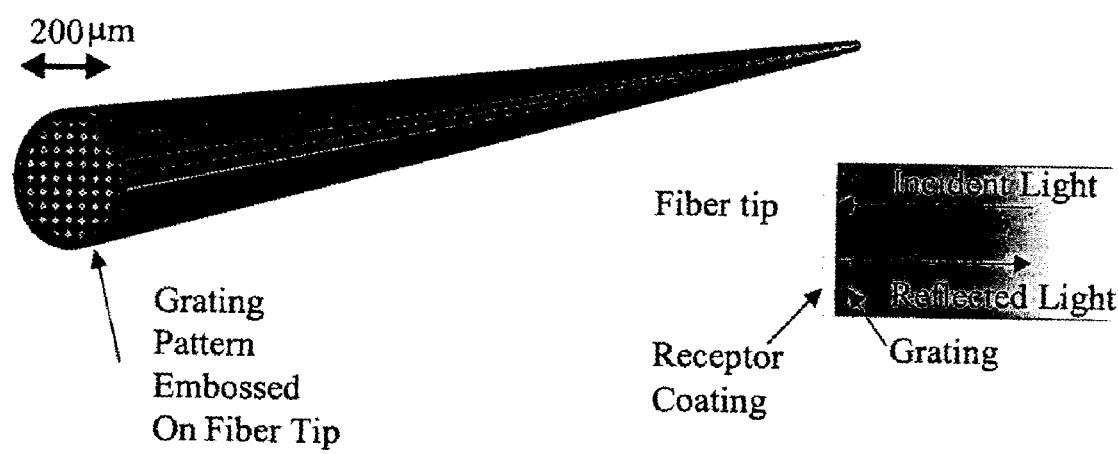
FIG. 14 demonstrates an example of a biosensor that occurs on the tip of a fiber probe for in vivo detection of biochemical substances.
Figure 15:
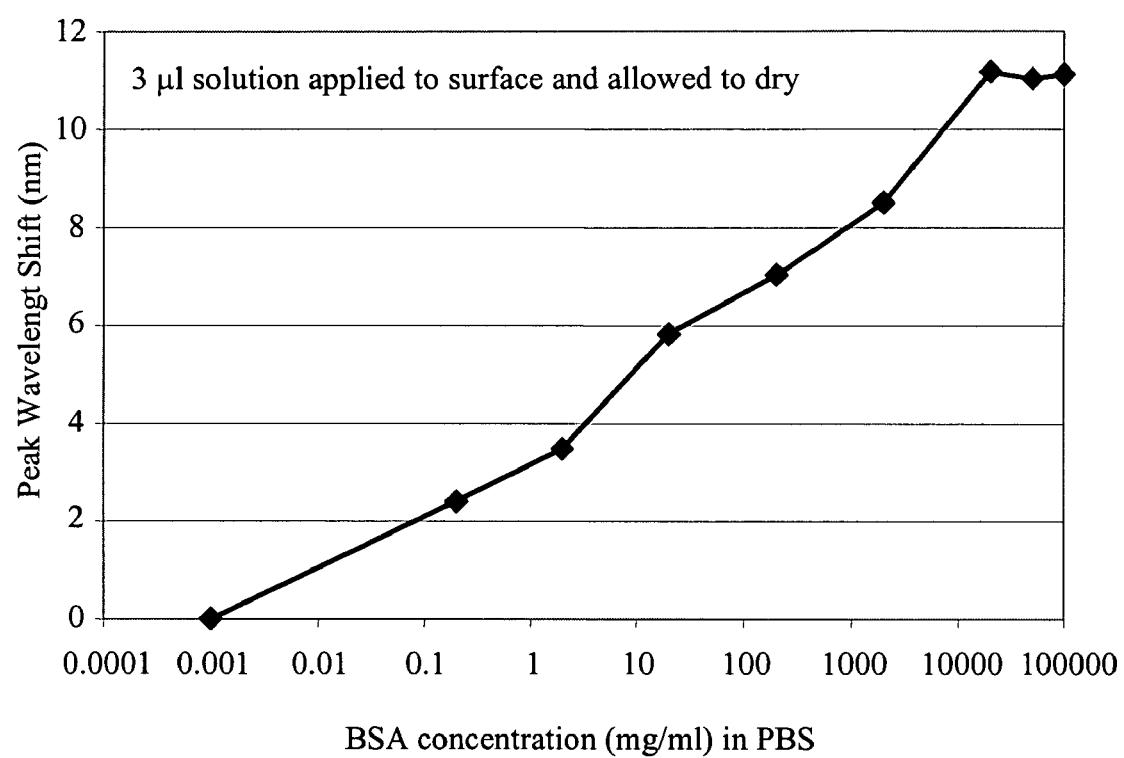
FIG. 15 shows dependence of peak resonance wavelength on the concentration of BSA dissolved in PBS, which was then allowed to dry on a biosensor surface.
Figure 31:
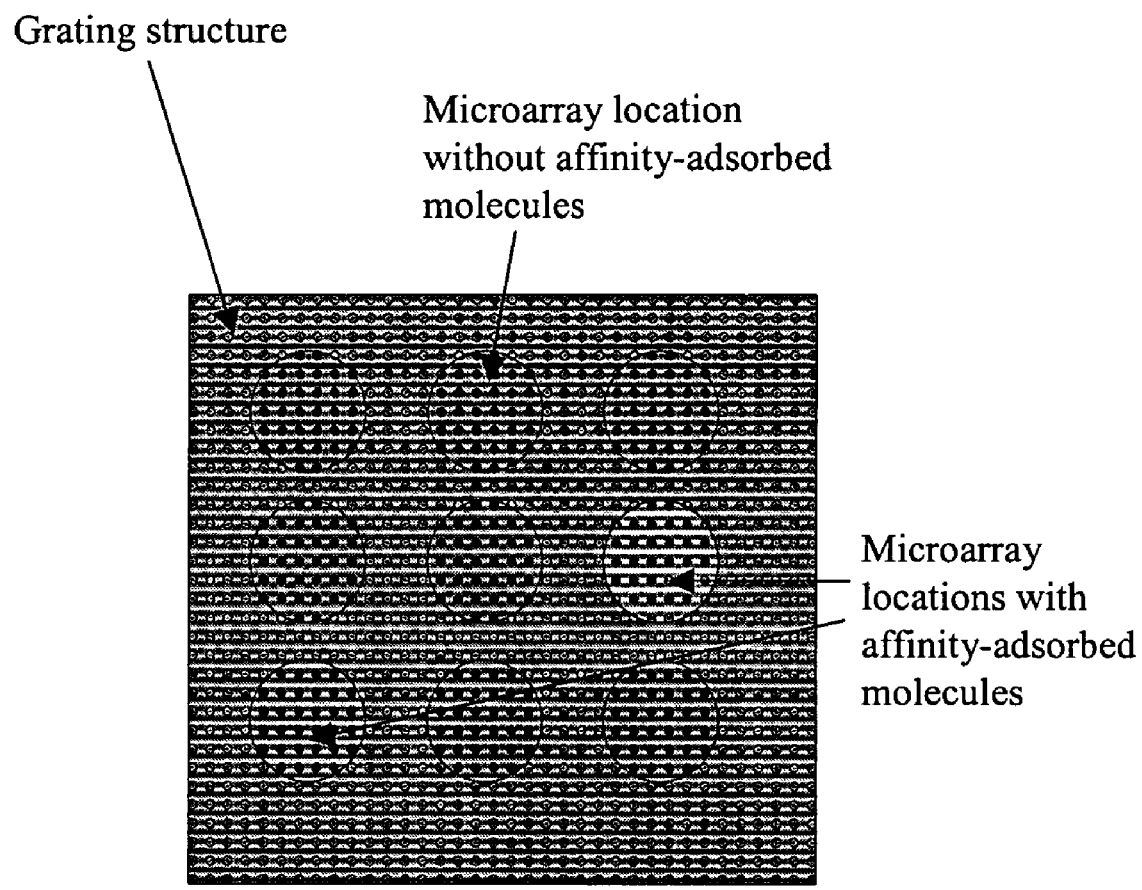
FIG. 31 shows an example of a biosensor used as a microarray.
Figure 33:
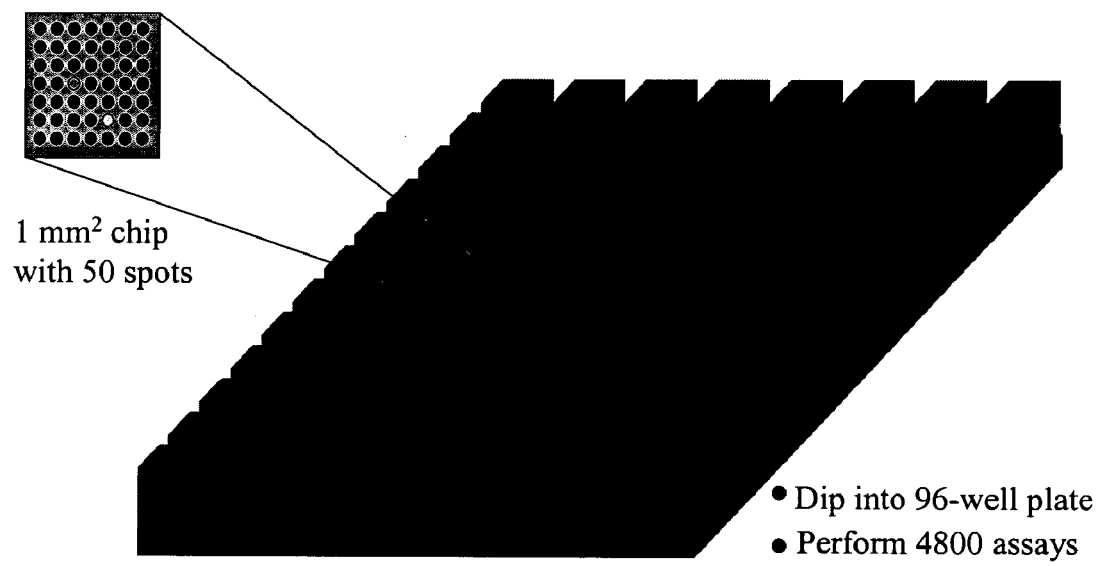
FIG. 33 shows an array of arrays concept for using a biosensor platform to perform assays with higher density and throughput.

In one embodiment of the invention, a variety of specific binding substances, for example, antibodies, can be immobilized in an array format onto a biosensor of the invention. See, e.g., FIG. 31. The biosensor is then contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay; however, the use of an enzyme or fluorescent label is not required. For high-throughput applications, biosensors can be arranged in an array of arrays, wherein several biosensors comprising an array of specific binding substances are arranged in an array. See, e.g., FIG. 33. Such an array of arrays can be, for example, dipped into microtiter plate to perform many assays at one time. In another embodiment, a biosensor can occur on the tip of a fiber probe for in vivo detection of biochemical substance. See, FIG. 14.

The activity of an enzyme can be detected by applying one or more enzymes to a biosensor to which one or more specific binding substances have been immobilized. The biosensor is washed and illuminated with light. The reflected wavelength of light is detected from the biosensor. Where the one or more enzymes have altered the one or more specific binding substances of the biosensor by enzymatic activity by, for example, cleaving all or a portion of a specific binding substance from the surface of a biosensor the reflected wavelength of light is shifted.

Another embodiment of the invention is a method of detecting cleavage of one or more entire specific binding substances from a surface of a colorimetric resonant reflectance optical biosensor. The method involves immobilizing one or more binding substances onto the surface of the calorimetric resonant reflectance optical biosensor at a distinct location, detecting a PWV of the distinct location, applying one or more cleaving molecules, detecting a PWV of the distinct location and comparing the initial PWV with the subsequent PWV. The cleavage of one or more entire specific binding substances is detected, and a peak wavelength value (PWV) is a relative measure of the specific binding substance that is bound to the biosensor. A cleaving molecule is a molecule that can cleave another molecule. For example, a cleaving molecule can be an enzyme such as a proteases, lipases, nucleases, lyases, peptidases, hydrolases, ligases, kinases and phosphatases.

A colorimetric resonant reflectance optical biosensor can comprise an internal surface of a microtiter well, a microtiter plate, a test tube, a petri dish or a microfluidic channel. Immobilization of the specific binding substance can be affected via binding to, for example, the following functional groups: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Further, the specific binding substance is immobilized on the surface of the colorimetric resonant reflectance optical biosensor via physical adsorption, chemical binding, electrochemical binding, electrostatic binding, hydrophobic binding or hydrophilic binding.

One or more specific binding substances can be arranged in an array of one or more distinct locations on the surface of the biosensor. The one or more distinct locations can define microarray spots of about 50-500 microns, or about 150-200 microns in diameter.

The method described above, that of detecting cleavage of one or more entire specific binding substances from a surface of a colorimetric resonant reflectance optical biosensor, can also comprise alternative steps. One or more specific binding substances can be immobilized in one or more distinct locations defining an array within a well of a microtiter plate. The one or more distinct locations defining the microarray can be located upon the surface of a calorimetric resonant reflectance optical biosensor, which, in turn, comprises an internal surface of a well. A PWV is detected for one or more distinct locations within the well. One or more cleaving molecules are applied to the well. Detection of a PWV for one or more distinct locations within the well is performed. The initial PWV and the subsequent PWV are compared. The cleavage of one or more entire specific binding substances at the one or more distinct locations within the well is detected. A peak wavelength value (PWV) is a relative measure of the specific binding substance that is bound to the biosensor.

Another embodiment of the invention provides a method of detecting how effectively a molecule inhibits the activity of an enzyme or binding partner, i.e., "inhibition activity" of the molecule. In one embodiment, is adding one or more molecules suspected of having inhibition activity are added to a biosensor to which one or more specific binding substances are attached, followed by the addition of one or more enzymes known to act upon the specific binding substances. For example, a protease, lipase, nuclease, lyase, peptidase, hydrolase, ligase, kinase, phosphatase, or any other type of enzyme that would produce a detectable change in a specific binding substance. The enzyme can effect a specific binding partner by, for example, cleaving substantially the entire single binding substance or a portion of the single binding substance from the biosensor. One or more binding partners known to bind to one or more specific binding substances immobilized on the biosensor can also be added to the biosensor.

A molecule with no inhibition activity allows the enzyme activity to occur unabated; a molecule with substantially complete inhibition activity halts the reaction substantially completely; and a molecule with partial inhibition halts the reaction partially. Additionally, a molecule with no inhibition activity allows a binding partner to bind to its specific binding substance. A molecule with partial inhibition allows partial or weak binding of the binding partner to its specific binding substance partner. A molecule with inhibition activity inhibits the binding of the binding partner to its specific binding partner. Thus, the method provides a technique of detecting inhibition activity of one or more molecules against enzymes or binding partners.

Detecting a PWV of one or more distinct locations is followed by applying one or more molecules suspected of having inhibition activity to the one or more distinct locations and applying one or more enzymes or binding partners to the distinct locations. The PWV of the one or more distinct locations is detected and compared to the initial PWV. Alternatively, the one or more molecules suspected of having inhibition activity can be mixed with the one or more enzymes or binding partners, which, together, can be applied to the one or more distinct locations. A decrease or increase in the initial PWV above in relation to the subsequent PWV above is (1) a relative measure of the proportion of binding substance that is altered by the enzyme or the amount of binding partners bound to the biosensor from the biosensor surface or (2) a measure of relative effectiveness of one or more molecules suspected of having inhibition activity.

The method described above, that of detecting inhibition activity of one or more molecules against enzymes or binding partners can also comprise alternative steps. For example, one or more specific binding substances can be immobilized in one or more distinct locations defining an array within a well of a microtiter plate or other liquid holding device. The one or more distinct locations defining an array are located upon the surface of a colorimetric resonant reflectance optical biosensor which comprises an internal surface of the well. Detecting a PWV for the one or more distinct locations within the well is followed by applying one or more molecules suspected of having inhibition activity to the well. One or more enzymes or binding partners are applied to the well and a PWV is detected for the one or more distinct locations within the well. The initial PWV is compared with the subsequent PWV and reveals the inhibition activity of one or more molecules against enzymes or binding partners at each distinct location within a well. Alternatively, the one or more molecules suspected of having inhibition activity can be mixed with the one or more enzymes or binding partners, which, together, can be applied to the well.

Additionally, a test sample, for example, cell lysates containing binding partners, can be applied to a biosensor of the invention, followed by washing to remove unbound material. The binding partners that bind to a biosensor can be eluted from the biosensor and identified by, for example, mass spectrometry. Optionally, a phage DNA display library can be applied to a biosensor of the invention followed by washing to remove unbound material. Individual phage particles bound to the biosensor can be isolated and the inserts in these phage particles can then be sequenced to determine the identity of the binding partner.

Another embodiment of the invention provides a method of detecting cell migration and chemotaxis. In particular, cells can be grown on one end of a colorimetric resonant reflectance optical biosensor, either within a well or in an array format. The end of the biosensor containing the cells can optionally be segregated, via the use of semi-permeable membranes, from the opposing end where the chemotactic agent is placed. Detection systems comprised of an imaging spectrometer, or alternatively a fiber optic probe that can be moved to read from multiple locations of the biosensor, can then be used to detect the location of the cells, and in turn permit the computation of the cell migration velocity.

A further embodiment of the invention provides a method of detecting a change in cell growth patterns. Briefly, cells can be grown on a colorimetric resonant reflectance optical biosensor; a PWV detected; a test reagent applied to the cells; a PWV detected; and the initial PWV with the subsequent PWV can be compared, wherein the difference between the initial PWV in relation to the subsequent PWV indicates a change in cell growth patterns. A difference in PWV correlates with a change in a cell growth pattern.

The change in cell growth pattern can be selected from the group consisting of cell morphology, cell adhesion, cell migration, cell proliferation and cell death. One type of prokaryotic or eukaryotic cells or two or more types of eukaryotic or prokaryotic cells can be grown on the biosensor. The biosensor can comprise an internal surface of a vessel selected from the group consisting of a microtiter well, microtiter plate, test tube, petri dish and microfluidic channel.

A still further embodiment of the invention provides a method of detecting molecules released from cells grown in a semi-permeable internal sleeve held in contact with a calorimetric resonant reflectance optical biosensor. The semi-permeable internal sleeve can be, for example, a removable porous or non-removable porous insert that is held in contact with or close to the surface of a biosensor, wherein the sleeve is permeable to molecules secreted from the cells cultured on its surface and wherein the sleeve is impermeable to whole cells. A sleeve can fit into the wells of a microtiter plate or other vessel wherein a biosensor of the invention comprises an internal surface of the wells or other vessel.

This method can comprise the following steps: immobilizing one or more specific binding substances onto a surface of the calorimetric resonant reflectance optical biosensor at one or more distinct locations; detecting a PWV of the one or more distinct locations; growing cells in the semi-permeable internal sleeve held in contact with the colorimetric resonant reflectance optical biosensor at the one or more distinct locations; detecting the PWV of the one or more distinct locations; and comparing the initial PWV with the subsequent PWV. The binding of molecules released from cells grown in the semi-permeable internal sleeve held in contact with the colorimetric resonant reflectance optical biosensor to the one or more specific binding substances is detected. Further, the initial PWV is a relative measure of the specific binding substance that is bound to the biosensor, and the difference between the initial PWV in relation to the subsequent PWV is a relative measure of the molecules released from cells grown in a semi-permeable internal sleeve that are bound to the specific binding substances. The semi-permeable internal sleeve is a removable porous or non-removable porous insert.

The method described above, that of detecting molecules released from cells grown in a semi-permeable internal sleeve held in contact with a colorimetric resonant reflectance optical biosensor can also comprise alternative steps. For example, one or more binding substance can be immobilized in one or more distinct locations defining an array within a well of a microtiter plate, wherein the calorimetric resonant reflectance optical biosensor comprises an internal surface of the well. Detecting a PWV for the one or more distinct locations defining an array within the well is followed by growing cells in a semi-permeable internal sleeve held in contact with the well. The final steps are detecting the PWV for the one or more distinct locations within the well and comparing the initial PWV with the subsequent PWV. The difference between the initial PWV in relation to the subsequent PWV indicates the relative binding of one or more molecules secreted from the cells growing on the semi-permeable internal sleeve within a well to the one or more specific binding substances immobilized at one or more distinct locations within the well on the surface of a colorimetric resonant reflectance optical biosensor.

The ability to detect the binding of binding partners to specific binding substances, optionally followed by the ability to detect the removal of substantially entire or partial bound specific binding substances, from one or more distinct locations of the biosensor is an important aspect of the invention. Biosensors of the invention are also capable of detecting and quantifying the amount of a binding partner from a sample that is bound to one or more distinct locations defining an array by measuring the shift in reflected wavelength of light. For example, the wavelength shift at one or more distinct locations can be compared to positive and negative controls at other distinct locations to determine the amount of a specific binding substance that is bound. Importantly, numerous such one or more distinct locations can be arranged on the biosensor surface, and the biosensor can comprise an internal surface of a vessel such as an about 2, 6, 8, 24, 48, 96, 384, 1536 or 3456 well-microtiter plate. As an example, where 96 biosensors are attached to a holding fixture and each biosensor comprises about 100 distinct locations, about 9600 biochemical assays can be performed simultaneously.

Therefore, unlike methods for assays for surface plasmon resonance, resonant mirrors, and waveguide biosensors, the described methods enable many thousands of individual binding reactions to take place simultaneously upon the resonant optical biosensor surface. Clearly, this technology is useful in applications where large numbers of biomolecular interactions are measured in parallel, particularly when molecular labels will alter or inhibit the functionality of the molecules under study. High-throughput screening of pharmaceutical compound libraries with protein targets, and microarray screening of protein-protein interactions for proteomics are examples of applications that require the sensitivity and throughput afforded by this approach.

Detection Systems

A detection system can comprise a biosensor a light source that directs light to the biosensor, and a detector that detects light reflected from the biosensor. In one embodiment, it is possible to simplify the readout instrumentation by the application of a filter so that only positive results over a determined threshold trigger a detection.

A light source can illuminate a biosensor from its top surface, i.e., the surface to which one or more specific binding substances are immobilized or from its bottom surface. By measuring the shift in resonant wavelength at each distinct location of a biosensor of the invention, it is possible to determine which distinct locations have binding partners bound to them. The extent of the shift can be used to determine the amount of binding partners in a test sample and the chemical affinity between one or more specific binding substances and the binding partners of the test sample.

A biosensor can be illuminated twice. The first measurement determines the reflectance spectra of one or more distinct locations of a biosensor array with one or more specific binding substances immobilized on the biosensor. The second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can control for small nonuniformities in a surface of a biosensor that can result in regions with slight variations in the peak resonant wavelength. This method can also control for varying concentrations or molecular weights of specific binding substances immobilized on a biosensor.

Computer simulation can be used to determine the expected dependence between a peak resonance wavelength and an angle of incident illumination. A biosensor as shown in FIG. 1 can be for purposes of demonstration. The substrate chosen was glass ($n_{substrate}$=1.50). The grating is an optical pattern of silicon nitride squares ($t_2$=180 nm, $n_2$=2.01 (n=refractive index), $k_2$=0.001 (k=absorption coefficient)) with a period of 510 nm, and a filling factor of 56.2% (i.e., 56.2% of the surface is covered with silicon nitride squares while the rest is the area between the squares). The areas between silicon nitride squares are filled with a lower refractive index material. The same material also covers the squares and provides a uniformly flat upper surface. For this simulation, a glass layer was selected ($n_1$=1.40) that covers the silicon nitride squares by $t_2$=100 nm.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination can be from any incidence and any polarization.

Figure 10:
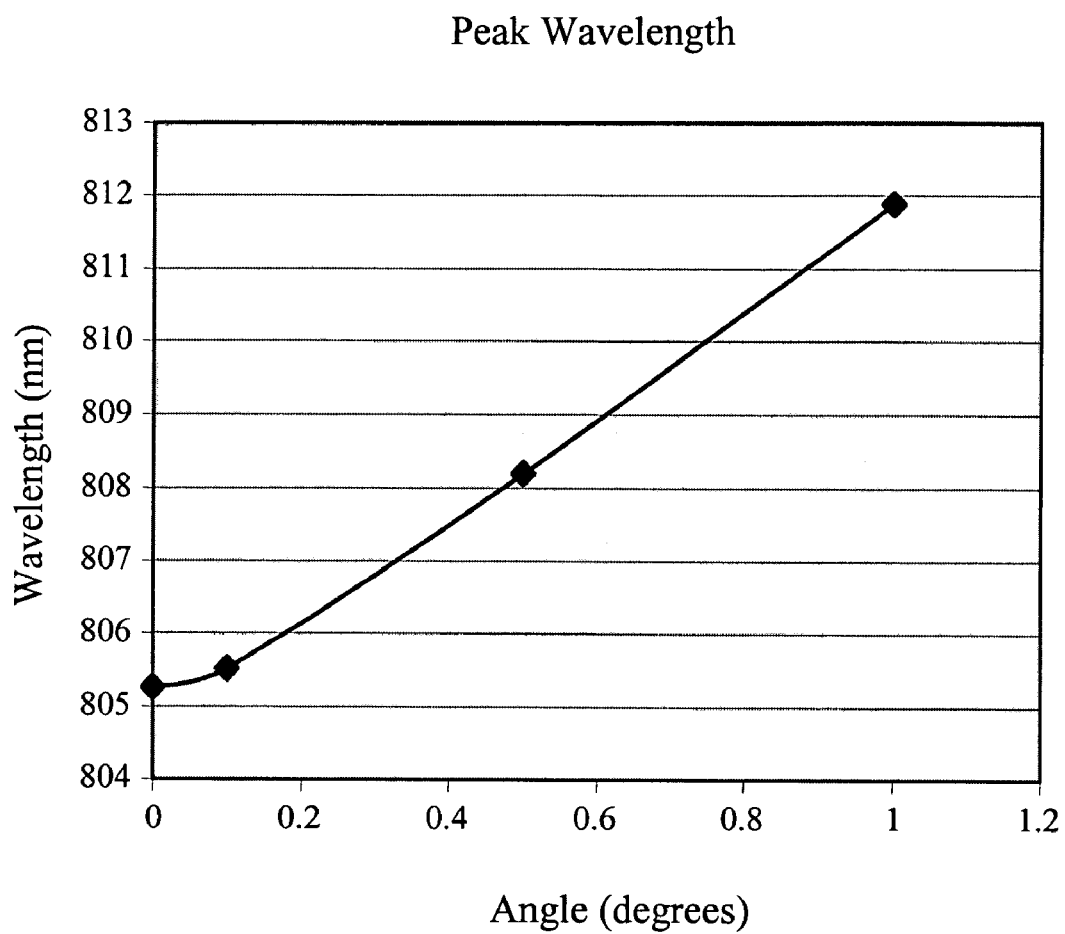
FIG. 10 shows resonance wavelength of a biosensor as a function of incident angle of detection beam.

FIG. 10 plots the dependence of the peak resonant wavelength upon the incident illumination angle. The simulation shows that there is a strong correlation between the angle of incident light, and the peak wavelength that is measured. This result implies that the collimation of the illuminating beam, and the alignment between the illuminating beam and the reflected beam will directly affect the resonant peak linewidth that is measured. If the collimation of the illuminating beam is poor, a range illuminating angles will be incident on the biosensor surface, and a wider resonant peak will be measured than if purely collimated light were incident.

Because the lower sensitivity limit of a biosensor is related to the ability to determine the peak maxima, it is important to measure a narrow resonant peak. Therefore, the use of a collimating illumination system with the biosensor provides for the highest possible sensitivity.

One type of detection system for illuminating the biosensor surface and for collecting the reflected light is a probe containing, for example, six illuminating optical fibers that are connected to a light source, and a single collecting optical fiber connected to a spectrometer. The number of fibers is not critical, any number of illuminating or collecting fibers are possible. The fibers are arranged in a bundle so that the collecting fiber is in the center of the bundle, and is surrounded by the six illuminating fibers. The tip of the fiber bundle is connected to a collimating lens that focuses the illumination onto the surface of the biosensor.

In this probe arrangement, the illuminating and collecting fibers are side-by-side. Therefore, when the collimating lens is correctly adjusted to focus light onto the biosensor surface, one observes six clearly defined circular regions-of-illumination, and a central dark region. Because the biosensor does not scatter light, but rather reflects a collimated beam, no light is incident upon the collecting fiber, and no resonant signal is observed. Only by defocusing the collimating lens until the six illumination regions overlap into the central region is any light reflected into the collecting fiber. Because only defocused, slightly uncollimated light can produce a signal, the biosensor is not illuminated with a single angle of incidence, but with a range of incident angles. The range of incident angles results in a mixture of resonant wavelengths due to the dependence shown in FIG. 10. Thus, wider resonant peaks are measured than might otherwise be possible.

Figure 11:
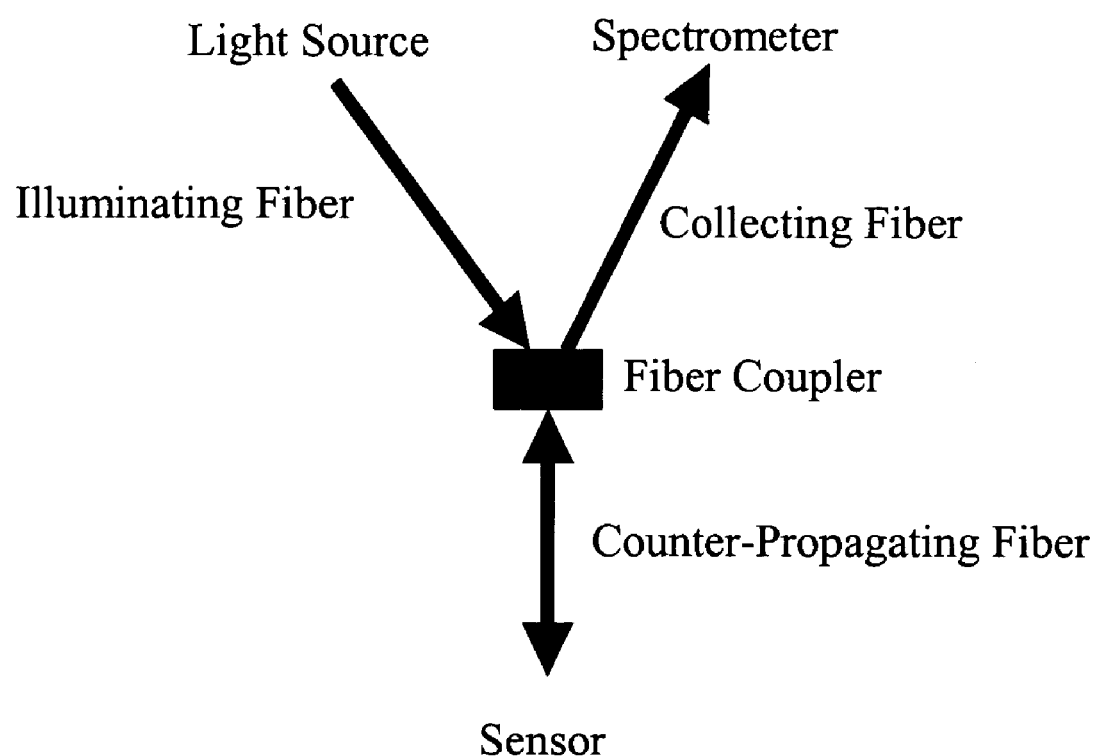
FIG. 11 shows an example of the use of two coupled fibers to illuminate and collect reflected light from a biosensor.

Therefore, it is desirable for the illuminating and collecting fiber probes to spatially share the same optical path. Several methods can be used to co-locate the illuminating and collecting optical paths. For example, a single illuminating fiber, which is connected at its first end to a light source that directs light at the biosensor, and a single collecting fiber, which is connected at its first end to a detector that detects light reflected from the biosensor, can each be connected at their second ends to a third fiber probe that can act as both an illuminator and a collector. The third fiber probe is oriented at a normal angle of incidence to the biosensor and supports counter-propagating illuminating and reflecting optical signals. An example of such a detection system is shown in FIG. 11.

Figure 12:
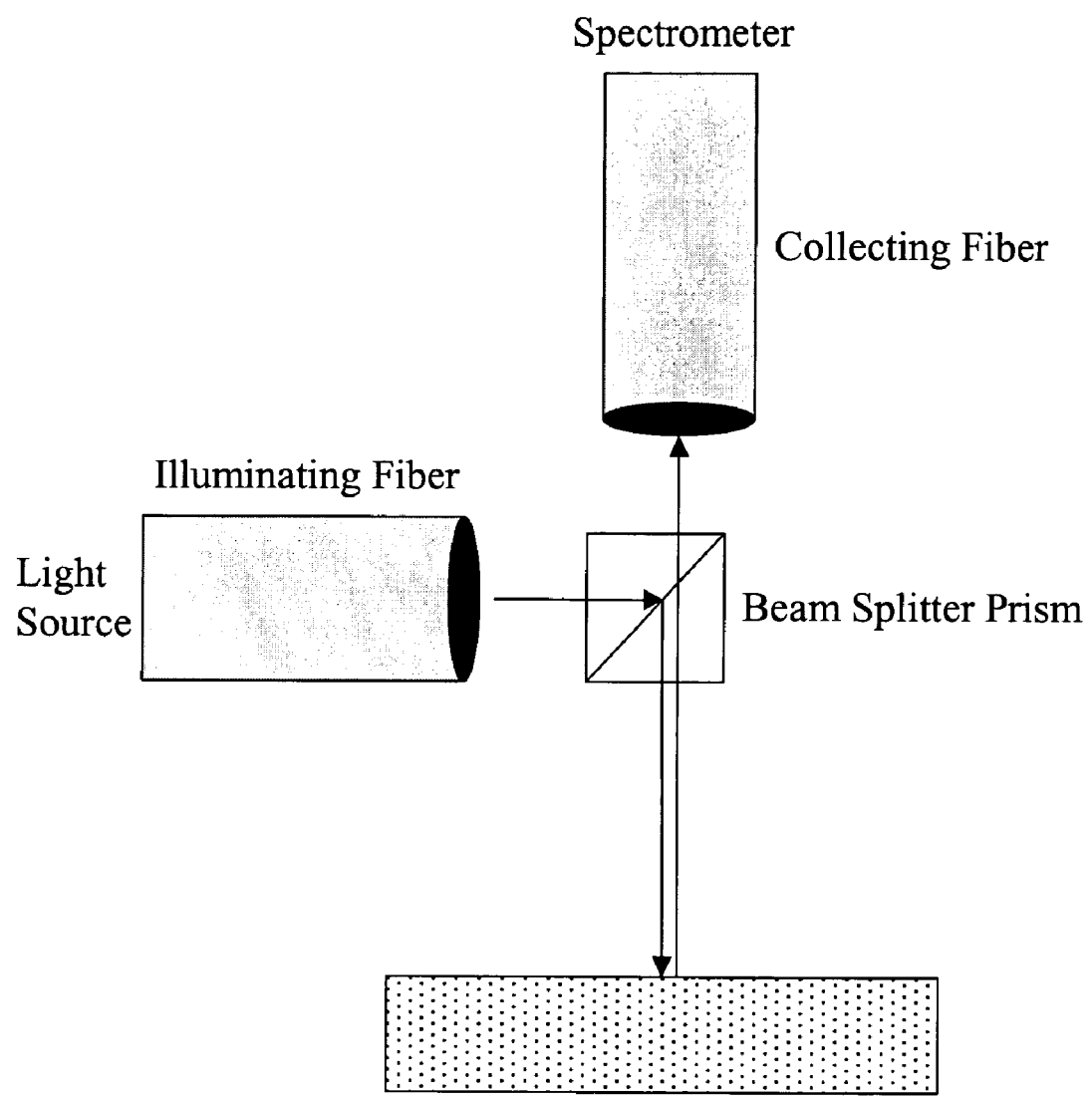
FIG. 12 shows an example of the use of a beam splitter to enable illuminating and reflected light to share a common collimated optical path to a biosensor.

Another method of detection involves the use of a beam splitter that enables a single illuminating fiber, which is connected to a light source, to be oriented at a 90 degree angle to a collecting fiber, which is connected to a detector. Light is directed through the illuminating fiber probe into the beam splitter, which directs light at the biosensor. The reflected light is directed back into the beam splitter, which directs light into the collecting fiber probe. An example of such a detection device is shown in FIG. 12. A beam splitter allows the illuminating light and the reflected light to share a common optical path between the beam splitter and the biosensor, so perfectly collimated light can be used without defocusing.

Angular Scanning

Detection systems of the invention are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

As shown in theoretical modeling and experimental data, the resonance peak wavelength is strongly dependent on the incident angle of the detection light beam. FIG. 10 depicts this dependence as modeled for a biosensor of the invention. Because of the angular dependence of the resonance peak wavelength, the incident white light needs to be well collimated. Angular dispersion of the light beam broadens the resonance peak, and reduces biosensor detection sensitivity. In addition, the signal quality from the spectroscopic measurement depends on the power of the light source and the sensitivity of the detector. In order to obtain a high signal-to-noise ratio, an excessively long integration time for each detection location can be required, thus lengthening overall time to readout a biosensor plate. A tunable laser source can be used for detection of grating resonance, but is expensive.

In one embodiment of the invention, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

Figure 13:
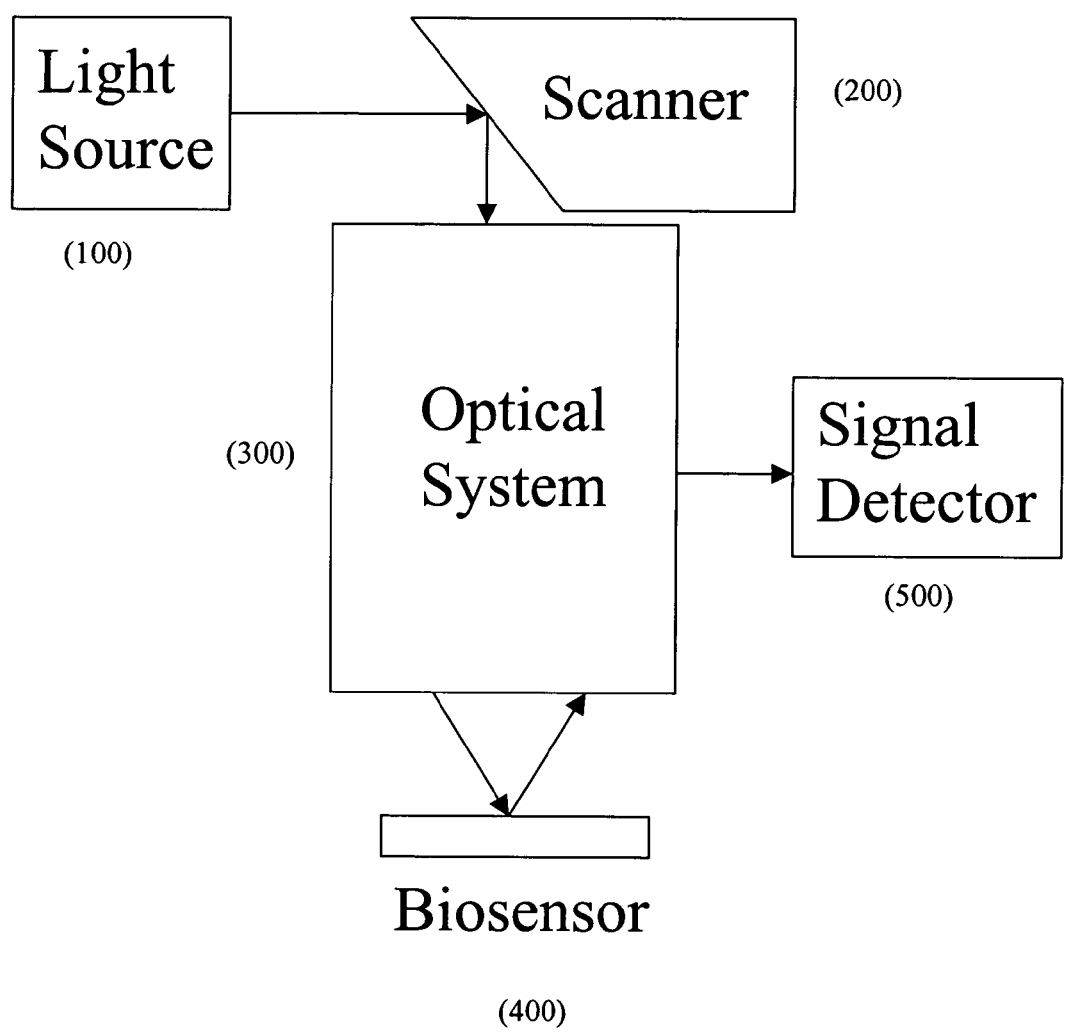
FIG. 13 shows a schematic diagram of a detection system.
Figure 30:
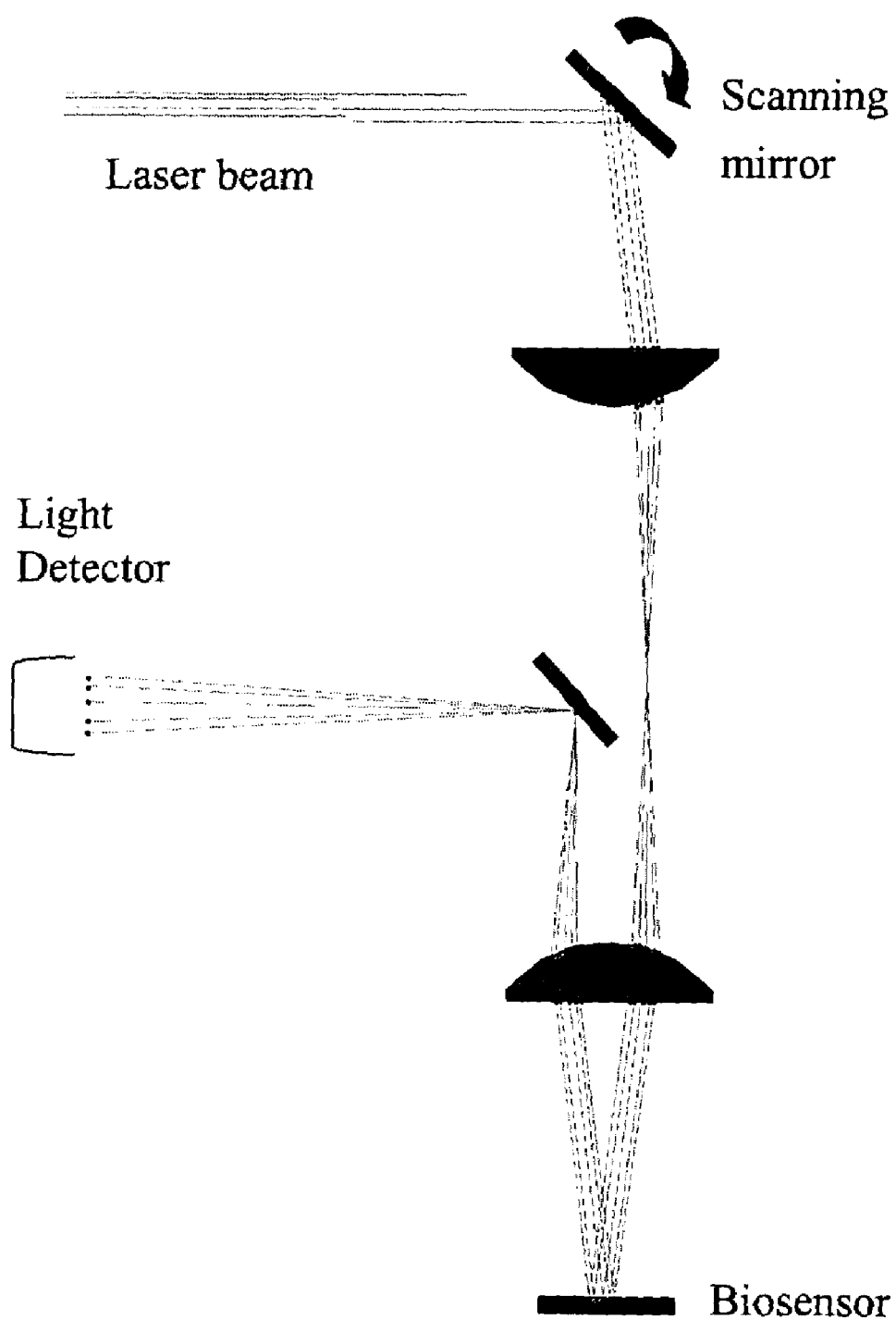
FIG. 30 shows an example of a system for angular scanning of a biosensor.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors. An example of such a detection system is shown in FIG. 13. A light source (300) provides light to a scanner device (400), which directs the light into an optical system (500). The optical system (500) directs light to a biosensor (600). Light is reflected from the biosensor (600) to the optical system (500), which then directs the light into a light signal detector (700). One embodiment of a detection system is shown in FIG. 30, which demonstrates that while the scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used. The example shown in FIG. 30 includes a simple optical system for angular scanning. It consists of a pair of lenses with a common focal point between them. The optical system can be designed to achieve optimized performance for laser collimation and collection of reflected light beam.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec. As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, *Optics Lett.*, 21:549 (1996)), will be covered by 10 data points, each of which corresponds to resolution of the detection system.

The advantages of such a detection system includes: excellent collimation of incident light by a laser beam, high signal-to-noise ratio due to high beam power of a laser diode, low cost due to a single element light detector instead of a spectrometer, and high resolution of resonance peak due to angular scanning.

Fiber Probe Biosensor

A biosensor of the invention can occur on the tip of a multi-mode fiber optic probe. This fiber optic probe allows for in vivo detection of biomarkers for diseases and conditions, such as, for example, cardiac artery disease, cancer, inflammation, and sepsis. A single biosensor element (comprising, for example, several hundred grating periods) can be fabricated into the tip of a fiber optic probe, or fabricated from a glass substrate and attached to the tip of a fiber optic probe. See FIG. 14. A single fiber is used to provide illumination and measure resonant reflected signal.

For example, a fiber probe structure similar to that shown in FIG. 11 can be used to couple an illuminating fiber and detecting fiber into a single counterpropagating fiber with a biosensor embedded or attached to its tip. The fiber optic probe is inserted into a mammalian body, for example, a human body. Illumination and detection of a reflected signal can occur while the probe is inserted in the body.

The following are provided for exemplification purpose only and are not intended to limit the scope of the invention described in broad terms above. All references cited in this disclosure are incorporated herein by reference.

EXAMPLE 1

Immobilized Protein Detection

In order to demonstrate a biosensor's ability to quantify biomolecules on its surface, droplets of BSA dissolved in $H_2O$ eat various concentrations were applied to a biosensor as shown in FIG. 1. The 3 µl droplets were allowed to dry in air, leaving a small quantity of BSA distributed over a ~2 mm diameter area. The peak resonant wavelength of each biosensor location was measured before and after droplet deposition, and the peak wavelength shift was recorded. See FIG. 34.

EXAMPLE 2

Immobilization of One or More Specific Binding Substances

The following protocol was used on a colorimetric resonant reflective biosensor to activate the surface with amine functional groups. Amine groups can be used as a general-purpose surface for subsequent covalent binding of several types of linker molecules.

A glass substrate biosensor of the invention is cleaned by immersing it into piranha etch (70/30% (v/v) concentrated sulfuric acid/30% hydrogen peroxide) for 12 hours. The biosensor was washed thoroughly with water. The biosensor was dipped in 3% 3-aminopropyltriethoxysilane solution in dry acetone for 1 minute and then rinsed with dry acetone and air-dried. Alternatively, immersion of the biosensor in 10% 3-aminopropyltriethoxysilane (Pierce) solution in ethanol (Aldrich) for 1 min, followed by a brief ethanol rinse. Activated sensors were then dried at 70° C. for 10 minutes. The biosensor was then washed with water.

A semi-quantitative method is used to verify the presence of amino groups on the biosensor surface. One biosensor from each batch of amino-functionalized biosensors is washed briefly with 5 mL of 50 mM sodium bicarbonate, pH 8.5. The biosensor is then dipped in 5 mL of 50 mM sodium bicarbonate, pH 8.5 containing 0.1 mM sulfo-succinimidyl-4-O-(4,4'-dimethoxytrityl)-butyrate (s-SDTB, Pierce, Rockford, Ill.) and shaken vigorously for 30 minutes. The s-SDTB solution is prepared by dissolving 3.0 mg of s-SDTB in 1 mL of DMF and diluting to 50 mL with 50 mM sodium bicarbonate, pH 8.5. After a 30 minute incubation, the biosensor is washed three times with 20 mL of ddH2O and subsequently treated with 5 mL 30% perchloric acid. The development of an orange-colored solution indicates that the biosensor has been successfully derivatized with amines; no color change is observed for untreated glass biosensors.

The absorbance at 495 nm of the solution after perchloric acid treatment following the above procedure can be used as an indicator of the quantity of amine groups on the surface. In one set of experiment, the absorbance was 0.627, 0.647, and 0.728 for Sigma slides, Cel-Associate slides, and in-house biosensor slides, respectively. This indicates that the level of $NH_2$ activation of the biosensor surface is comparable in the activation commercially available microarray glass slides.

After following the above protocol for activating the biosensor with amine, a linker molecule can be attached to the biosensor. When selecting a cross-linking reagent, issues such as selectivity of the reactive groups, spacer arm length, solubility, and cleavability should be considered. The linker molecule, in turn, binds the specific binding substance that is used for specific recognition of a binding partner. As an example, the protocol below has been used to bind a biotin linker molecule to the amine-activated biosensor.

Protocol for Activating Amine-Coated Biosensor with Biotin

Wash an amine-coated biosensor with PBS (pH 8.0) three times. Prepare sulfo-succinimidyl-6-(biotinamido)hex-anoate (sulfo-NHS-LC-biotin, Pierce, Rockford, Ill.) solution in PBS buffer (pH 8) at 0.5 mg/ml concentration. Add 2 ml of the sulfo-NHS-LC-biotin solution to each amine-coated biosensor and incubate at room temperature for 30 min. Wash the biosensor three times with PBS (pH 8.0). The sulfo-NHS-LC-biotin linker has a molecular weight of 556.58 and a length of 22.4 Å. The resulting biosensors can be used for capturing avidin or strepavidin molecules.

Protocol for Activating Amine-Coated Biosensor with Aldehyde

Prepare 2.5% glutaraldehyde solution in 0.1 M sodium phosphate, 0.05% sodium azide, 0.1% sodium cyanoborohydride, pH 7.0. Add 2 ml of the sulfo-NHS-LC-biotin solution to each amine-coated biosensor and incubate at room temperature for 30 min. Wash the biosensor three times with PBS (pH 7.0). The glutaraldehyde linker has a molecular weight of 100.11. The resulting biosensors can be used for binding proteins and other amine-containing molecules. The reaction proceeds through the formation of Schiff bases, and subsequent reductive amination yields stable secondary amine linkages. In one experiment, where a coated aldehyde slide made by the inventors was compared to a commercially available aldehyde slide (Cel-Associate), ten times higher binding of streptavidin and anti-rabbit IgG on the slide made by the inventors was observed.

Protocol for Activating Amine-coated Biosensor with NHS 25 mM N,N'-disuccinimidyl carbonate (DSC, Sigma Chemical Company, St. Louis, Mo.) in sodium carbonate buffer (pH 8.5) was prepared. 2 ml of the DSC solution was added to each amine-coated biosensor and incubated at room temperature for 2 hours. The biosensors were washed three times with PBS (pH 8.5). A DSC linker has a molecular weight of 256.17. Resulting biosensors are used for binding to hydroxyl- or amine-containing molecules. This linker is one of the smallest homobifunctional NHS ester cross-linking reagents available.

Figure 34A:
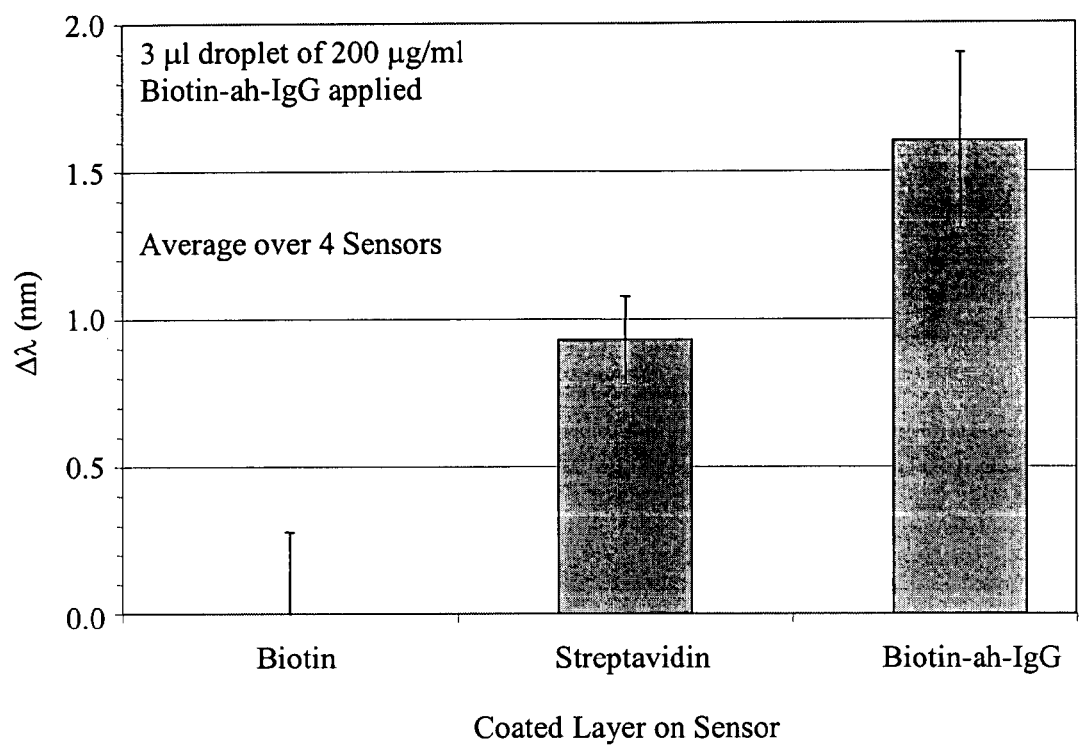
FIG. 34A-B.
Figure 34B:
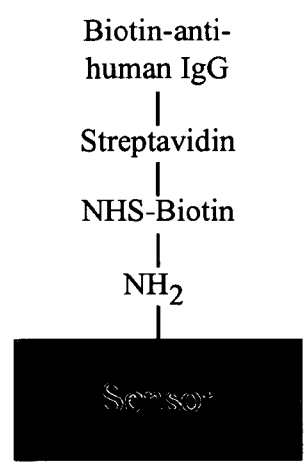

In addition to the protocols defined above, many additional surface activation and molecular linker techniques have been reported that optimize assay performance for different types of biomolecules. Most common of these are amine surfaces, aldehyde surfaces, and nickel surfaces. The activated surfaces, in turn, can be used to attach several different types of chemical linkers to the biosensor surface, as shown in Table 1. While the amine surface is used to attach several types of linker molecules, the aldehyde surface is used to bind proteins directly, without an additional linker. A nickel surface is used exclusively to bind molecules that have an incorporated histidine ("his") tag. Detection of "his-tagged" molecules with a Nickel activated surface is well known (Sigal et al., *Anal. Chem.* 68, 490 (1996)). Table 1 demonstrates an example of the sequence of steps that are used to prepare and use a biosensor, and various options that are available for surface activation chemistry, chemical linker molecules, specific binding substances and binding partners molecules. Opportunities also exist for enhancing detected signal through amplification with larger molecules such as HRP or streptavidin and the use of polymer materials such as dextran or TSPS to increase surface area available for molecular binding.

example, 3 µl droplets of biotinylated anti-human IgG in phosphate buffer solution (PBS) were deposited onto 4 separate locations on the biosensor surface at a concentration of 200 µg/ml. The solution was allowed to incubate on the biosensor for 30 minutes before rinsing thoroughly with PBS. The peak resonant wavelength of the 4 locations were measured after biotin activation, after streptavidin receptor application, and after ah-IgG binding. FIG. 34 shows that the addition of streptavidin and ah-IgG both yield a clearly measurable increase in the resonant wavelength.

EXAMPLE 4

Biotin/Streptavidin Assay

Figure 16A:
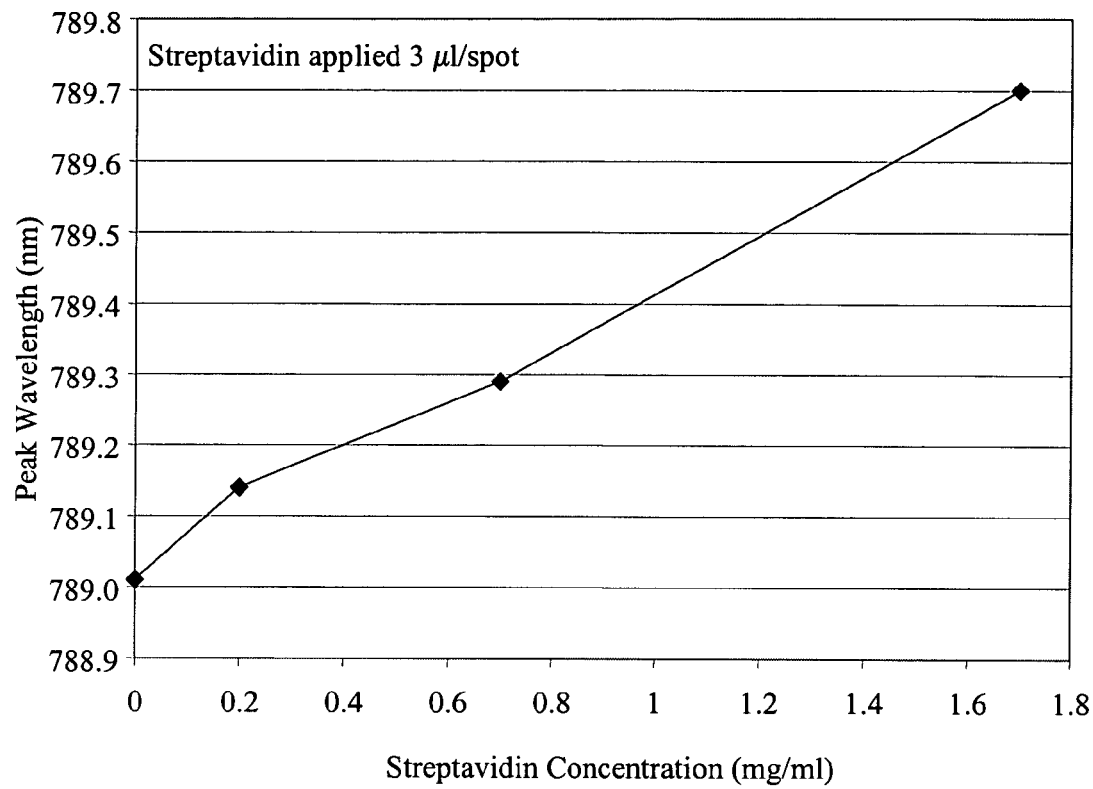
FIG. 16A-B.
Figure 16B:
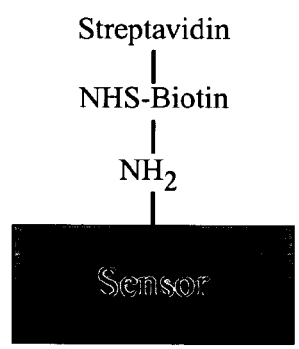

A series of assays were performed to detect streptavidin binding by a biotin receptor layer. A biosensor was first activated with amine chemistry, followed by attachment of a NHS-Biotin linker layer, as previously described. Next, 3 µl droplets of streptavidin in PBS were applied to the biosensor at various concentrations. The droplets were allowed to incubate on the biosensor surface for 30 min before thoroughly washing with PBS rinsing with DI water. The peak resonant wavelength was measured before and after streptavidin binding, and the resonant wavelength shifts are shown in FIG. 16. A linear relationship between peak wavelength and streptavidin concentration was observed, and in this case the lowest streptavidin concentration measured was 0.2 µg/ml. This concentration corresponds to a molarity of 3.3 nM.

EXAMPLE 5

Protein-Protein Binding Assay

An assay was performed to demonstrate detection of protein-protein interactions. As described previously, a biosensor was activated with amine chemistry and an NHS-

TABLE 1

| Bare Sensor | Surface Activation | Linker Molecule | Receptor Molecule | Detected Material | Label Molecule (Optional) |
| --- | --- | --- | --- | --- | --- |
| Glass | Amino | SMPT | Sm m'cules | Peptide | Enhance sensitivity |
| Polymers optional to enhance sensitivity | Aldehyde | NHS-Biotin DMP NNDC | Peptide Med Protein Lrg Protein · IgG | Med Protein Lrg Protein · IgG Phage | 1000 × HRP Streptavidin |
| 2-5 × Dextran | Ni | His-tag | | Cell | |
| TSPS | | Others . . . | cDNA | cDNA | |

EXAMPLE 3

IgG Assay

Figure 17A:
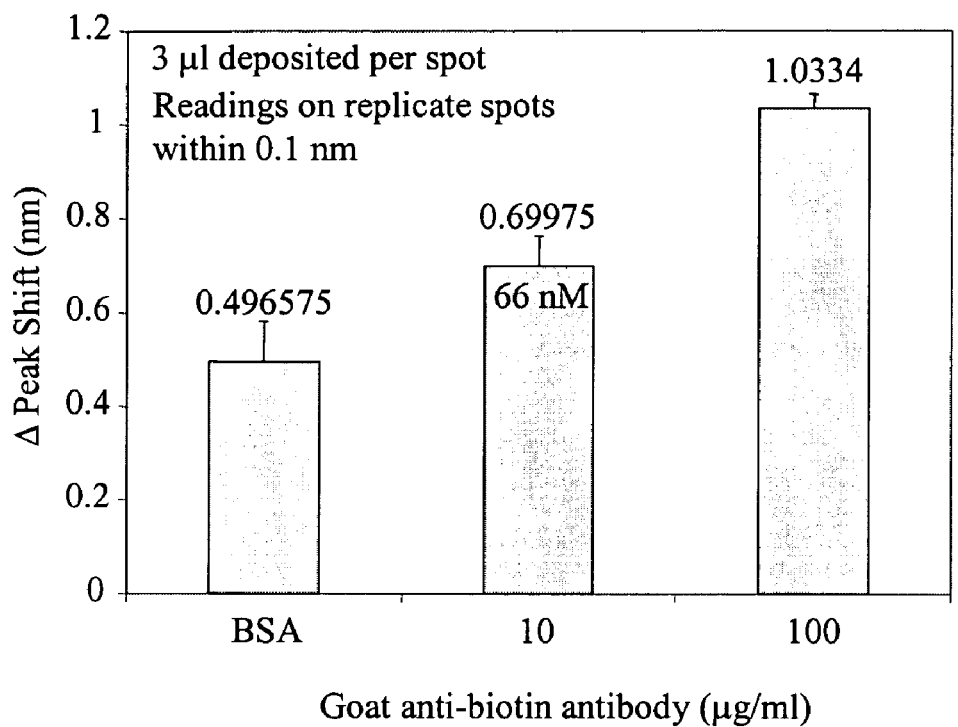
FIG. 17A-B.
Figure 17B:
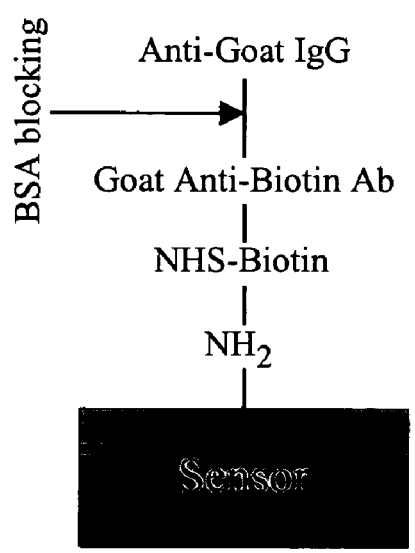

As an initial demonstration for detection of biochemical binding, an assay was performed in which a biosensor was prepared by activation with the amino surface chemistry described in Example 2 followed by attachment of a biotin linker molecule. The biotin linker is used to specifically interact with and effectively tether a streptavidin receptor molecule to the surface by exposure to a 50 µg/ml concentration solution of streptavidin in PBS at room temperature for 2-4 hours. The streptavidin receptor is capable of binding any biotinylated protein to the biosensor surface. For this biotin linker layer. A goat anti-biotin antibody receptor layer was attached to the biotin linker by exposing the biosensor to a 50 µg/ml concentration solution in PBS for 60 min at room temperature followed by washing in PBS and rinsing with DI water. In order to prevent interaction of nonspecific proteins with unbound biotin on the biosensor surface, the biosensor surface was exposed to a 1% solution of bovine serum albumin (BSA) in PBS for 30 min. The intent of this step is to "block" unwanted proteins from interacting with the biosensor. As shown in FIG. 17 a significant amount of BSA is incorporated into the receptor layer, as shown by the increase in peak wavelength that is induced. Following blocking, 3 µl droplets of various concentrations of anti-goat IgG were applied to separate locations on the biosensor surface. The droplets were allowed to incubate for 30 min before thorough rinsing with DI water. The biosensor peak resonant wavelength was measured before blocking, after blocking, after receptor layer binding, and after anti-goat IgG detection for each spot. FIG. 17 shows that an anti-goat IgG concentration of 10 μg/ml yields an easily measurable wavelength shift.

EXAMPLE 6

Unlabeled ELISA Assay

Figure 18A:
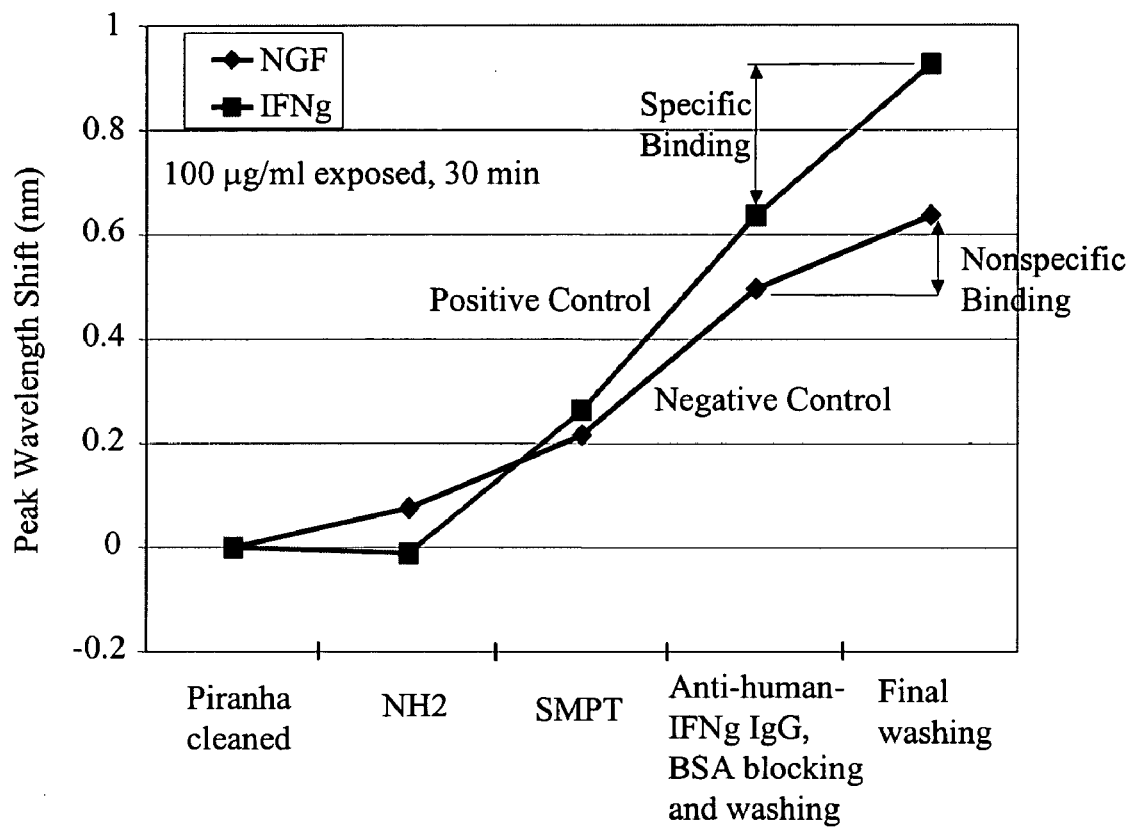
FIG. 18A-B.
Figure 18B:
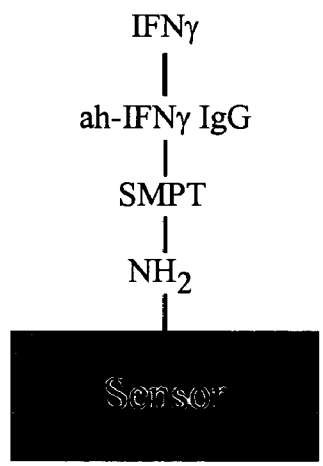

Another application of a biosensor array platform is its ability to perform Enzyme-Linked Immunosorbent Assays (ELISA) without the need for an enzyme label, and subsequent interaction an enzyme-specific substrate to generate a colored dye. FIG. 18 shows the results of an experiment where a biosensor was prepared to detect interferon-γ (IFN-γ) with an IFN-γ antibody receptor molecule. The receptor molecule was covalently attached to an $NH_2$-activated biosensor surface with an SMPT linker molecule (Pierce Chemical Company, Rockford, Ill.). The peak resonant wavelength shift for application of the $NH_2$, SMPT, and anti-human IFN-γ receptor molecules were measured for two adjacent locations on the biosensor surface, as shown in FIG. 18. The two locations were exposed to two different protein solutions in PBS at a concentration of 100 μg/ml. The first location was exposed to IFN-γ, which is expected to bind with the receptor molecule, while the second was exposed to neural growth factor (NGF), which is not expected to bind with the receptor. Following a 30 minute incubation the biosensor was measured by illuminating from the bottom, while the top surface remained immersed in liquid. The location exposed to IFN-γ registered a wavelength shift of 0.29 nm, while the location exposed to NGF registered a wavelength shift of only 0.14 nm. Therefore, without the use of any type of enzyme label or color-generating enzyme reaction, the biosensor was able to discriminate between solutions containing different types of protein.

EXAMPLE 7

Protease Inhibitor Assay (Caspase-3)

A Caspase-3 protease inhibitor assay was performed to demonstrate the biosensor's ability to measure the presence and cleavage of small molecules in an experimental context that is relevant to pharmaceutical compound screening.

Caspases (Cysteine-requiring Aspartate protease) are a family of proteases that mediate cell death and are important in the process of apoptosis. Caspase 3, an effector caspase, is the most studied of mammalian caspases because it can specifically cleave most known caspase-related substrates. The caspase 3 assay is based on the hydrolysis of the 4-amino acid peptide substrate NHS-Gly-Asp-Glu-Val-Asp p-nitroanilide (NHS-GDEVD-pNA) by caspase 3, resulting in the release of the pNA moiety.

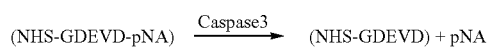

The NHS molecule attached to the N-terminal of the GDEVD provides a reactive end group to enable the NHS-GDEVD-pNA complex to be covalently bound to the biosensor with the pNA portion of the complex oriented away from the surface. Attached in this way, the caspase-3 will have the best access to its substrate cleavage site.

A biosensor was prepared by cleaning in 3:1 $H_2SO_4$:$H_2O_2$ solution (room temperature, 1 hour), followed by silanation (2% silane in dry acetone, 30 sec) and attachment of a poly-phe-lysine (PPL) layer (100 μg/ml PPL in PBS pH 6.0 with 0.5 M NaCl, 10 hours). The NHS-GDEVD-pNA complex was attached by exposing the biosensor to a 10 mM solution in PBS (pH 8.0, room temperature, 1 hour). A microwell chamber was sealed over the biosensor surface, and cleavage of pNA was performed by addition of 100 μl of caspase-3 in 1x enzyme buffer (100 ng/ml, room temperature, 90 minutes). Following exposure to the caspase 3 solution, the biosensor was washed in PBS. A separate set of experiments using a spectrophotometer were used to confirm the attachment of the complex to the surface of the biosensor, and functional activity of the caspase-3 for removal of the pNA molecule from the surface-bound complex.

Figure 19A:
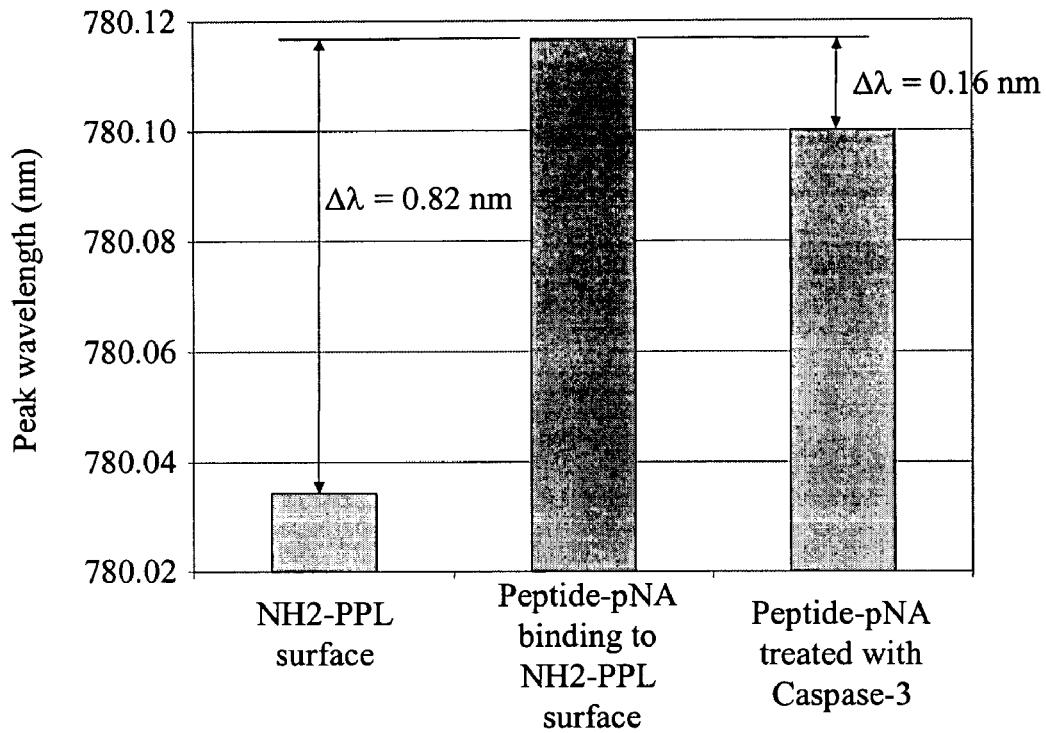
FIG. 19A-B.
Figure 19B:
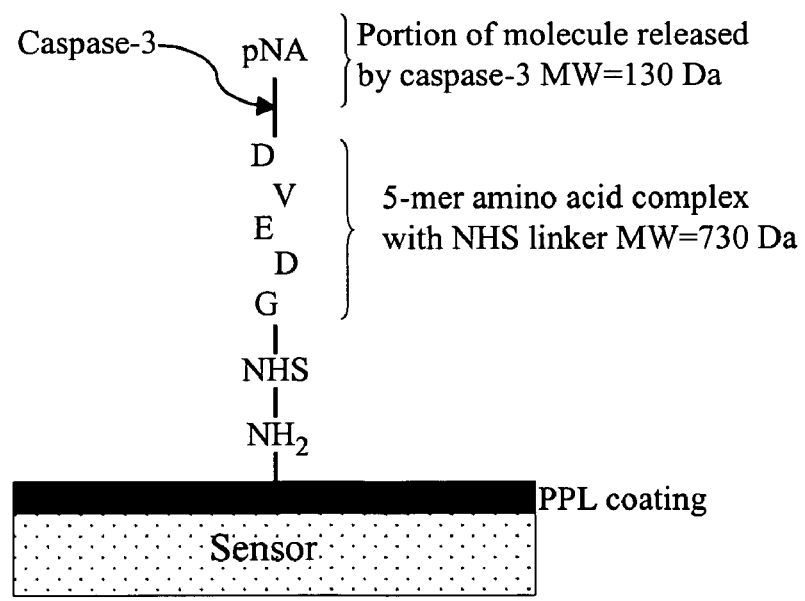

The peak resonant frequency of the biosensor was measured before attachment of the NHS-GDEVD-pNA complex, after attachment of the complex (MW=860 Da), and after cleavage of the pNA (MW=136) with caspase 3. As shown in FIG. 19, the attachment of the peptide molecule is clearly measurable, as is the subsequent removal of the pNA. The pNA removal signal of Δλ=0.016 nm is 5.3x higher than the minimum detectable peak wavelength shift of 0.003 nm. The proportion of the added molecular weight and subtracted molecular weight (860 Da/136 Da=6.32) are in close agreement with the proportion of peak wavelength shift observed for the added and subtracted material (0.082 nm/0.016 nm=5.14).

The results of this experiment confirm that a biosensor is capable of measuring small peptides (in this case, a 5-mer peptide) without labels, and even detecting the removal of 130 Da portions of a molecule through the activity of an enzyme.

EXAMPLE 8

Reaction Kinetics for Protein-Protein Binding Assays

Figure 20A:
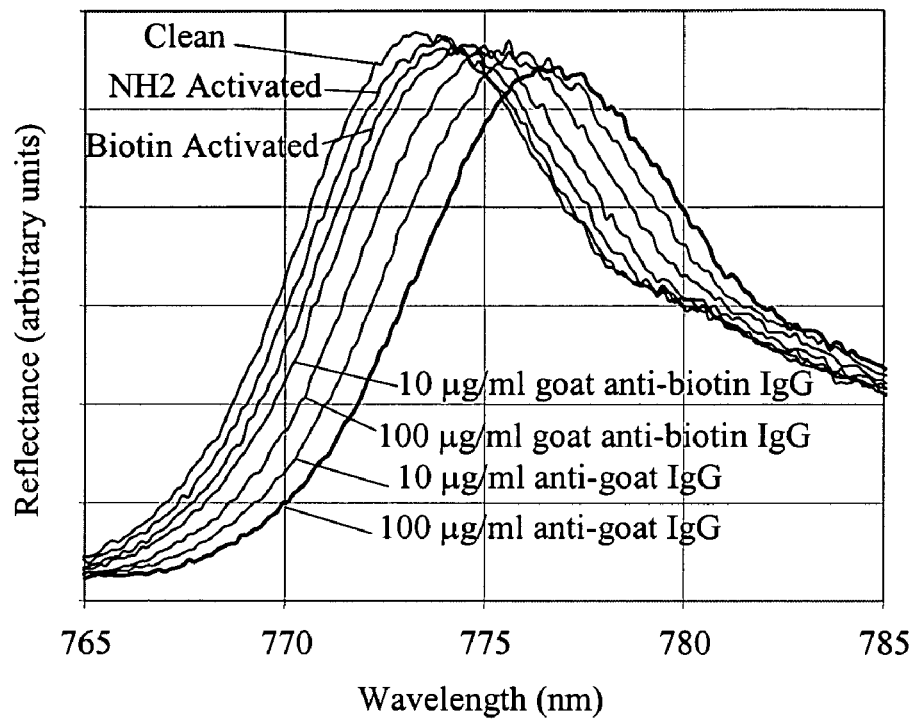
FIG. 20A-B.
Figure 20B:
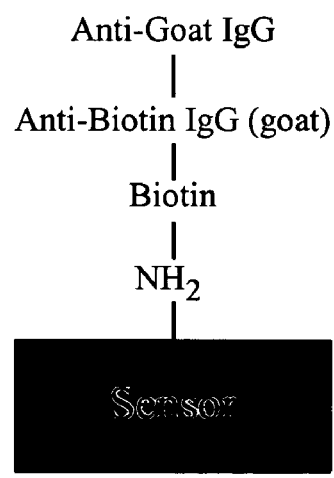

Because a biosensor of the invention can be queried continuously as a function of time while it is immersed in liquid, a biosensor can be utilized to perform both endpoint-detection experiments and to obtain kinetic information about biochemical reactions. As an example, FIG. 20 shows the results of an experiment in which a single biosensor location is measured continuously through the course of consecutively adding various binding partners to the surface. Throughout the experiment, a detection probe illuminated the biosensor through the back of the biosensor substrate, while biochemistry is performed on the top surface of the device. A rubber gasket was sealed around the measured biosensor location so that added reagents would be confined, and all measurements were performed while the top surface of the biosensor was immersed in buffer solution. After initial cleaning, the biosensor was activated with $NH_2$, and an NHS-Biotin linker molecule. As shown in FIG. 20, goat α-biotin antibodies of several different concentrations (1, 10, 100, 1000 μg/ml) were consecutively added to the biosensor and allowed to incubate for 30 minutes while the peak resonant wavelength was monitored. Following application of the highest concentration α-Biotin IgG, a second layer of protein was bound to the biosensor surface through the addition of α-goat IgG at several concentrations (0.1, 1, 10, and 100 μg/ml). Again, the resonant peak was continuously monitored as each solution was allowed to incubate on the biosensor for 30 minutes. FIG. 20 shows how the resonant peak shifted to greater wavelength at the end of each incubation period.

Figure 21A:
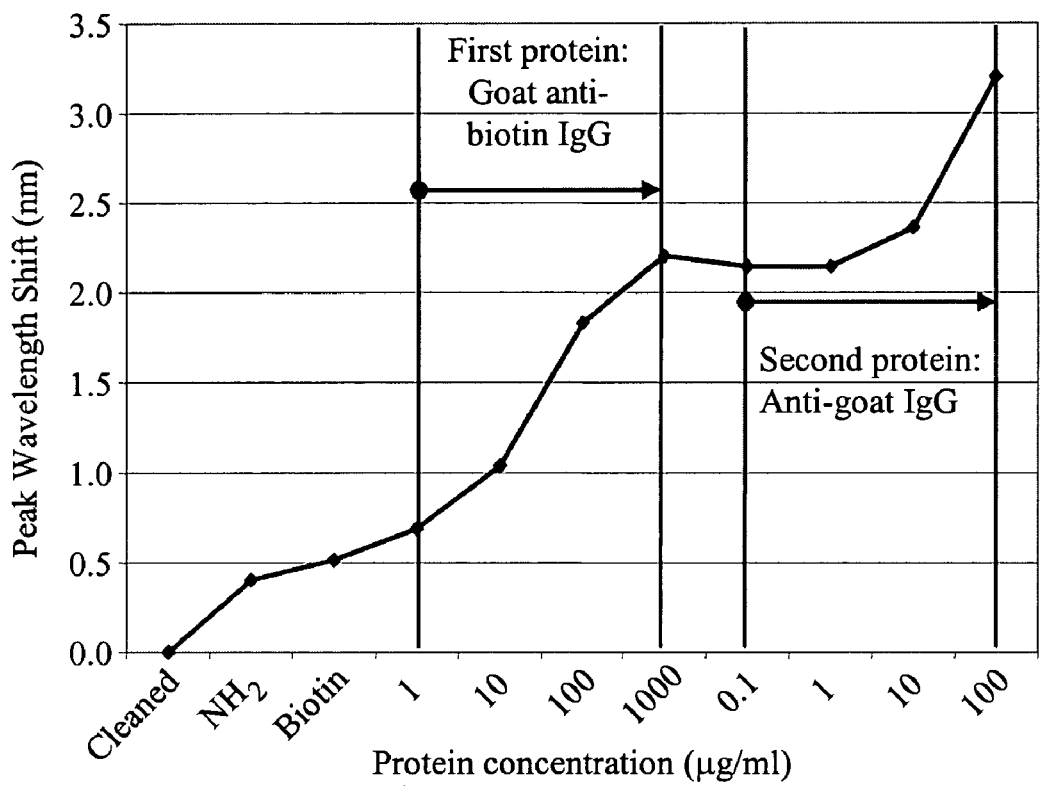
FIG. 21A-B.
Figure 21B:
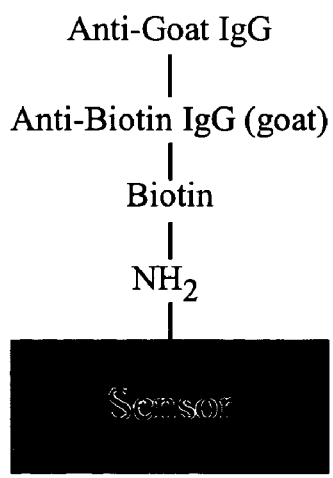
Figure 22A:
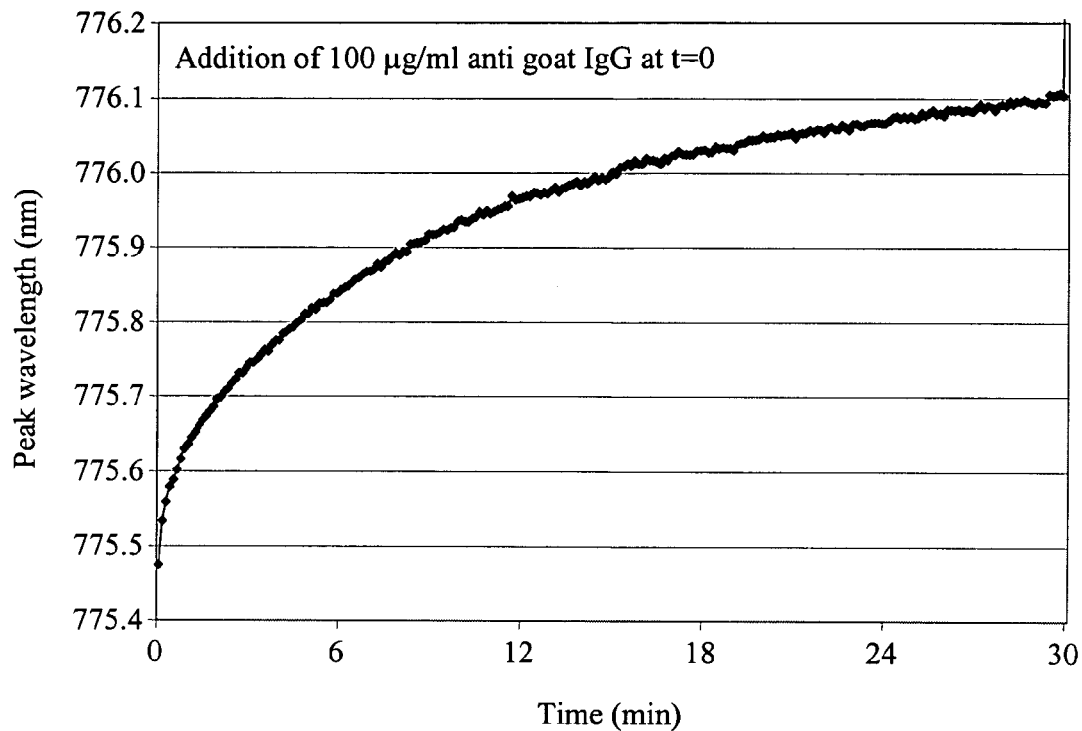
FIG. 22A-B.
Figure 22B:
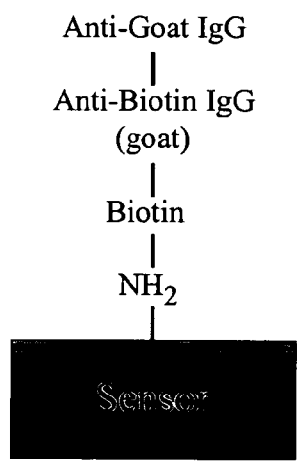

FIG. 21 shows the kinetic binding curve for the final resonant peak transitions from FIG. 20, in which 100 μg/ml of α-goat IgG is added to the biosensor. The curve displays the type of profile that is typically observed for kinetic binding experiments, in which a rapid increase from the base frequency is initially observed, followed by a gradual saturation of the response. This type of reaction profile was observed for all the transitions measured in the experiment. FIG. 22 shows the kinetic binding measurement of IgG binding.

Figure 23A:
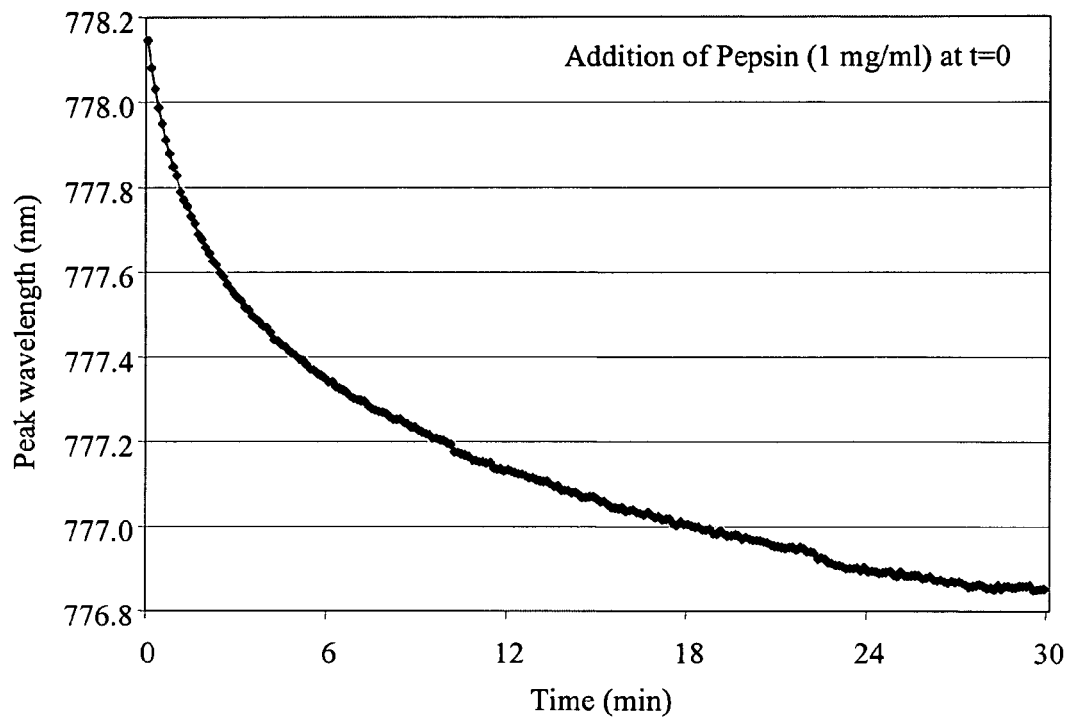
FIG. 23A-B.
Figure 23B:
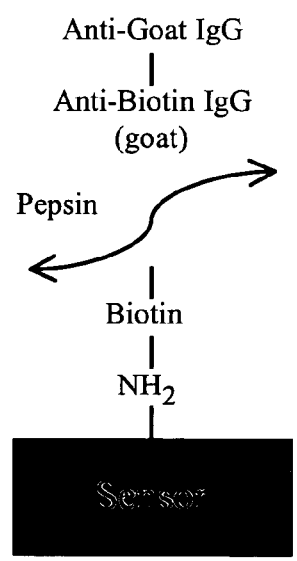

The removal of material from the biosensor surface through the activity of an enzyme is also easily observed. When the biosensor from the above experiment (with two protein coatings of goat anti-biotin IgG and anti-goat IgG) is exposed to the protease pepsin at a concentration of 1 mg/ml, the enzyme dissociates both IgG molecules, and removes them from the biosensor surface. As shown in FIG. 23, the removal of bound molecules from the surface can be observed as a function of time.

EXAMPLE 9

Proteomics Applications

Biosensors of the invention can be used for proteomics applications. A biosensor array can be exposed to a test sample that contains a mixture of binding partners comprising, for example, proteins or a phage display library, and then the biosensor surface is rinsed to remove all unbound material. The biosensor is optically probed to determine which distinct locations on the biosensor surface have experienced the greatest degree of binding, and to provide a quantitative measure of bound material. Next, the biosensor is placed in a "flow cell" that allows a small (e.g., <50 microliters) fixed volume of fluid to make contact to the biosensor surface. One electrode is activated so as to elute bound material from only selected biosensor array distinct locations. The bound material becomes diluted within the flow cell liquid. The flow cell liquid is pumped away from the biosensor surface and is stored within a microtiter plate or some other container. The flow cell liquid is replaced with fresh solution, and a new biosensor electrode is activated to elute its bound binding partners. The process is repeated until all biosensor distinct locations of interest have been eluted and gathered into separate containers. If the test sample liquid contained a mixture of proteins, protein contents within the separate containers can be analyzed using a technique such as electrospray tandem mass spectrometry. If the sample liquid contained a phage display library, the phage clones within the separate containers can be identified through incubation with a host strain bacteria, concentration amplification, and analysis of the relevant library DNA sequence.

EXAMPLE 10

Homogenous Assay Demonstration

An SWS biosensor detects optical density of homogenous fluids that are in contact with its surface, and is able to differentiate fluids with refractive indices that differ by as little as $\Delta n = 4 \times 10^{-5}$. Because a solution containing two free non-interacting proteins has a refractive index that is different from a solution containing two bound interacting proteins, an SWS biosensor can measure when a protein-protein interaction has occurred in solution without any kind of particle tag or chemical label.

Three test solutions were prepared for comparison:
 1. Avidin in Phosphate Buffer Solution (PBS), (10 μg/ml)
 2. Avidin (10 μg/ml)+Bovine Serum Albumin (BSA) (10 μg/ml) in PBS
 3. Avidin (10 μg/ml)+Biotinylated BSA (b-BSA) (10 μg/ml) in PBS A single SWS biosensor was used for all measurements to eliminate any possibility of cross-biosensor bias. A 200 μl sample of each test solution was applied to the biosensor and allowed to equilibrate for 10 minutes before measurement of the SWS biosensor peak resonant wavelength value. Between samples, the biosensor was thoroughly washed with PBS.

Figure 24:
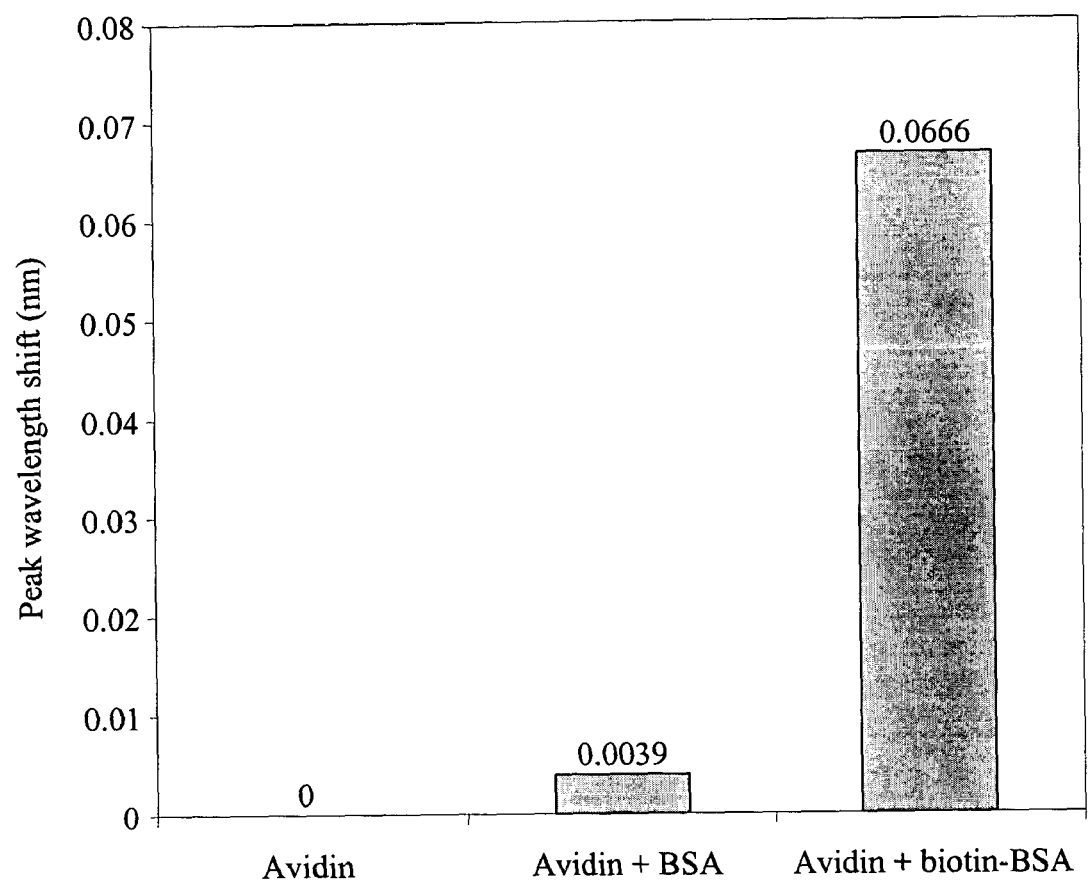
FIG. 24 shows a plot of the peak resonant wavelength values for test solutions. The avidin solution was taken as the baseline reference for comparison to the Avidin+BSA and Avidin+b-BSA solutions. Addition of BSA to avidin results in only a small resonant wavelength increase, as the two proteins are not expected to interact. However, because biotin and avidin bind strongly (Kd=$10^{-15}$M), the avidin+b-BSA solution will contain larger bound protein complexes. The peak resonant wavelength value of the avidin+b-BSA solution thus provides a large shift compared to avidin+BSA.

The peak resonant wavelength values for the test solutions are plotted in FIG. 24. The avidin solution was taken as the baseline reference for comparison to the Avidin+BSA and Avidin+b-BSA solutions. Addition of BSA to avidin results in only a small resonant wavelength increase, as the two proteins are not expected to interact. However, because biotin and avidin bind strongly ($Kd=10^{-15}M$), the avidin+ b-BSA solution will contain larger bound protein complexes. The peak resonant wavelength value of the avidin+ b-BSA solution thus provides a large shift compared to avidin+BSA.

The difference in molecular weight between BSA (MW=66 KDa) and b-BSA (MW=68 KDa) is extremely small. Therefore, the differences measured between a solution containing non-interacting proteins (avidin+BSA) and interacting proteins (avidin+b-BSA) are attributable only to differences in binding interaction between the two molecules. The bound molecular complex results in a solution with a different optical refractive index than the solution without bound complex. The optical refractive index change is measured by the SWS biosensor.

EXAMPLE 11

Microtiter Plate Assay

As a demonstration of the detection of biochemical binding on a calorimetric resonant reflectance optical biosensor which comprises an internal surface of a microtiter plate, the following assay was performed. The protein-protein system selected for this study was detection of anti-biotin IgG antibody using biotin immobilized on the biosensor surface as a specific binding substance. Therefore, a protocol for immobilization of biotin on the biosensor surface was developed that utilizes a bifunctional polyethyleneglycol-N-hydrosuccinimide (NHS-PEG) linker molecule (Shearwater Polymers, Inc.) to act as an intermediary between the amine surface group and the biotin. The NHS-PEG molecule is designed specifically to enable NHS to preferentially bind to the amine-activated surface, leaving the PEG portion of the molecule oriented away from the surface. The NHS-PEG linker molecule serves to separate the biotin molecule from the biosensor surface by a short distance so it may retain its conformation, and thus its affinity for other molecules. The PEG also serves to prevent nonspecific binding of proteins to the biosensor.

After attachment of amine-activated biosensor sheets into the bottom of microtiter plates, individual microtiter wells were prepared with three different surface functional groups in order to provide sufficient experimental controls for the detection of anti-biotin IgG. First, amine-activated surfaces were studied without additional modification. The amine-activated surface is expected to bind proteins nonspecifically, but not with high affinity. Second, microtiter wells with the NHS-PEG bifunctional linker molecule were prepared. The NHS-PEG molecule is expected to provide a surface that does not bind protein. Third, microtiter wells with an NHS-PEG-Biotin linker molecule were prepared. The NHS-PEG-Biotin molecule is expected to bind strongly to anti-biotin IgG.

To activate an amine-coated biosensor with biotin, 2 ml of NHS-PEG-Biotin (Shearwater) solution in TPBS (a reference buffer solution of 0.01% TWEEN™ 20 in phosphate buffer solution, pH 8) at 1.0 mg/ml concentration was added to the biosensor surface, and incubated at 37° C. for 1 hour. An identical procedure was used for attachment of a NHS-PEG (Shearwater) molecule without biotin. All purchased reagents were used as packaged.

A protein-antibody affinity assay was performed to demonstrate operation of a biosensor. A matrix of three separate biosensor surface states ($NH_2$, NHS-PEG, NHS-PEG-Biotin) were prepared and exposed to 7 concentrations of goat anti-biotin IgG (Sigma). Each matrix location was measured within a separate microtiter plate well, for a total of 21 wells measured simultaneously. Because the NHS-PEG wells are not expected to bind protein, they provide a reference for canceling common mode effects such as the effect of the refractive index of the test sample and environmental temperature variation during the course of an assay.

Figure 25:
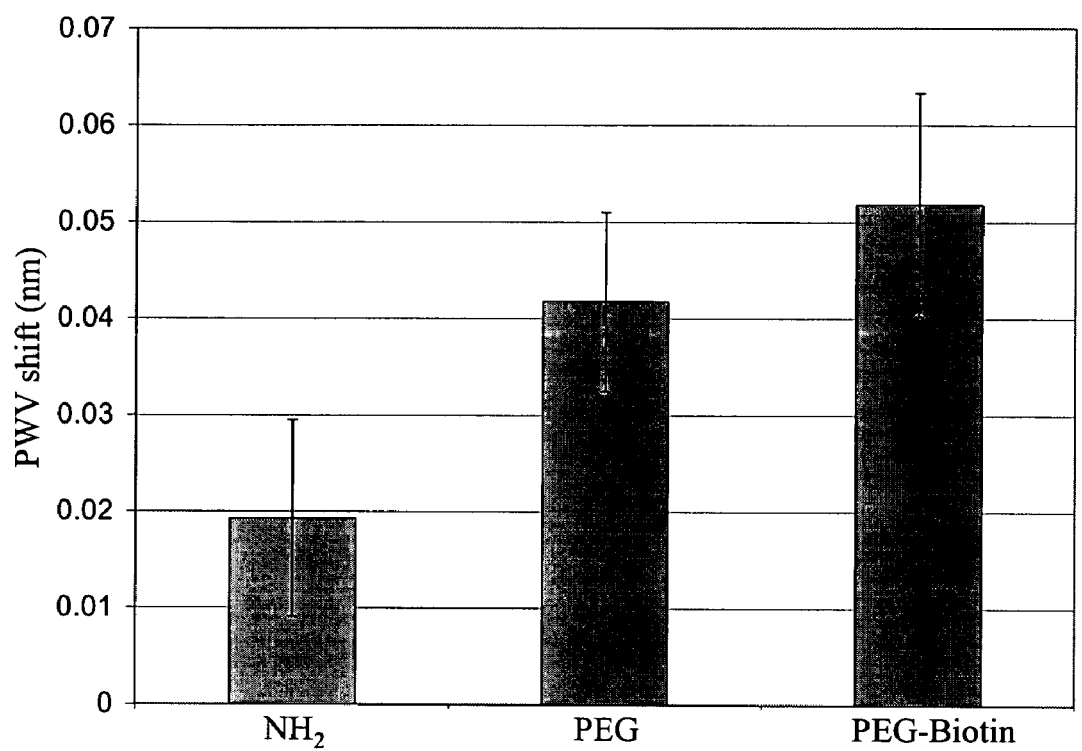
FIG. 25 shows the PWV shift-referenced to a sensor with no chemical functional groups immobilized, recorded due to the attachment of $NH_2$, $NH_2$+(NHS-PEG), and $NH_2$+(NHS-PEG-Biotin) molecules to the sensor surface. The error bars indicate the standard deviation of the recorded PWV shift over 7 microtiter plate wells. The data indicates that the sensor can differentiate between a clean surface, and one with immobilized $NH_2$, as well as clearly detecting the addition of the NHS-PEG (molecular weight approximately 2000 Daltons) molecule. The difference between surface immobilized NHS-PEG and NHS-PEG-Biotin (molecular weight approximately 3400 Dalton) is also measurable.

FIG. 25 plots the PWV shift-referenced to a biosensor with no chemical functional groups immobilized, recorded due to attachment of $NH_2$, $NH_2$+(NHS-PEG), and $NH_2$+(NHS-PEG-Biotin) molecules to the biosensor surface. The error bars indicate the standard deviation of the recorded PWV shift over 7 microtiter plate wells. The data indicates that the biosensor can differentiate between a clean surface, and one with immobilized $NH_2$, as well as clearly detecting the addition of the NHS-PEG (MW=2000 Da) molecule. The difference between surface immobilized NHS-PEG and NHS-PEG-Biotin (MW=3400 Da) is also measurable.

Figure 26:
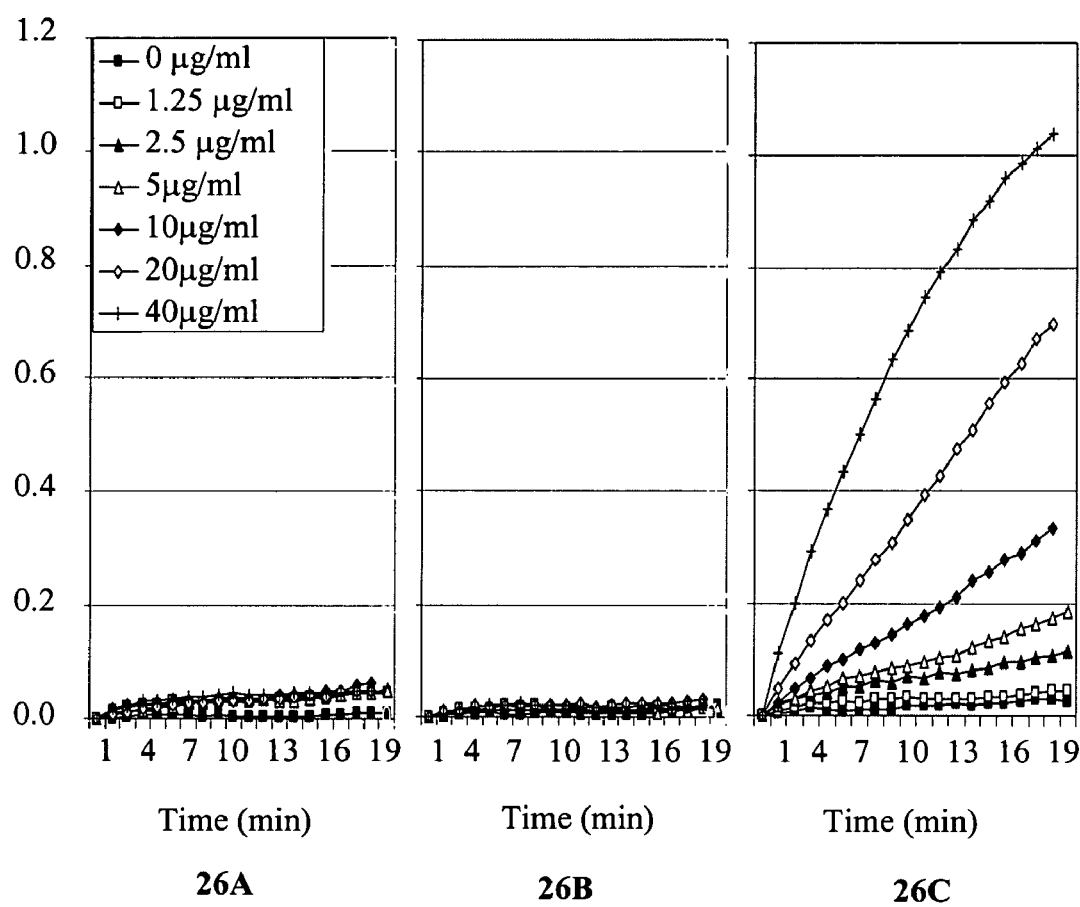
FIG. 26A-C shows the PWV shift response as a function of time for biosensor wells when exposed to various concentrations of anti-biotin IgG (0-80 mg/ml) and allowed to incubate for 20 minutes. The NHS-PEG surface (FIG. 26B) provides the lowest response, while the amine-activated surface (FIG. 26A) demonstrates a low level of nonspecific interaction with the anti-biotin IgG at high concentrations. The NHS-PEG-Biotin surface (FIG. 26C) clearly demonstrates strong specific interaction with the anti-biotin IgG-providing strong PWV shifts in proportion to the concentration of exposed anti-biotin IgG.

FIG. 26A-C shows the PWV shift response as a function of time for the biosensor wells when exposed to various concentrations of anti-biotin IgG (0-80 mg/ml) and allowed to incubate for 20 minutes. The NHS-PEG surface (FIG. 26B) provides the lowest response, while the amine-activated surface (FIG. 26A) demonstrates a low level of nonspecific interaction with the anti-biotin IgG at high concentrations. The NHS-PEG-Biotin surface (FIG. 26C) clearly demonstrates strong specific interaction with the anti-biotin IgG—providing strong PWV shifts in proportion to the concentration of exposed anti-biotin IgG.

The PWV shift magnitudes after 20 minutes from FIG. 26C are plotted as a function of anti-biotin IgG concentration in FIG. 25. A roughly linear correlation between the IgG concentration and the measured PWV shift is observed, and the lowest concentration IgG solution (1.25 µg/ml, 8.33 nM) is clearly measurable over the negative control PSB solution.

Figure 27:
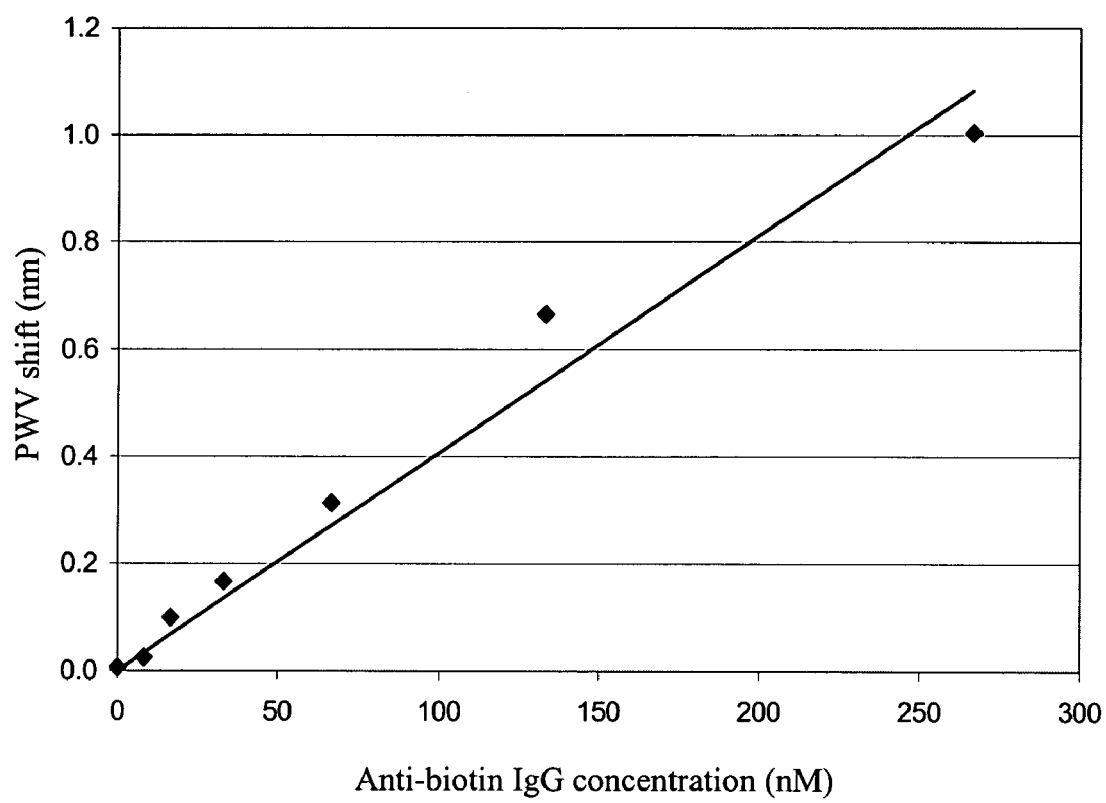
FIG. 27 shows the PWV shift magnitudes after 20 minutes from FIG. 26C plotted as a function of anti-biotin IgG concentration in FIG. 26. A roughly linear correlation between the IgG concentration and the measured PWV shift is observed, and the lowest concentration IgG solution (1.25 mg/ml, 8.33 nM) is clearly measurable over the negative control PBS solution.

The removal of material from the biosensor surface through the activity of an enzyme is shown in FIG. 27. When the biosensor is exposed to the protease pepsin at a concentration of 1 mg/ml (volume=100 µl), the enzyme disassociates both goat-anti biotin IgG and anti-goat IgG and removes them from the biosensor surface. The removal of bound molecules for the surface can be observed as a function of time.

EXAMPLE 12

Growing Cells on the Colorimetric Resonant Reflectance Optical Biosensor (96 well microtiter plate)

A colorimetric resonant reflectance optical biosensor which comprises an internal surface of a microtiter plate was sterilized prior to seeding of the culture. Sterilization was accomplished by placing the biosensor in Biosafety hood and exposing the microtiter plate and protection box to UV light for 12 to 48 hours, more preferably about 16 to 36 hours, still more preferably 18 to 30 hours and most preferably about 24 hours. Cells were harvested from a living cultures of chondrocyte cells grown in chondrocyte growth medium (Cell Applications, Inc.) and HEK human kidney tumor cells (ATCC) grown in RPMI (Sigma). $1 \times 10^5$ to $1 \times 10^6$ cells were added to each 96 well, the microtiter plate was placed into the protection box and incubated in $CO_2$ incubator at 37° C. for 24-48 hours.

Cell growth at a biosensor location can be detected via the peak wavelength values of the colorimetric resonant reflectance optical biosensor surface or monitored more generally using a microscope, digital camera, conventional camera, or other visualization apparatus, magnifying or nonmagnifying, that utilizes lens-based optics or electronics-based charge coupled device (CCD) technology.

EXAMPLE 13

Detect Cell Morphology Change on the Colorimetric Resonant Reflectance Optical Biosensor Cell morphology changes were detected utilizing a calorimetric resonant reflectance optical biosensor which comprises an internal surface of a microtiter plate. Chondrocyte cells were grown to 10-90% confluent monolayer according to Example 12. The cell monolayer was washed with salt-balanced buffer such as Hank's medium (Sigma), and monolayer stability was tested washing or incubating the cells with the salt-balanced medium such as Hank's medium for 10 minutes. Monolayer stability at any biosensor location can be assessed by detecting the peak wavelength value at any location before, during or after the washing or incubation step.

Figure 28:
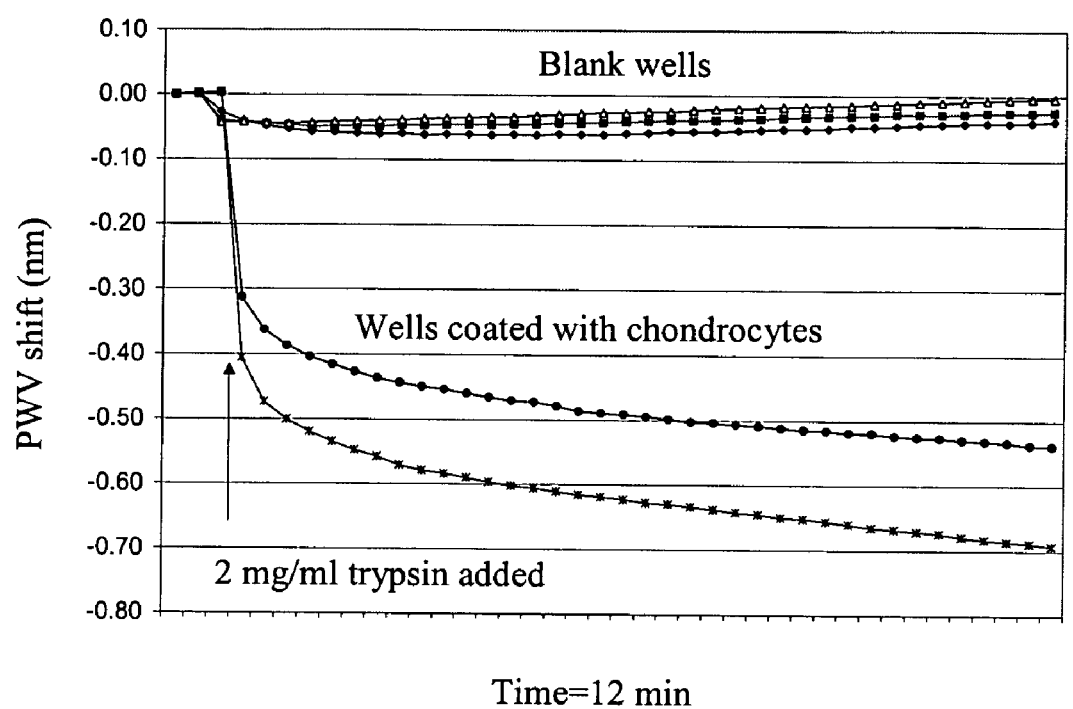
FIG. 28 shows the results of a cell morphology assay utilizing chondrocyte cells grown on the calorimetric resonant reflectance optical biosensor. The cells were observed to remain attached to the surface of the biosensor throughout the assay; the observed decrease in PWV upon addition of 2 mg/ml trypsin to the biosensor wells containing the chondrocyte cells indicates a change in chondrocyte cell morphology.

0.25% trypsin in Tris-EDTA was warmed to room temperature and added to the biosensor wells while peak wavelength values were being detected. Blank controls were also utilized in which no cells were grown. As can be seen in FIG. 28, reaction progress was followed over 12 minutes. The cells were observed to remain attached to the surface of the biosensor throughout the assay; the observed decrease in PWV upon addition of 2 mg/ml trypsin to the biosensor wells containing the chondrocyte cells indicates a change in chondrocyte cell morphology. The control (no chondrocyte cell) wells exhibited an insignificant response to the addition of trypsin.

Figure 29:
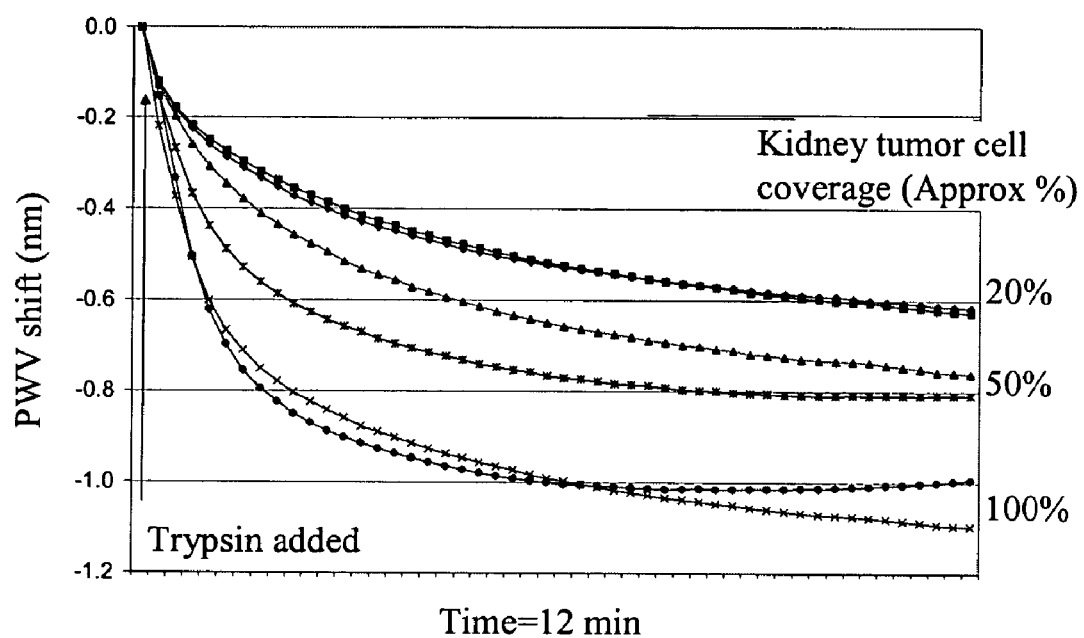
FIG. 29 shows the results of a cell adhesion assay using kidney tumor cells. Trypsin was added to six biosensor wells containing kidney tumor cells grown on the surface of the biosensor. Two wells were utilized as replicate samples for each of the three trypsin concentrations. Upon addition of the trypsin, a decrease in PWV is observed indicating the detachment of the cells from the surface of the sensor.

FIG. 29 shows the results of a cell adhesion assay using kidney tumor cells. Trypsin was added to six biosensor wells containing kidney tumor cells grown on the surface of the biosensor. Two wells were utilized as replicate samples for each of the three trypsin concentrations. Upon addition of the trypsin, a decrease in PWV is observed indicating the detachment of the cells from the surface of the biosensor.

Both primary and tumor cell lines have been observed to grow well on the calorimetric resonant reflectance optical biosensor surface within the microtiter plate well, and eukaryotic cells have been observed to generate very stable PWVs.

EXAMPLE 14

Detecting Molecules Released from Cells Grown in a Semi-Permeable Internal Sleeve Held in Contact with a Colorimetric Resonant Reflectance Optical Biosensor Molecules secreted, shed or otherwise ejected from cells can be detected utilizing a calorimetric resonant reflectance optical biosensor which comprises an internal surface of a microtiter plate well. Antibodies against interleukin-1 were immobilized on the surface of the colorimetric resonant reflectance optical biosensor within the microtiter plate well. A semi-permeable internal sleeve was inserted into the well, followed by mouse macrophage cells (ATCC CRL-2019) and RPMI 1640 growth medium (Sigma). The cells were grown according to the method of Example 12 while detecting the calorimetric resonant reflectance optical PWV at several locations on the biosensor surface. When lipopolysaccharide (Sigma) was then used to stimulate the production of interleukin-1, PWVs were seen to increase over time as interleukin-1, secreted from the macrophage cells, diffused through the semi-permeable internal sleeve and bound to the interleukin-1 antibody immobilized on the biosensor surface.

EXAMPLE 15

Protein Microarray Demonstration on the Colorimetric Resonant Reflectance Optical Biosensor The colorimetric resonant reflectance optical biosensor is able to perform assays in an array format; this example illustrates the ability to detect differential binding affinities among different types of IgG.

Figure 35A:
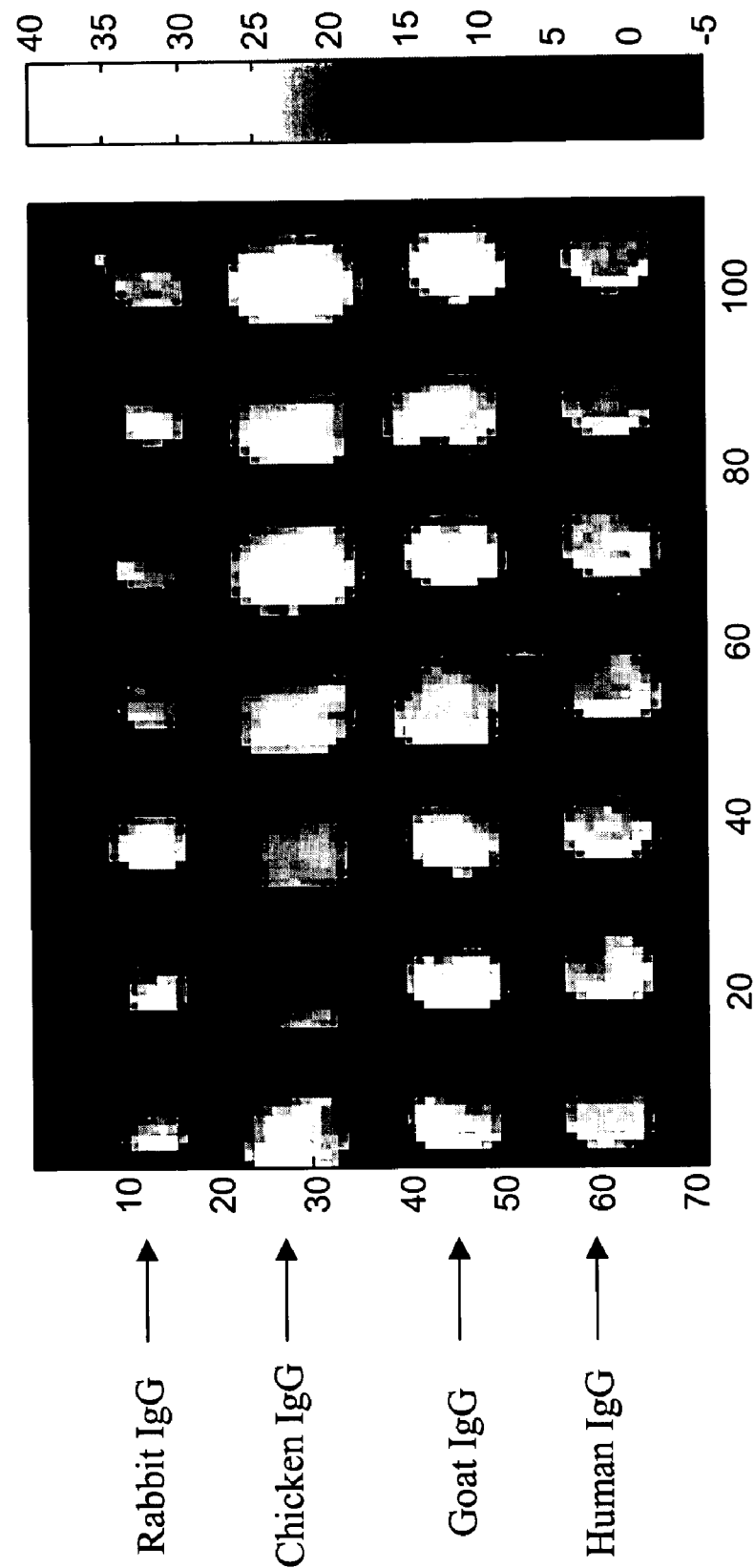
FIG. 35A-B.
Figure 35B:
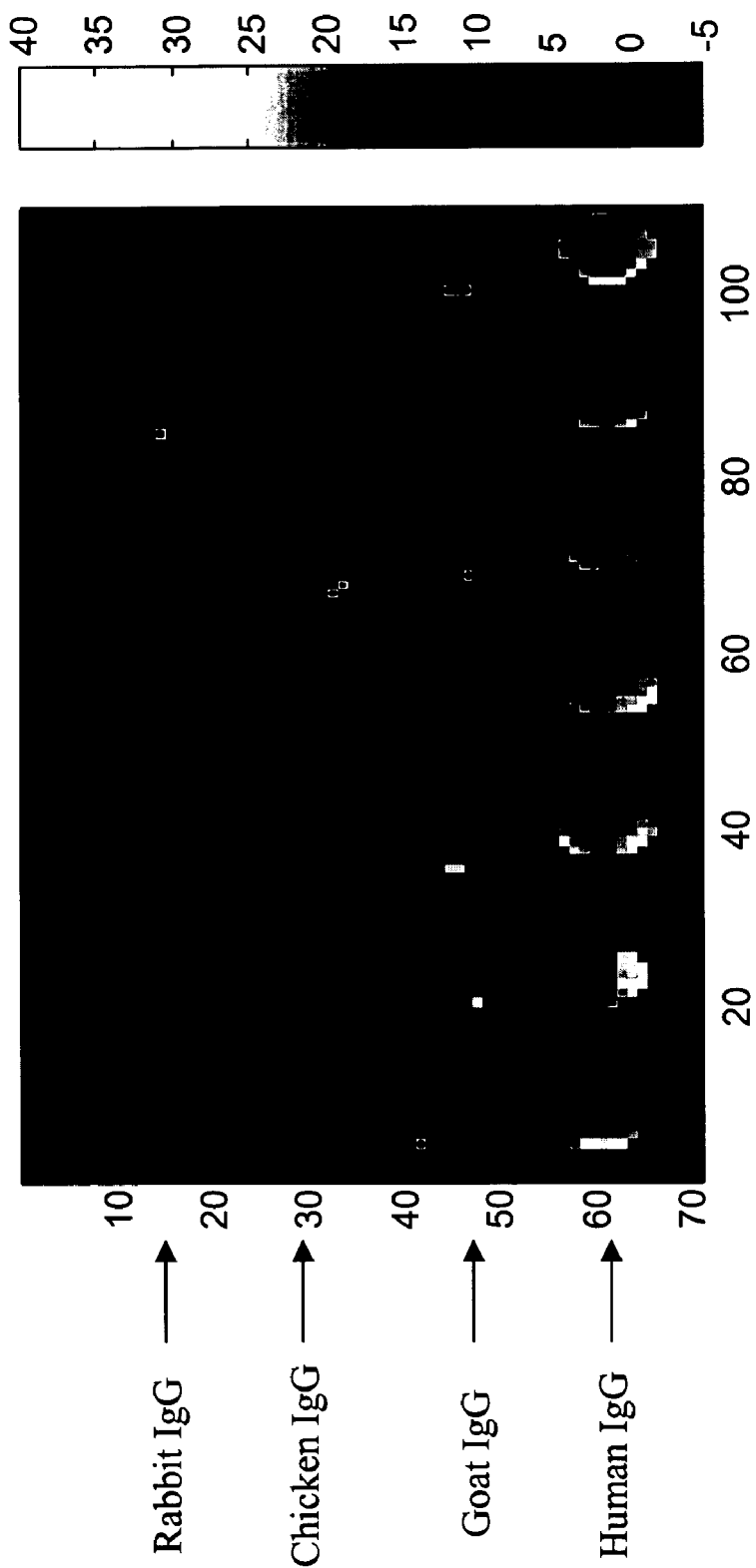

In this example, a biosensor sheet was cut into a 1-in×2-in rectangular region. The sensor is comprised of a hydrophobic TaO surface, to which 1 mg/ml each of rabbit-IgG, chicken-IgG, goat-IgG, and human-IgG (all IgG from Sigma) are spotted using an Affymetrix GMS pin-and-loop spotter with 400-μm spotting loops. In total, 4 rows of 7 spots each are made (see FIG. 35-A), in which the rabbit-IgG comprised the first row; the chicken-IgG comprised the second row; the goat-IgG comprised the third row, and the human IgG comprised the fourth row. After spotting, the IgG's are incubated at room temperature for 30-min. Subsequently, a SRU Microarray Scanner comprised of a Jobin Yvon high resolution imaging spectrometer is used to scan the resulting data, shown in FIG. 35-A.

After spotting, 1 mg/ml of gelatin (Sigma) is flowed over the surface as a blocking agent to prevent the binding agent (anti-human-IgG) from non-specifically binding to the non-spotted areas. The entire microarray slide is then rinsed three times in PBS for 10-seconds each time, followed by three rinses in $H_2O$, also for 10-seconds each time. The resulting microarray is then scanned using the SRU Microarray Scanner. Lastly, 100 μg/ml of anti-human-IgG is flowed over the entire surface, and allowed to incubate at room temperature for 30-min prior to rinsing using the same PBS rinse procedure identified above. The resulting microarray containing the binding interactions is scanned using a SRU Microarray Scanner once again. The difference between this final scan and the scan performed after blocking shows the amount of material bound to each spot on the microarray (see FIG. 35-B). In particular, the high degree of affinity between the human-IgG and the anti-human-IgG is evident in the strong response corresponding to the bottom-most row of FIG. 35-B. Additionally, at an intensity scale of 0.04 nm/intensity count in FIG. 35-B, the binding result of 0.8-nm to 1.0-nm wavelength shift observed by the microarray system is consistent to observations made in well-based assays.

EXAMPLE 16

DNA-DNA Binding Interaction Demonstration on the Colorimetric Resonant Reflectance Optical Biosensor To demonstrate the detection of hybridization events on the colorimetric resonant reflectance optical biosensor, an experiment using 18-base oligonucleotide sequences of adenine (poly-A) hybridizing to immobilized 18-base oligonucleotide sequences of thymine (poly-T) was performed using a bottomless 96-well plate that was bonded to a biosensor sheet. The poly-A sequence has a Cy-5 labeled attached to its 3'-terminal end to permit a validation of the binding using fluorescence.

Specifically, a biosensor with hydrophobic TaO top layer was first coated with poly-phenylalanine-lysine (PPL) (Sigma); the biosensor was bonded to bottomless polystyrene 96-well microtiter plates (Greiner). A hybridization buffer solution comprised of 3 X SSC buffer (Sigma) and 0.1% SDS (Sigma) was created. Subsequently, 9 wells (three sets of three wells) were utilized to examine three different analytes, each in triplicate. Specifically, in the first and second sets of wells, 10 mM of poly-T (Oligos Etc., Inc.) in water was added. In the third set of wells, DNA from the T7 promoter region (New England BioLabs) was immobilized. After immobilization, hybridization buffer was first used to rinse all wells, afterwards, the hybridization buffer was added to the first set of wells, providing a baseline response curve. In the second set of wells, poly-A (with Cy-5 label) was added so as to induce hybridization between the immobilized poly-T and the poly-A. In the third set of wells, poly-A (with Cy-5) was added to the immobilized T7 DNA to generate non-specific binding.

Figure 36A:
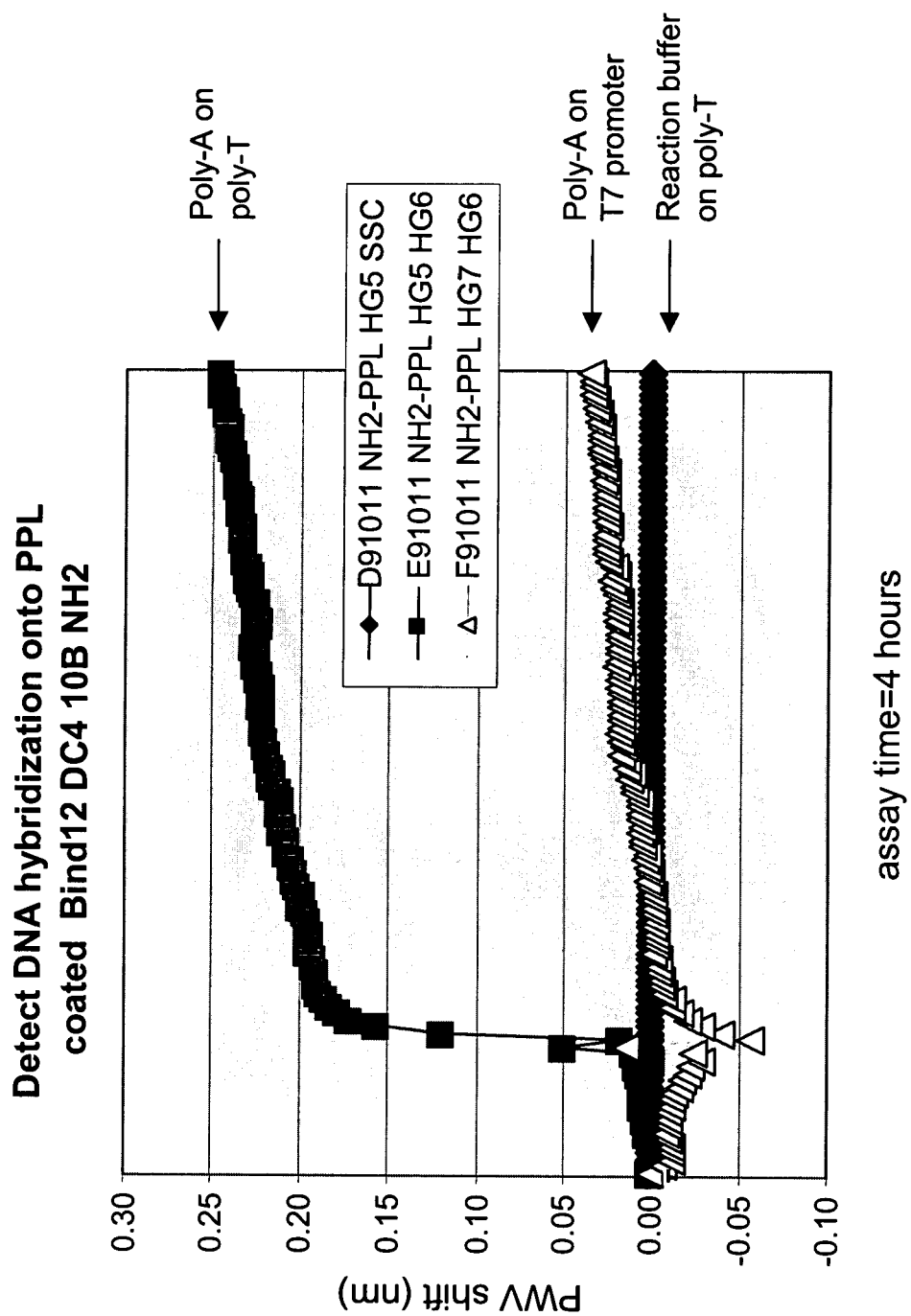
FIG. 36A-B. With Poly-T immobilized on the sensor surface.
Figure 36B:
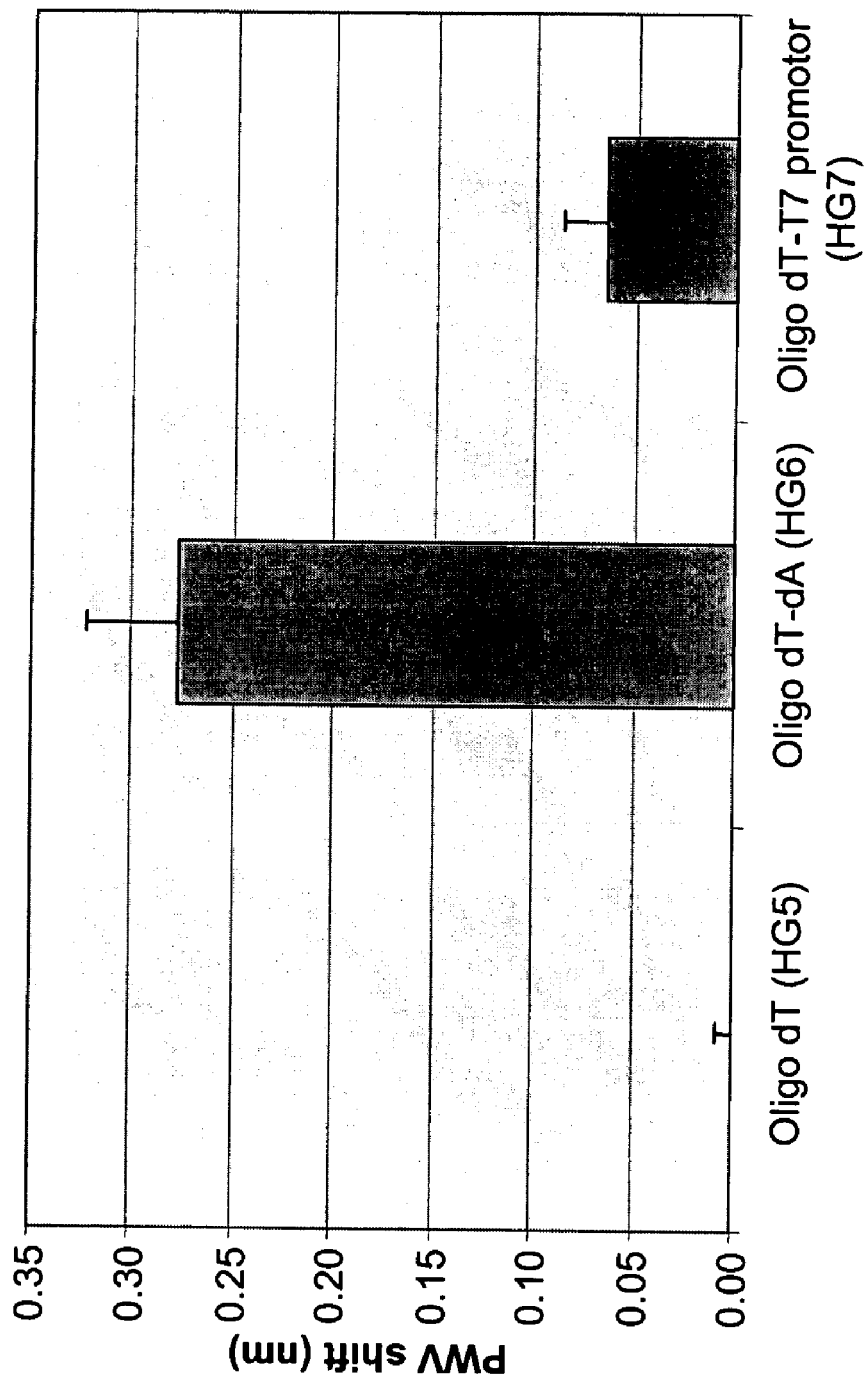

FIG. 36 summarizes the results of these experiments. In FIG. 36A, a graphical plot of the amount of binding resulting from poly-T, poly-A, and T7-promoter are shown. This same data is plotted as endpoints, along with error bars, in FIG. 36B. It is readily apparent from these plots that the biosensor can measure the specific hybridization between poly-T and poly-A, as well as distinguish such strong interactions from weaker non-specific interactions.

EXAMPLE 17

Protein-DNA Interaction Demonstration on the Colorimetric Resonant Reflectance Optical Biosensor In yet another experiment, the ability to utilize the colorimetric resonant reflectance optical biosensor to detect interaction between proteins and DNA was demonstrated. In this case, the interaction between T7 promoter DNA and T7 RNA polymerase was used as an illustration.

Using a TaO-coated biosensor that was bonded to the bottom of a bottomless 96-well polystyrene microtiter plate (Greiner), poly-phenylalanine-lysine (PPL) (Sigma) was first used to coat the sensor surface. In particular, 12 wells were coated with PPL—three wells for each of four analytes to be examined.

Figure 37:
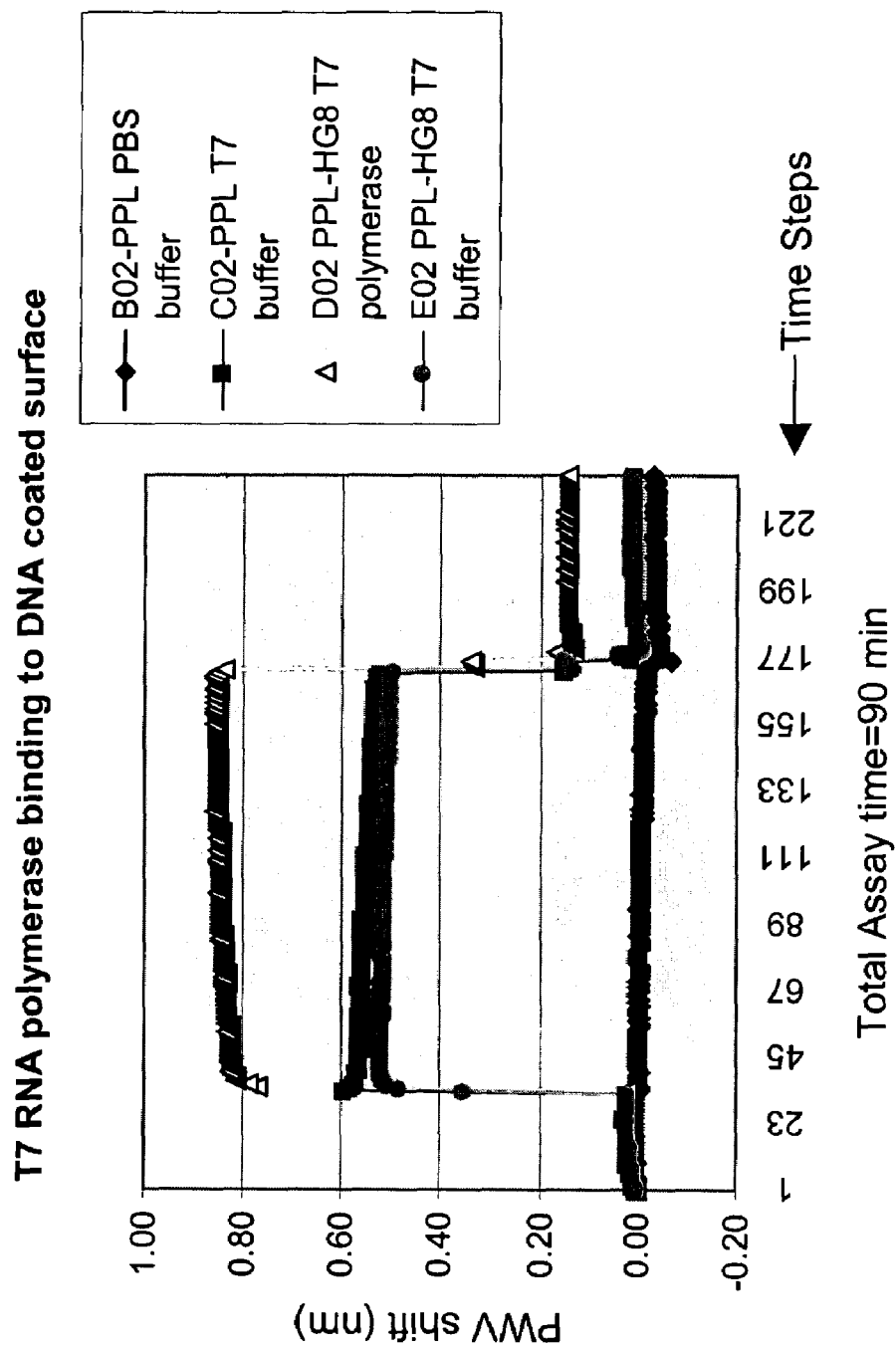
FIG. 37 shows an example of the specificity with which protein-DNA interactions, in this case between T7-promoter DNA and T7 RNA polymerase, can be detected.

In the first set of wells, PBS buffer at pH=7.4 (Sigma) was added. In the second set of wells, reaction buffer for T7 RNA polymerase (New England BioLabs) was added. In the third set of wells, the T7-promoter DNA (New England BioLabs) was immobilized first, followed by the addition of T7 RNA polymerase in reaction buffer (New England BioLabs). In the fourth set of wells, T7-promoter DNA was immobilized, followed by the reaction buffer. In principle, the T7 reaction buffer should provide only non-specific responses, unless both T7 DNA and the T7 RNA polymerase are present. As shown in FIG. 37, this was indeed the case. Specifically, note that at the 175th time step a rinse procedure took place in order to remove buffer effects; subsequent to this rinse, it was apparent that protein-DNA interactions occurred only in the wells containing both the T7 promoter DNA and the T7 RNA polymerase.

EXAMPLE 18

Current techniques for studying cell-protein interactions and other cell interactions are time consuming and labor intensive because they can involve many steps including radioisotope or fluorescence labeling, washing, blocking, and detecting. See e.g. Table 2. Current techniques for studying cell-protein interactions and other cell interactions can also use extensive amounts of expensive reagents. The instant invention provides compositions and methods for determining cell interactions that are faster than conventional methods and that require the use of fewer reagents than conventional methods.

The instant methods and compositions provide a label-free, simple, high throughput assay to identify cell specificity for specific binding substances, including proteins, cell migration, cell chemotaxis, specific binding substance-cell interactions, cell-extracellular matrix interactions, and cell-cell interactions.

In one embodiment of the invention the methods and compositions can reduce the usage of reagents significantly in cell assays. Reagent usage can be reduced by at least 100 times in comparison with microtiter plate whole well assays. More importantly, the simple image cell assays of the invention can replace current time consuming and labor intensive cell migration assays and cell chemotaxis assays with greater accuracy and reproducibility.

Colorimetric resonant reflectance optical biosensor technology is very sensitive to optical property changes due to biomolecules and biological cells interacting with the biosensor surface. This feature offers a great advantage for these biosensors in biological applications, such as investigating the interaction between biomolecules, including between biomolecules and biomolecules bound on a cell surface such as a cell surface receptor or a cell surface marker. Since colorimetric resonant reflectance optical biosensor technology directly detects biointeraction, the fluorescence label, radioisotope label, or biological tag such as enzymes and biological motifs are not needed. Colorimetric resonant reflectance optical biosensor cell attachment assays provide novel methods to directly detect the interaction between a molecule and its counterpart on a cell surface. The principle of a colorimetric resonant reflectance optical biosensor cell attachment assay is that the affinity binding between an immobilized target molecule and its counterpart on a cell surface will lead a cell to interact with the biosensor surface wherein this interaction can be detected.

One embodiment of the invention provides a vessel comprising a calorimetric resonant reflectance optical biosensor, wherein the colorimetric resonant reflectance optical biosenseor comprises an internal surface of the vessel. For example, the calorimetric resonant reflectance optical biosensor can comprise a bottom surface of the vessel. One or more specific binding substances, such as two or more specific binding substances, are immobilized at two or more distinct locations on the internal surface of the vessel that comprises a colorimetric resonant reflectance optical biosensor. There may be different quantities of one specific binding substance at two or more distinct locations. A vessel can comprise, for example, a microtiter well, test tube, petri dish or microfluidic channel. One embodiment of the invention provides a microtiter plate comprising one or more microtiter wells, wherein a bottom surface of the one or more microtiter wells comprises a colorimetric resonant reflectance optical biosensor. One or more specific binding substances can be immobilized at two or more distinct locations on the bottom surface of each microtiter well.

The invention provides methods of detecting binding of one or more types of cells to one or more specific binding substances. In one embodiment of the invention one or more types of cells are applied to an internal surface of a vessel. Any type of cell can be used, including, for example, prokaryotic cells, eukaryotice cells, artificial cells, cell membranes or artificial cell membranes. The cells can grow as, for example, adherent cells in culture or as suspension cells in culture. The internal surface of the vessel comprises a colorimetric resonant reflectance optical biosensor, wherein two or more specific binding substances are immobilized at two or more distinct locations on the internal surface of the vessel that comprises a calorimetric resonant reflectance optical biosensor. The vessel is illuminated with light and one or more peak wavelength values (PWVs) for each distinct location is detected. A peak wavelength value (PWV) is a relative measure of the binding substance and/or cells that are bound to the biosensor. If the one or more cells have bound to a specific binding substance, then the PWV is shifted at the distinct location to which the one or more cells are bound. The PWV is shifted in comparison to, for example, a portion of the biosensor that has no specific binding substance bound, or to a portion of the biosensor that has only specific binding substances bound, or to a given baseline PWV.

The one or more specific binding substances can be arranged in, for example an array of distinct locations on the internal surface of the vessel that comprises a colorimetric resonant reflectance optical biosensor. The distinct locations can define an array spot of about 50-500 microns in diameter. The one or more specific binding substances can be randomly arranged on the internal surface of the vessel. The one or more specific binding substances can be immobilized on the internal surface of the vessel that comprises a colorimetric resonant reflectance optical biosensor by a method such as physical adsorption, chemical binding, electrochemical binding, electrostatic binding, hydrophobic binding and hydrophilic binding, for example.

Another embodiment of the invention provides a method of detecting binding of one or more cells to a specific binding substance. The method comprises immobilizing one or more specific binding substances, such as two or more specific binding substances, at two or more distinct locations on an internal surface of a vessel, wherein the internal surface of the vessel comprises a colorimetric resonant reflectance optical biosensor and illuminating the vessel with light. One or more peak wavelength values for each distinct location is determined. One or more cells are applied to the internal surface of the vessel. The vessel is illuminated with light and one or more peak wavelength values are detected for each distinct location. The peak wavelengths are compared. If the one or more cells have bound to a specific binding substance, then the PWV is shifted at the distinct location to which the specific binding substance is bound.

Figure 38:
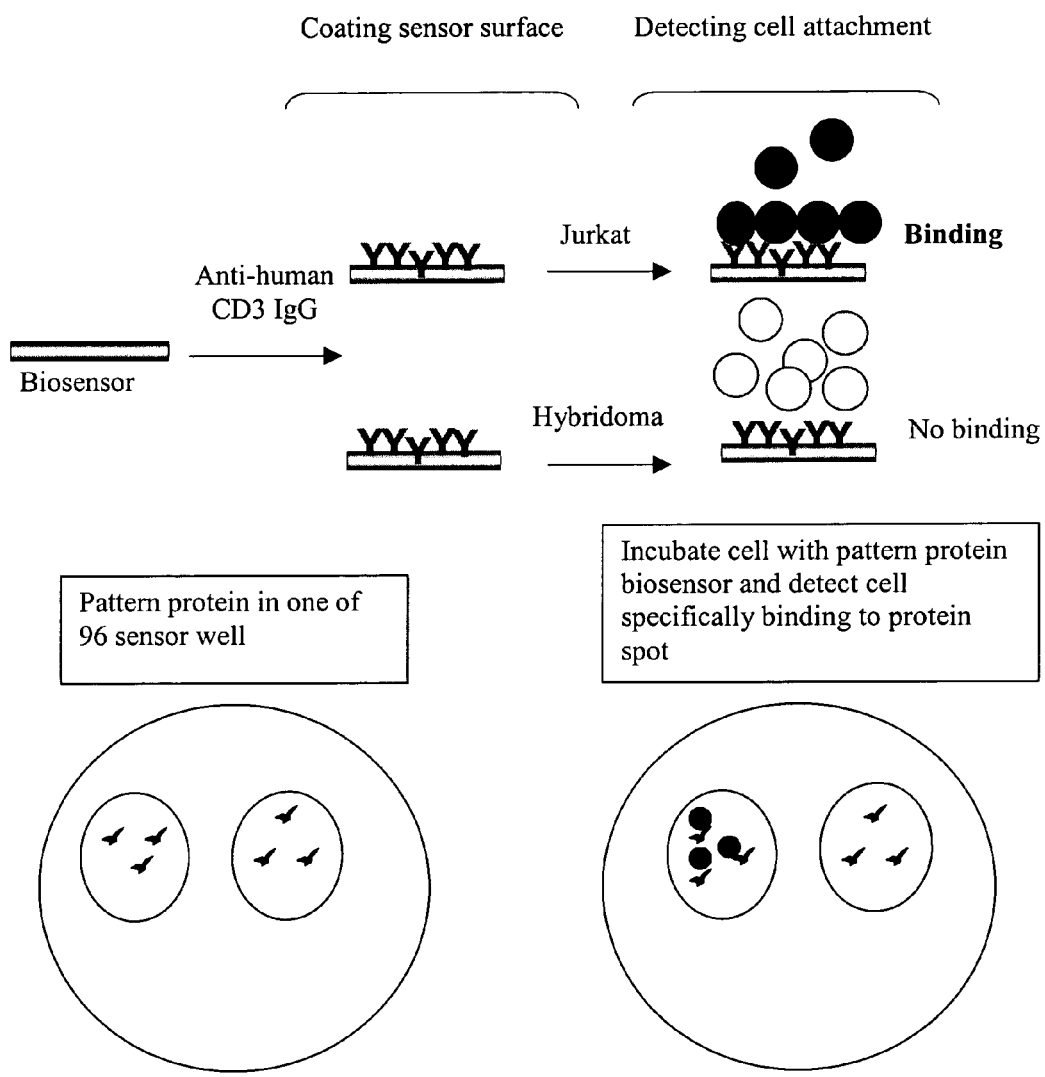
FIG. 38 shows a schematic diagram of at cell-protein interaction assay.
Figure 39:
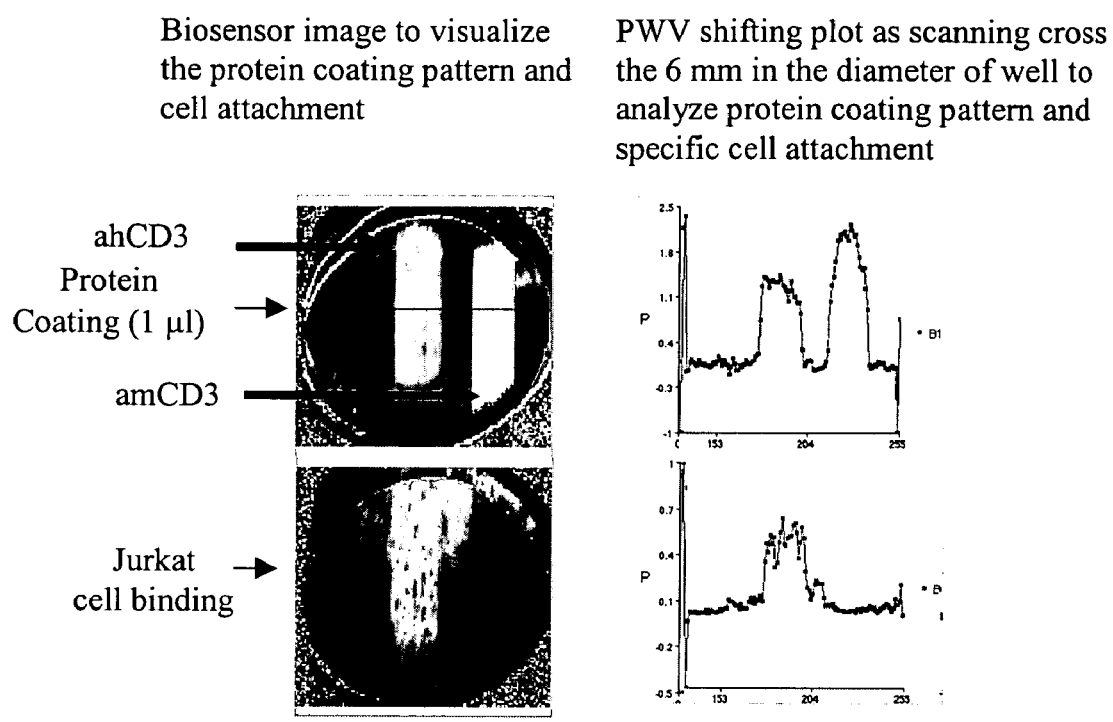
FIG. 39 shows the results from a cell-protein interaction assay.

In a working example, a microtiter well comprising a linear grating calorimetric resonant reflectance optical biosensor as an internal surface had 1 µl of anti-human CD3 and 1 µl of anti-mouse CD3 monoclonal antibody immobilized onto the surface of biosensor. See FIG. 38 and FIG. 39. The microtiter well was scanned and the antibody coating analyzed. See FIG. 39. After 20 min of incubation of Jurkat cells ($1 \times 10^5$) with the biosensor surface, the microtiter well was scanned and the cell attachment pattern was observed as shown in FIG. 39.

This assay clearly demonstrated that Jurkat cells interact with the distinct location that has been coated with ahCD3 inside of well from a 96 microplate biosensor and that no detectable signal from the distinct location with anti-mouse CD3 monoclonal antibody was observed.

These cell attachment assays can be used to identify molecules that are involved in cell adhesion, migration, chemotaxis, and invasion, for example. This assay can also be used to identify the cell surface molecules that regulate, for example, cell adhesion, migration, chemotaxis, and cell invasion. In addition, these assays can provide a novel tool to study cell-cell interactions, cell-matrix interactions, and cell-molecule interactions. Competition cell attachment assays can provide a novel tool for pharmaceutical drug screening to identify the compounds that specifically target molecules involved in cell interactions.

of a vessel, wherein the internal surface of the vessel comprises a colorimetric resonant reflectance optical biosensor;
  (b) illuminating the vessel with light;
  (c) detecting one or more peak wavelength values (PWVs) for each distinct location;
  (d) applying one or more cells to the internal surface of the vessel;
  (e) illuminating the vessel with light;
  (f) detecting one or more peak wavelength values (PWVs) for each distinct location;
  (g) comparing the PWV's of step (c) to the PWV's of step (f);
  wherein, if the one or more cells have bound to one or more specific binding substances, then the PWV is shifted at the distinct location to which the cells are bound.

2. The method of claim 1, wherein the vessel is a microtiter well, microtiter plate, test tube, petri dish or microfluidic channel.

3. The method of claim 1, wherein one or more specific binding substances are arranged in an array of distinct locations on the internal surface of the vessel that comprises a colorimetric resonant reflectance optical biosensor.

TABLE 2

|  |  | Colorimetric | Fluorescence | Radioisotope | Biosensor Of the Invention | |
|---|---|---|---|---|---|---|
|  |  |  |  |  | Adherent Cell | Suspension Cell |
| Plate Preparation | Coating Plate | 90 min | 90 min | 90 min | 30 min | 60 min |
|  | Blocking | 30 min | 30 min | 30 min | — | — |
|  | Harvest Cell | 30 min | 30 min | 30 min | 30 min | 30 min |
| Labeling Cell | Fluorescence Labeling | — | 45 min | — | — | — |
|  | 1 uCi 3[H] | — | — | 12-16 h | — | — |
|  | Washing | — | 30 min | 30 min | — | — |
| Cell Adhesion | Incubation | 120 min | 120 min | 120 min | 120 min | 120 min |
|  | Washing | 5 X PBS | 5 X PBS | 5 X PBS | — | — |
| Detection |  | 10 min: fixing cell with 96% ethanol | — | — | — | — |
|  |  | 30 min: staining 0.1% crystal violet | — | — | — | — |
|  |  | 10 min: washing | — | — | — | — |
|  |  | 10 min: lysis cell 0.2% triton | 10 min: 10% FCS | 3% SDS lysis | — | — |
|  |  | Reading OD = 570 nm | Reading in fluorimetric plate reader | Scintillation | Directly real-time monitor cell interaction with sensor surface | Directly real-time monitor cell interaction with coated sensor |
| Total Assay Time (H) |  | 5.5 h | 6 h | 16-20 h | 3 h | 3.5 h |

We claim:

1. A method of detecting binding of one or more cells to one or more specific binding substances comprising:
  (a) immobilizing one or more specific binding substances to two or more distinct locations on an internal surface 4. The method of claim 3, wherein the distinct locations define an array spot of about 50-500 microns in diameter.

5. The method of claim 1, wherein the one or more specific binding substances are immobilized on the internal surface of the vessel that comprises a colorimetric resonant reflectance optical biosensor by a method selected from the group consisting of physical adsorption, chemical binding, electrochemical binding, electrostatic binding, hydrophobic binding and hydrophilic binding.

6. The method of claim 1, wherein the specific binding substance is selected from the group consisting of nucleic acids, peptides, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, cell, virus, bacteria, polymer and biological sample.

7. The method of claim 1, wherein the one or more cells comprise more than one cell type.

8. The method of claim 1, wherein the one or more cells and the one or more specific binding substances do not comprise a detection label.

* * * * *

UNITED STATES PATENT AND TRADEMARK OFFICE
CERTIFICATE OF CORRECTION

PATENT NO.       : 7,264,973 B2  
APPLICATION NO.  : 10/667696  
DATED            : September 4, 2007  
INVENTOR(S)      : Lin et al.

It is certified that error appears in the above-identified patent and that said Letters Patent is hereby corrected as shown below:

Col. #2, Line #50, "calorimetric" should read --colorimetric--.

Col. #3, Line #35, "calorimetric" should read --colorimetric--.

Col. #5, Line #47, "calorimetric" should read --colorimetric--.

Col. #6, Lines #37, 67, "calorimetric" should read --colorimetric--.

Col. #10, Line #36, "calorimetric" should read --colorimetric--.

Col. #20, Lines #18, 59, "calorimetric" should read --colorimetric--.

Col. #22, Lines #50, 62, "calorimetric" should read --colorimetric--.

Col. #23, Line #21, "calorimetric" should read --colorimetric--.

Col. #34, Line #43, "calorimetric" should read --colorimetric--.

Col. #36, Lines #32, 64, "calorimetric" should read --colorimetric--.

Col. #37, Lines #7, 17, "calorimetric" should read --colorimetric--.

Col. #39, Lines #60, 63, "calorimetric" should read --colorimetric--.

Col. #40, Lines #24, 64, "calorimetric" should read --colorimetric--.

Signed and Sealed this

Twenty-sixth Day of August, 2008

JON W. DUDAS  
*Director of the United States Patent and Trademark Office*